US012779207B2

(12) United States Patent
Liberatore et al.

(10) Patent No.: US 12,779,207 B2
(45) Date of Patent: Nov. 3, 2026

(54) WEARABLE, ERGONOMIC NEUROSTIMULATION SYSTEM

(71) Applicant: Cala Health, Inc., San Mateo, CA (US)

(72) Inventors: Jessica M. Liberatore, San Mateo, CA (US); John Vincent Colombo, Burlingame, CA (US); Samuel Richard Hamner, San Francisco, CA (US); Kathryn H. Rosenbluth, San Francisco, CA (US)

(73) Assignee: Cala Health, Inc., San Mateo, CA (US)

( * ) Notice: Subject to any disclaimer, the term of this patent is extended or adjusted under 35 U.S.C. 154(b) by 943 days.

(21) Appl. No.: 17/052,483

(22) PCT Filed: May 2, 2019

(86) PCT No.: PCT/US2019/030458
§ 371 (c)(1),
(2) Date: Aug. 3, 2021

(87) PCT Pub. No.: WO2019/213433
PCT Pub. Date: Nov. 7, 2019

(65) Prior Publication Data

US 2021/0244940 A1 Aug. 12, 2021

Related U.S. Application Data

(60) Provisional application No. 62/666,647, filed on May 3, 2018.

(51) Int. Cl.
*A61N 1/04* (2006.01)
*A61N 1/32* (2006.01)
(Continued)

(52) U.S. Cl.
CPC ........... *A61N 1/0456* (2013.01); *A61N 1/048* (2013.01); *A61N 1/0484* (2013.01);
(Continued)

(58) Field of Classification Search
CPC ................ A61N 1/0456; A61N 1/0484; A61N 1/36034; A61N 1/3787; A61N 1/36021;
(Continued)

(56) References Cited

U.S. PATENT DOCUMENTS 3,204,637 A 9/1965 Frank et al.
3,870,051 A 3/1975 Brindley
(Continued)

FOREIGN PATENT DOCUMENTS

CN 1135722 11/1996
CN 1547483 11/2004
(Continued)

OTHER PUBLICATIONS

Pain & Spine Specialists (Apr. 12, 2024). Identifying Symptoms of Diabetic Neuropathy. https://painandspinespecialists.com/identifying-symptoms-of-diabetic-neuropathy/ (Year: 2024).*
(Continued)

*Primary Examiner* — Benjamin J Klein
*Assistant Examiner* — Daniel Tehrani
(74) *Attorney, Agent, or Firm* — Knobbe Martens Olson & Bear LLP

(57) ABSTRACT

A wearable neurostimulation device is provided for providing transcutaneous peripheral nerve stimulation to a user. The neurostimulation device may include an enclosure housing the electronics for generating electric neurostimulation signals and an adjustable band detachably coupled to the enclosure. The enclosure may include a stimulation button and one or more auxiliary buttons. The band may be configured to be worn by a user, such as around the user's wrist or arm. The band may include a locking tab which prevents the loop from being opened. The band may comprise electrodes positioned to stimulate the user's radial and median nerves. Also provided is a charger for holding and
(Continued)

charging the neurostimulation device. The band may include an RFID tag that wireless communicates with an RFID antenna in the charger. The charger may not charge the neurostimulation device if the band is determined to be beyond a threshold age.

18 Claims, 11 Drawing Sheets

(51) Int. Cl.
*A61N 1/36* (2006.01)
*H02J 7/40* (2026.01)
*H02J 7/70* (2026.01)

(52) U.S. Cl.
CPC ............ *A61N 1/36034* (2017.08); *H02J 7/40* (2026.01); *H02J 7/70* (2026.01); *A61N 1/321* (2013.01)

(58) Field of Classification Search
CPC .... A61N 2/008; A61N 1/0476; A61N 1/0492; A61N 1/36014; A61N 1/36067; A61B 590/98; A61B 590/90; A61B 5/681; A61B 5/6824; A61B 5/6831; A61B 5/6801
See application file for complete search history.

(56) References Cited

U.S. PATENT DOCUMENTS 4,103,808 A * 8/1978 Hallman .............. A44C 5/0053 368/286
4,233,986 A 11/1980 Tannenbaum
4,300,575 A 11/1981 Wilson
4,313,441 A 2/1982 Buffet
4,458,696 A 7/1984 Larimore
4,461,075 A 7/1984 Bailey
4,539,996 A 9/1985 Engel
4,569,351 A 2/1986 Tang
4,582,049 A 4/1986 Ylvisaker
4,729,377 A 3/1988 Granek et al.
4,739,764 A 4/1988 Lue et al.
4,763,659 A 8/1988 Dunseath, Jr.
4,769,881 A 9/1988 Pedigo et al.
4,771,779 A 9/1988 Tanagho et al.
4,917,092 A 4/1990 Todd et al.
4,981,146 A 1/1991 Bertolucci
4,982,432 A 1/1991 Clark et al.
4,996,987 A 3/1991 Petrofsky
5,003,978 A 4/1991 Dunseath, Jr.
5,052,391 A 10/1991 Silverstone et al.
5,070,862 A 12/1991 Berlant
5,137,507 A 8/1992 Park
5,330,516 A 7/1994 Nathan
5,395,398 A 3/1995 Rogozinski
5,397,338 A 3/1995 Grey et al.
5,433,735 A 7/1995 Zanakis et al.
5,514,175 A 5/1996 Kim et al.
5,540,235 A 7/1996 Wilson
5,562,707 A 10/1996 Prochazka et al.
5,562,717 A 10/1996 Tippey et al.
5,573,011 A 11/1996 Felsing
5,575,294 A 11/1996 Perry et al.
5,606,968 A 3/1997 Mang
5,643,173 A 7/1997 Welles
5,775,331 A 7/1998 Raymond et al.
5,833,709 A 11/1998 Rise et al.
5,833,716 A 11/1998 Bar-Or et al.
5,899,922 A 5/1999 Loos
5,961,542 A 10/1999 Agarwala
6,016,449 A 1/2000 Fischell et al.
6,076,018 A 6/2000 Sturman
6,081,744 A 6/2000 Loos
6,161,044 A 12/2000 Silverstone
6,178,352 B1 1/2001 Gruzdowich et al.
6,351,674 B2 2/2002 Silverstone
6,364,841 B1 4/2002 White et al.
6,366,813 B1 4/2002 DiLorenzo
6,366,814 B1 4/2002 Boveja et al.
6,419,644 B1 7/2002 White et al.
6,445,955 B1 9/2002 Michelson et al.
6,449,512 B1 9/2002 Boveja
6,453,204 B1 9/2002 Rhoads
6,505,074 B2 1/2003 Boveja et al.
6,546,290 B1 4/2003 Shloznikov
6,564,103 B2 5/2003 Fischer et al.
6,572,555 B2 6/2003 White et al.
6,579,270 B2 6/2003 Sussman et al.
6,641,546 B2 11/2003 White et al.
6,652,449 B1 11/2003 Gross et al.
6,662,052 B1 12/2003 Sarwal et al.
6,678,548 B1 1/2004 Echauz et al.
6,701,185 B2 3/2004 Burnett et al.
6,704,603 B1 3/2004 Gesotti
6,731,987 B1 5/2004 McAdams et al.
6,735,474 B1 5/2004 Loeb et al.
6,735,480 B2 5/2004 Giuntoli et al.
6,788,976 B2 9/2004 Gesotti
6,819,956 B2 11/2004 DiLorenzo
6,827,693 B2 12/2004 White et al.
6,829,510 B2 12/2004 Nathan et al.
6,836,684 B1 12/2004 Rijkhoff et al.
6,862,480 B2 3/2005 Cohen et al.
6,892,098 B2 5/2005 Ayal et al.
6,937,905 B2 8/2005 Carroll et al.
6,959,215 B2 10/2005 Gliner et al.
6,959,216 B2 10/2005 Faghri
6,988,005 B2 1/2006 McGraw et al.
7,010,352 B2 3/2006 Hogan
7,089,061 B2 8/2006 Grey
7,146,220 B2 12/2006 Dar et al.
7,162,305 B2 1/2007 Tong et al.
7,171,266 B2 1/2007 Gruzdowich et al.
7,177,694 B2 2/2007 Elbaum
7,177,703 B2 2/2007 Boveja et al.
7,209,787 B2 4/2007 DiLorenzo
7,228,178 B2 6/2007 Carroll et al.
7,231,254 B2 6/2007 DiLorenzo
7,236,830 B2 6/2007 Gliner
7,254,444 B2 8/2007 Moore et al.
7,277,758 B2 10/2007 DiLorenzo
7,283,866 B2 10/2007 Mumford et al.
7,324,851 B1 1/2008 DiLorenzo
7,326,235 B2 2/2008 Edwards
7,328,068 B2 2/2008 Spinelli et al.
7,349,739 B2 3/2008 Harry et al.
7,353,064 B2 4/2008 Gliner et al.
7,369,896 B2 5/2008 Gesotti
7,499,747 B2 3/2009 Kieval et al.
7,529,582 B1 5/2009 DiLorenzo
7,558,610 B1 7/2009 Odderson
7,636,602 B2 12/2009 Baru Fassio et al.
7,640,052 B2 12/2009 Weinstock
7,643,880 B2 1/2010 Tanagho et al.
7,643,882 B2 1/2010 Boston
7,647,112 B2 1/2010 Tracey et al.
7,650,190 B2 1/2010 Zhou et al.
7,657,317 B2 2/2010 Thacker et al.
7,660,632 B2 2/2010 Kirby et al.
7,742,820 B2 6/2010 Wyler et al.
7,761,166 B2 7/2010 Giftakis et al.
7,769,464 B2 8/2010 Gerber et al.
7,801,585 B1 9/2010 Weinstock
7,857,771 B2 12/2010 Alwan et al.
7,899,527 B2 3/2011 Yun et al.
7,899,556 B2 3/2011 Nathan et al.
7,917,201 B2 3/2011 Gozani et al.
7,930,034 B2 4/2011 Gerber
7,949,403 B2 5/2011 Palermo et al.
7,957,814 B2 6/2011 Goetz et al.
7,974,696 B1 7/2011 DiLorenzo
7,974,698 B2 7/2011 Tass et al.
7,991,476 B2 8/2011 Nachum

(56) References Cited

U.S. PATENT DOCUMENTS 7,996,088 B2 8/2011 Marrosu et al.
7,998,092 B2 8/2011 Avni
8,000,796 B2 8/2011 Tass
8,025,632 B2 9/2011 Einarsson
8,046,083 B2 10/2011 Tegenthoff et al.
8,064,988 B2 11/2011 Weinstock
8,075,499 B2 12/2011 Nathan et al.
8,086,318 B2 12/2011 Strother et al.
8,108,047 B2 1/2012 Schumann
8,121,694 B2 2/2012 Molnar et al.
8,145,316 B2 3/2012 Deem et al.
8,165,668 B2 4/2012 Dacey, Jr. et al.
8,165,685 B1 4/2012 Knutson et al.
8,170,658 B2 5/2012 Dacey, Jr. et al.
8,175,718 B2 5/2012 Wahlgren et al.
8,187,209 B1 5/2012 Guiffrida et al.
8,190,249 B1 5/2012 Gharieb et al.
8,195,287 B2 6/2012 Dacey, Jr. et al.
8,209,036 B2 6/2012 Nathan et al.
8,219,188 B2 7/2012 Craig
8,233,988 B2 7/2012 Errico et al.
8,260,439 B2 9/2012 Diubaldi et al.
8,265,763 B2 9/2012 Fahey
8,280,513 B2 10/2012 Tehrani et al.
8,301,215 B2 10/2012 Lee
8,306,624 B2 11/2012 Gerber et al.
8,308,665 B2 11/2012 Harry et al.
8,313,443 B2 11/2012 Tom
8,326,398 B2 12/2012 Weinstock
8,326,432 B2 12/2012 Kalisek
8,343,026 B2 1/2013 Gardiner et al.
8,364,257 B2 1/2013 Van Den Eerenbeemd et al.
8,374,701 B2 2/2013 Hyde et al.
8,380,314 B2 2/2013 Panken et al.
8,382,688 B2 2/2013 Dar et al.
8,391,970 B2 3/2013 Tracey et al.
8,396,556 B2 3/2013 Libbus et al.
8,406,841 B2 3/2013 Lin et al.
8,409,116 B2 4/2013 Wang et al.
8,412,338 B2 4/2013 Faltys
8,414,507 B2 4/2013 Asada
8,417,351 B2 4/2013 Kilger
8,428,719 B2 4/2013 Napadow
8,430,805 B2 4/2013 Burnett et al.
8,435,166 B2 5/2013 Burnett et al.
8,447,411 B2 5/2013 Skelton et al.
8,452,410 B2 5/2013 Emborg et al.
8,463,374 B2 6/2013 Hudson et al.
8,467,876 B2 6/2013 Tehrani
8,473,064 B2 6/2013 Castel et al.
8,504,161 B1 8/2013 Kornet et al.
8,538,512 B1 9/2013 Bibian et al.
8,548,594 B2 10/2013 Thimineur et al.
8,571,687 B2 10/2013 Libbus et al.
8,581,731 B2 11/2013 Purks et al.
8,583,238 B1 11/2013 Heldman et al.
8,588,884 B2 11/2013 Hegde et al.
8,588,917 B2 11/2013 Whitehurst et al.
8,588,919 B2 11/2013 Li
8,608,671 B2 12/2013 Kinoshita et al.
8,626,305 B2 1/2014 Nielsen et al.
8,639,342 B2 1/2014 Possover
8,644,904 B2 2/2014 Chang et al.
8,644,921 B2 2/2014 Wilson
8,644,938 B2 2/2014 Craggs
8,660,644 B2 2/2014 Jaxx et al.
8,660,653 B2 2/2014 Kothandaraman et al.
8,660,656 B2 2/2014 Moser et al.
8,666,496 B2 3/2014 Simon et al.
8,679,038 B1 3/2014 Giuffrida
8,682,441 B2 3/2014 De Ridder
8,688,220 B2 4/2014 Degiorgio et al.
8,694,104 B2 4/2014 Libbus et al.
8,694,110 B2 4/2014 Nathan et al.
8,702,584 B2 4/2014 Rigaux et al.
8,702,629 B2 4/2014 Giuffrida et al.
8,706,241 B2 4/2014 Firlik et al.
8,718,780 B2 5/2014 Lee
8,729,129 B2 5/2014 Tracey et al.
8,738,143 B2 5/2014 Tucker et al.
8,740,825 B2 6/2014 Ehrenreich et al.
8,744,587 B2 6/2014 Miesel et al.
8,755,889 B2 6/2014 Scheiner
8,755,892 B2 6/2014 Amurthur et al.
D709,874 S 7/2014 Aumiller et al.
8,768,452 B2 7/2014 Gerber
8,788,045 B2 7/2014 Gross et al.
8,788,049 B2 7/2014 Lasko et al.
8,792,977 B2 7/2014 Kakei et al.
8,798,698 B2 8/2014 Kim et al.
8,821,416 B2 9/2014 Johansson et al.
8,825,163 B2 9/2014 Grill et al.
8,825,165 B2 9/2014 Possover
8,825,166 B2 9/2014 John
8,843,201 B1 9/2014 Heldman et al.
8,845,494 B2 9/2014 Whitall et al.
8,845,557 B1 9/2014 Giuffrida et al.
8,849,371 B2 9/2014 Weinstock
8,855,775 B2 10/2014 Leyde
8,862,238 B2 10/2014 Rahimi et al.
8,862,247 B2 10/2014 Schoendorf et al.
8,868,177 B2 10/2014 Simon et al.
8,874,227 B2 10/2014 Simon et al.
8,880,175 B2 11/2014 Simon
8,886,321 B2 11/2014 Rohrer et al.
8,892,200 B2 11/2014 Wagner et al.
8,897,870 B2 11/2014 De Ridder
8,903,494 B2 12/2014 Goldwasser et al.
8,920,345 B2 12/2014 Greenberg et al.
8,923,970 B2 12/2014 Bar-Yoseph et al.
8,923,971 B2 12/2014 Haefner et al.
8,948,876 B2 2/2015 Gozani et al.
8,958,884 B2 2/2015 Kothandaraman et al.
8,961,439 B2 2/2015 Yang et al.
8,972,017 B2 3/2015 Dar et al.
8,989,861 B2 3/2015 Su et al.
9,002,477 B2 4/2015 Burnett
9,005,102 B2 4/2015 Burnett et al.
9,008,781 B2 4/2015 Ahmed
9,011,310 B2 4/2015 Ahmed
9,017,273 B2 4/2015 Burbank et al.
9,026,216 B2 5/2015 Rossi et al.
9,042,988 B2 5/2015 Dilorenzo
9,044,587 B2 6/2015 Bachinski et al.
9,060,747 B2 6/2015 Salorio
9,079,029 B2 7/2015 Weinstock
9,089,691 B2 7/2015 Libbus et al.
9,095,351 B2 8/2015 Sachs et al.
9,095,417 B2 8/2015 Dar et al.
9,107,614 B2 8/2015 Halkias et al.
9,119,964 B2 9/2015 Marnfeldt
9,155,885 B2 10/2015 Wei et al.
9,155,890 B2 10/2015 Guntinas-Lichius et al.
9,162,059 B1 10/2015 Lindenthaler
9,168,374 B2 10/2015 Su
9,174,045 B2 11/2015 Simon et al.
9,186,095 B2 11/2015 Machado et al.
9,186,511 B2 11/2015 Bolea
9,192,763 B2 11/2015 Gerber et al.
9,211,409 B2 12/2015 Tracey et al.
9,211,417 B2 12/2015 Giuffrida et al.
9,220,431 B2 12/2015 Holzhacker
9,220,895 B2 12/2015 Siff et al.
9,227,056 B1 1/2016 Heldman et al.
9,238,137 B2 1/2016 Einav et al.
9,238,142 B2 1/2016 Heldman et al.
9,242,085 B2 1/2016 Hershey et al.
9,242,091 B2 1/2016 Bachinski et al.
9,248,285 B2 2/2016 Haessler
9,248,286 B2 2/2016 Simon et al.
9,248,297 B2 2/2016 Hoyer et al.
9,254,382 B2 2/2016 Ahmad et al.
9,259,573 B2 2/2016 Tehrani et al.
9,259,577 B2 2/2016 Kaula et al.

(56) References Cited

U.S. PATENT DOCUMENTS 9,265,927 B2 2/2016 Yonce et al.
9,282,928 B1 3/2016 Giffrida
9,289,603 B1 3/2016 Giuffrida et al.
9,289,607 B2 3/2016 Su et al.
9,301,712 B2 4/2016 McNames et al.
9,302,046 B1 4/2016 Giuffrida et al.
9,302,117 B2 4/2016 De Vincentiis
9,311,686 B2 4/2016 Roush et al.
9,314,190 B1 4/2016 Giuffrida et al.
9,314,622 B2 4/2016 Embrey et al.
9,332,918 B1 5/2016 Buckley et al.
9,339,213 B2 5/2016 Otsamo et al.
9,339,641 B2 5/2016 Rajguru et al.
9,345,872 B2 5/2016 Groteke
9,364,657 B2 6/2016 Kiani et al.
9,364,672 B2 6/2016 Marnfeldt
9,375,570 B2 6/2016 Kiani et al.
9,387,338 B2 7/2016 Burnett
9,393,418 B2 7/2016 Giuffrida et al.
9,393,430 B2 7/2016 Demers et al.
9,403,013 B2 8/2016 Walker et al.
9,408,683 B2 8/2016 St. Anne et al.
9,414,776 B2 8/2016 Sillay et al.
9,415,205 B2 8/2016 Lasko et al.
D767,436 S 9/2016 Goodner et al.
9,452,287 B2 9/2016 Rosenbluth et al.
9,468,753 B2 10/2016 Fisher et al.
9,474,898 B2 10/2016 Gozani et al.
9,522,278 B1 12/2016 Giuffrida et al.
9,533,154 B2 1/2017 Kothandaraman et al.
9,549,872 B2 1/2017 Chen et al.
9,550,068 B2 1/2017 Weinstock
9,581,972 B1 * 2/2017 Arrow .................... G04G 21/00
9,586,038 B1 3/2017 Kosierkiewicz
9,589,698 B2 3/2017 Anhalt et al.
9,597,509 B2 3/2017 Hoffer et al.
9,610,442 B2 4/2017 Yoo et al.
9,610,459 B2 4/2017 Burnett et al.
9,615,797 B2 4/2017 John
9,630,004 B2 4/2017 Rajguru et al.
9,649,486 B2 5/2017 Holzhacker
9,656,070 B2 5/2017 Gozani et al.
9,662,490 B2 5/2017 Tracey et al.
9,662,502 B2 5/2017 Giuffrida et al.
9,669,211 B2 6/2017 Wijting et al.
9,675,800 B2 6/2017 Li et al.
9,675,801 B2 6/2017 Kong et al.
9,682,235 B1 6/2017 O'Mahony et al.
9,707,393 B2 7/2017 Hsueh et al.
9,717,920 B1 8/2017 Giuffrida et al.
9,717,921 B2 8/2017 Perryman et al.
9,731,126 B2 8/2017 Ferree et al.
9,757,584 B2 9/2017 Burnett
9,776,005 B2 10/2017 Meyyappan et al.
9,782,122 B1 10/2017 Giuffrida et al.
9,782,584 B2 10/2017 Cartledge et al.
9,802,041 B2 10/2017 Wong et al.
9,802,046 B2 10/2017 Grill et al.
9,826,921 B2 11/2017 Griffiths et al.
9,861,283 B1 1/2018 Giuffrida
9,861,817 B2 1/2018 Cho et al.
9,877,679 B1 1/2018 Giuffrida
9,877,680 B1 1/2018 Giuffrida et al.
9,878,158 B2 1/2018 Hershey et al.
9,884,179 B2 2/2018 Bouton et al.
9,901,299 B2 2/2018 Haviv et al.
9,907,960 B2 3/2018 Lian et al.
9,924,899 B2 3/2018 Pracar et al.
9,956,132 B2 5/2018 Francois et al.
9,956,395 B2 5/2018 Bikson et al.
9,962,549 B2 5/2018 Kothandaraman et al.
9,974,478 B1 5/2018 Brokaw et al.
9,980,659 B2 5/2018 Sadeghian-Motahar et al.
9,987,488 B1 6/2018 Gelfand et al.
9,992,918 B2 6/2018 Watanabe et al.
10,004,900 B2 6/2018 Kent et al.
10,016,600 B2 7/2018 Creasey et al.
10,022,545 B1 7/2018 Giuffrida
10,028,695 B2 7/2018 Machado et al.
10,039,928 B2 8/2018 Hyde et al.
10,045,740 B2 8/2018 John
10,046,161 B2 8/2018 Biasiucci et al.
D828,351 S 9/2018 Xi et al.
10,076,656 B2 9/2018 Dar et al.
10,080,885 B2 9/2018 Nathan et al.
10,085,670 B2 10/2018 Crosson et al.
10,085,689 B1 10/2018 Giuffrida et al.
10,092,754 B1 10/2018 Giuffrida et al.
10,099,057 B2 10/2018 Kent et al.
10,112,040 B2 10/2018 Herb et al.
10,118,035 B2 11/2018 Perez et al.
10,118,049 B2 11/2018 Matthews
10,124,169 B2 11/2018 Sabesan et al.
10,130,809 B2 11/2018 Cartledge et al.
10,130,810 B2 11/2018 Ferree et al.
10,134,378 B1 11/2018 Cenci et al.
10,137,025 B2 11/2018 Fior et al.
10,173,060 B2 1/2019 Wong et al.
10,179,238 B2 1/2019 Wong et al.
10,188,863 B2 1/2019 Kaemmerer et al.
10,199,125 B2 2/2019 Rao et al.
10,201,705 B2 2/2019 Bharmi et al.
10,213,593 B2 2/2019 Kaplan et al.
10,213,602 B2 2/2019 Ironi et al.
10,232,174 B2 3/2019 Simon et al.
10,232,179 B2 3/2019 Grill et al.
10,252,053 B2 4/2019 Page et al.
10,258,798 B2 4/2019 Panken et al.
10,265,523 B2 4/2019 Simon et al.
10,285,602 B2 5/2019 Tognetti et al.
10,285,646 B1 5/2019 Grant et al.
10,286,210 B2 5/2019 Yoo
10,293,159 B2 5/2019 Kong et al.
10,335,396 B2 7/2019 Nemechek
10,335,594 B2 7/2019 Lin et al.
10,335,595 B2 7/2019 Ferree et al.
10,342,977 B2 7/2019 Raghunathan
10,363,415 B2 7/2019 Simon et al.
10,383,571 B1 8/2019 Giuffrida et al.
10,398,896 B2 9/2019 Lin et al.
10,441,787 B2 10/2019 Canning et al.
10,456,573 B1 10/2019 Feinstein et al.
10,463,854 B2 11/2019 Perez
10,478,626 B1 11/2019 Giuffrida et al.
10,485,971 B2 11/2019 Schepis et al.
10,493,281 B2 12/2019 Giftakis et al.
10,499,848 B2 12/2019 Weinstock
10,500,396 B2 12/2019 Tamaki et al.
10,506,944 B2 12/2019 Tognetti et al.
10,507,327 B2 12/2019 Tracey et al.
10,518,090 B2 12/2019 Gelfand et al.
10,537,732 B2 1/2020 Nachum et al.
10,549,093 B2 2/2020 Wong et al.
10,556,107 B2 2/2020 Yoo et al.
10,561,839 B2 2/2020 Wong et al.
10,561,844 B2 2/2020 Meyyappan et al.
10,589,097 B2 3/2020 Meyyappan et al.
10,603,482 B2 3/2020 Hamner et al.
10,610,114 B2 4/2020 Buckley et al.
10,625,074 B2 4/2020 Rosenbluth et al.
10,632,312 B2 4/2020 Ziv
10,661,082 B2 5/2020 Kerselaers
10,679,599 B2 6/2020 Cenci et al.
10,694,992 B1 6/2020 Giuffrida et al.
10,695,568 B1 6/2020 Covalin
10,695,569 B2 6/2020 Levine et al.
10,698,492 B2 6/2020 Daniels
10,716,941 B2 7/2020 Yang et al.
10,722,709 B2 7/2020 Yoo et al.
10,736,577 B2 8/2020 Horne
10,750,946 B1 8/2020 Giuffrida
10,758,732 B1 9/2020 Heldman
10,765,856 B2 9/2020 Wong et al.
10,773,079 B2 9/2020 Keller et al.

(56) References Cited

U.S. PATENT DOCUMENTS

| | | | |
|---|---|---|---|
| 10,780,269 | B2 | 9/2020 | Gozani et al. |
| 10,786,199 | B1 | 9/2020 | Giuffrida et al. |
| 10,786,200 | B1 | 9/2020 | Giuffrida |
| 10,786,625 | B1 | 9/2020 | Giuffrida et al. |
| 10,786,669 | B2 | 9/2020 | Rajguru et al. |
| 10,806,928 | B2 | 10/2020 | Sharma et al. |
| 10,814,130 | B2 | 10/2020 | Wong et al. |
| 10,814,131 | B2 | 10/2020 | Goldwasser et al. |
| D902,769 | S | 11/2020 | Riot et al. |
| 10,835,736 | B2 | 11/2020 | Horter et al. |
| 10,850,090 | B2 | 12/2020 | Rosenbluth et al. |
| 10,857,363 | B2 | 12/2020 | Tehrani |
| 10,870,002 | B2 | 12/2020 | Wybo et al. |
| 10,881,854 | B2 | 1/2021 | Son et al. |
| 10,881,856 | B2 | 1/2021 | Giuffrida et al. |
| 10,898,124 | B1 | 1/2021 | Fafiani et al. |
| 10,898,709 | B2 | 1/2021 | Wagner et al. |
| 10,905,879 | B2 | 2/2021 | Wong et al. |
| 10,912,712 | B2 | 2/2021 | Tracey et al. |
| 10,918,853 | B2 | 2/2021 | Creasey et al. |
| 10,918,867 | B2 | 2/2021 | Walker |
| 10,933,240 | B2 | 3/2021 | Kressel et al. |
| 10,940,311 | B2 | 3/2021 | Gozani et al. |
| 10,945,879 | B2 | 3/2021 | Black et al. |
| 10,960,207 | B2 | 3/2021 | Wong et al. |
| D915,399 | S | 4/2021 | Chao et al. |
| 10,966,652 | B1 | 4/2021 | Giuffrida et al. |
| 10,967,177 | B2 | 4/2021 | Lee |
| 10,967,182 | B2 | 4/2021 | Khodaparast et al. |
| 10,974,049 | B1 | 4/2021 | Giuffrida et al. |
| 10,981,007 | B2 | 4/2021 | Patel et al. |
| 10,994,132 | B1 | 5/2021 | Giuffrida et al. |
| 11,004,563 | B2 | 5/2021 | Lin et al. |
| 11,020,591 | B2 | 6/2021 | Errico et al. |
| 11,026,835 | B2 | 6/2021 | Black et al. |
| 11,027,116 | B2 | 6/2021 | Kong et al. |
| 11,027,130 | B2 | 6/2021 | Hoffer |
| 11,033,206 | B2 | 6/2021 | Roh |
| 11,033,731 | B2 | 6/2021 | Jeffery et al. |
| 11,033,736 | B2 | 6/2021 | Edgerton et al. |
| 11,040,198 | B1 | 6/2021 | Giuffrida et al. |
| 11,040,203 | B1 | 6/2021 | Giuffrida et al. |
| 11,058,867 | B2 | 7/2021 | Nathan et al. |
| 11,077,300 | B2 | 8/2021 | McBride |
| 11,077,301 | B2 | 8/2021 | Creasey et al. |
| 11,079,225 | B2 | 8/2021 | Ong et al. |
| 11,103,691 | B2 | 8/2021 | Charlesworth et al. |
| 11,103,699 | B1 | 8/2021 | Oppenheim et al. |
| 11,123,562 | B1 | 9/2021 | Giuffrida et al. |
| 11,141,586 | B2 | 10/2021 | Campean et al. |
| 11,141,587 | B2 | 10/2021 | Campean et al. |
| 11,160,971 | B2 | 11/2021 | Sharma et al. |
| 11,160,979 | B1 | 11/2021 | Giuffrida et al. |
| 11,166,632 | B2 | 11/2021 | Grossman et al. |
| 11,191,959 | B2 | 12/2021 | Ben-David et al. |
| 11,191,967 | B1 | 12/2021 | Giuffrida et al. |
| 11,191,968 | B1 | 12/2021 | Giuffrida et al. |
| 11,197,999 | B2 | 12/2021 | Crosson |
| 11,207,518 | B2 | 12/2021 | Huston et al. |
| 11,213,681 | B2 | 1/2022 | Raghunathan |
| 11,224,742 | B2 | 1/2022 | Burnett |
| 11,247,040 | B2 | 2/2022 | Ferree et al. |
| 11,247,053 | B2 | 2/2022 | Rajguru et al. |
| 11,247,056 | B2 | 2/2022 | Hareland et al. |
| 11,260,225 | B2 | 3/2022 | Errico et al. |
| 11,266,836 | B2 | 3/2022 | Charlesworth et al. |
| 11,266,838 | B1 | 3/2022 | Tehrani |
| 11,278,724 | B2 | 3/2022 | Law et al. |
| 11,285,321 | B2 | 3/2022 | Ganguly et al. |
| 11,311,235 | B1 | 4/2022 | Giuffrida et al. |
| 11,318,296 | B2 | 5/2022 | Xiao et al. |
| 11,318,307 | B2 | 5/2022 | Kern et al. |
| 11,324,954 | B2 | 5/2022 | Bhattacharya et al. |
| 11,331,480 | B2 | 5/2022 | Hamner et al. |
| 11,338,120 | B2 | 5/2022 | Yun et al. |
| 11,338,128 | B2 | 5/2022 | Lawson et al. |
| 11,344,722 | B2 | 5/2022 | Wong et al. |
| 11,344,732 | B2 | 5/2022 | Moffitt et al. |
| 11,357,981 | B2 | 6/2022 | Moaddeb et al. |
| 11,363,982 | B1 | 6/2022 | Giuffrida et al. |
| 11,367,519 | B1 | 6/2022 | Heldman et al. |
| 11,383,087 | B1 | 7/2022 | Heldman et al. |
| 11,389,074 | B2 | 7/2022 | Togenetti et al. |
| 11,389,651 | B2 | 7/2022 | Tamaki et al. |
| 11,400,288 | B2 | 8/2022 | Simon et al. |
| 11,419,515 | B2 | 8/2022 | Crosson et al. |
| 11,420,052 | B2 | 8/2022 | Doskocil et al. |
| 11,420,054 | B2 | 8/2022 | Page et al. |
| 11,424,755 | B2 | 8/2022 | Yang et al. |
| D962,929 | S | 9/2022 | He et al. |
| 11,433,237 | B2 | 9/2022 | Lovett |
| 11,471,685 | B2 | 10/2022 | Bolea |
| 11,484,710 | B2 | 11/2022 | Mantovani et al. |
| 11,497,915 | B2 | 11/2022 | Tehrani |
| 11,504,530 | B2 | 11/2022 | Herr et al. |
| 11,517,753 | B2 | 12/2022 | Rhodes |
| 11,523,754 | B2 | 12/2022 | Battista |
| 11,529,283 | B2 | 12/2022 | Francois et al. |
| 11,534,605 | B2 | 12/2022 | Bouton et al. |
| 11,541,239 | B2 | 1/2023 | Tracey et al. |
| 11,547,316 | B2 | 1/2023 | Crosson et al. |
| 11,559,250 | B1 | 1/2023 | Giuffrida et al. |
| 11,590,348 | B2 | 2/2023 | Moaddeb et al. |
| 11,596,327 | B2 | 3/2023 | Griffiths et al. |
| 11,596,785 | B2 | 3/2023 | Hamner et al. |
| 11,596,791 | B2 | 3/2023 | Wong et al. |
| 11,596,792 | B2 | 3/2023 | Campean et al. |
| 11,607,167 | B2 | 3/2023 | Han et al. |
| 11,623,078 | B2 | 4/2023 | Simon et al. |
| 11,628,300 | B2 | 4/2023 | Rajguru et al. |
| 11,642,513 | B2 | 5/2023 | Sharma et al. |
| 11,642,529 | B2 | 5/2023 | Suri et al. |
| 11,666,758 | B2 | 6/2023 | Crosson |
| 11,672,981 | B2 | 6/2023 | Jaasma et al. |
| 11,701,293 | B2 | 7/2023 | Carballo et al. |
| 11,717,682 | B2 | 8/2023 | Gozani et al. |
| 11,744,482 | B1 | 9/2023 | Giuffrida et al. |
| 11,759,642 | B1 | 9/2023 | Heldman |
| 11,766,187 | B2 | 9/2023 | Togenetti et al. |
| 11,766,191 | B2 | 9/2023 | Sharma et al. |
| 11,779,764 | B2 | 10/2023 | Pepin et al. |
| 11,786,727 | B2 | 10/2023 | Colborn et al. |
| 11,786,730 | B1 | 10/2023 | Giuffrida et al. |
| 11,786,735 | B1 | 10/2023 | Giuffrida et al. |
| 11,794,012 | B2 | 10/2023 | Napadow et al. |
| 11,794,013 | B2 | 10/2023 | Kressel et al. |
| 11,809,629 | B1 | 11/2023 | Segil et al. |
| 11,833,352 | B2 | 12/2023 | Law et al. |
| 11,839,583 | B1 | 12/2023 | Carballo et al. |
| 11,839,762 | B2 | 12/2023 | Doskocil et al. |
| 11,844,943 | B2 | 12/2023 | Rajguru et al. |
| 11,844,945 | B1 | 12/2023 | Giuffrida et al. |
| 11,857,778 | B2 | 1/2024 | Hamner et al. |
| 11,872,399 | B2 | 1/2024 | Raghunathan |
| 11,878,166 | B2 | 1/2024 | Colburn et al. |
| 11,890,468 | B1 | 2/2024 | Yu |
| 11,890,469 | B2 | 2/2024 | Moaddeb et al. |
| 11,890,475 | B2 | 2/2024 | Vaidyanathan |
| 11,896,824 | B2 | 2/2024 | Doskocil |
| 11,911,604 | B2 | 2/2024 | Sharma et al. |
| 11,911,605 | B2 | 2/2024 | Crosson et al. |
| 11,911,609 | B1 | 2/2024 | Heldman et al. |
| 11,918,806 | B2 | 3/2024 | Wong et al. |
| 11,918,810 | B1 | 3/2024 | Giuffrida et al. |
| 11,918,826 | B2 | 3/2024 | Smith et al. |
| 11,922,915 | B2 | 3/2024 | Cenci et al. |
| 11,931,578 | B2 | 3/2024 | Shelton et al. |
| 11,975,190 | B2 | 5/2024 | Cho et al. |
| 11,975,195 | B1 | 5/2024 | Giuffrida et al. |
| 11,986,317 | B1 | 5/2024 | Heldman et al. |
| 11,992,682 | B2 | 5/2024 | Crawford |
| 11,992,685 | B2 | 5/2024 | Kassiri Bidhendi et al. |
| 12,029,287 | B2 | 7/2024 | Ye et al. |
| 12,029,899 | B1 | 7/2024 | Kostopoulos |

(56) References Cited

U.S. PATENT DOCUMENTS 12,053,627 B2 8/2024 Stanslaski et al.
12,070,601 B2 8/2024 Martins et al.
12,083,334 B2 9/2024 Burnett
12,109,413 B2 10/2024 Wong et al.
12,138,007 B2 11/2024 Sharareh
12,138,452 B2 11/2024 Arbel et al.
12,144,993 B2 11/2024 Bauer
12,157,001 B2 12/2024 Wong et al.
12,161,478 B1 12/2024 Heldman et al.
12,161,858 B2 12/2024 Rosenbluth et al.
12,161,865 B2 12/2024 Hamner et al.
12,172,015 B2 12/2024 Simon et al.
12,179,012 B2 12/2024 Simon et al.
12,182,328 B2 12/2024 Segil et al.
12,186,085 B2 1/2025 Buckley et al.
12,186,548 B2 1/2025 Jackson et al.
12,214,204 B1 2/2025 Giuffrida et al.
12,223,265 B2 2/2025 Hamner et al.
12,226,632 B2 2/2025 Rajguru et al.
12,237,121 B2 2/2025 Ye et al.
D1,066,701 S 3/2025 Raghunathan et al.
D1,066,702 S 3/2025 Raghunathan et al.
12,251,560 B1 3/2025 Balbaky et al.
D1,069,129 S 4/2025 Raghunathan et al.
12,262,979 B2 4/2025 Togenetti et al.
12,263,009 B1 4/2025 Giuffrida et al.
12,263,342 B2 4/2025 Elyahoodayan et al.
12,280,258 B2 4/2025 Hughes et al.
12,285,610 B1 4/2025 Giuffrida et al.
12,290,687 B2 5/2025 Shelton et al.
12,311,175 B2 5/2025 Charlesworth et al.
12,318,341 B2 6/2025 Carballo et al.
12,318,342 B2 6/2025 Carballo et al.
12,329,716 B2 6/2025 Francois et al.
12,343,532 B1 7/2025 Chakravarthy
12,357,196 B2 7/2025 Sharma et al.
12,357,824 B2 7/2025 Wong et al.
12,380,980 B1 8/2025 Heldman et al.
12,409,323 B1 9/2025 Giuffrida et al.
12,414,704 B2 9/2025 Verzal et al.
12,420,082 B2 9/2025 Hamner et al.
12,449,899 B2 10/2025 VanWyk et al.
12,453,853 B2 10/2025 Rosenbluth et al.
12,453,855 B2 10/2025 Keenan
12,465,215 B2 11/2025 Fotiadis
12,465,272 B2 11/2025 Dundovic et al.
12,465,764 B1 11/2025 Covalin et al.
12,472,357 B2 11/2025 Dieken et al.
12,485,275 B2 12/2025 Atkin et al.
12,491,367 B2 12/2025 Tracey et al.
12,496,447 B2 12/2025 Lim et al.
12,502,121 B1 12/2025 Giuffrida
12,502,527 B2 12/2025 Covalin et al.
12,502,536 B2 12/2025 Moaddeb et al.
12,515,046 B2 1/2026 Leuthardt et al.
12,569,681 B2 3/2026 Meyyappan et al.
12,575,780 B2 3/2026 Hamner et al.
12,576,273 B2 3/2026 Song et al.
12,629,522 B1 5/2026 Yu
2001/0020177 A1 9/2001 Gruzdowich et al.
2001/0056290 A1 12/2001 Fischell et al.
2002/0055761 A1 5/2002 Mann et al.
2002/0070252 A1 6/2002 Bauer
2002/0120183 A1 8/2002 Abraham-Fuchs et al.
2002/0138116 A1 9/2002 Bertolucci
2002/0161415 A1 10/2002 Cohen et al.
2002/0165586 A1 11/2002 Hill et al.
2002/0177882 A1 11/2002 DiLorenzo
2003/0032992 A1 2/2003 Thacker et al.
2003/0045922 A1 3/2003 Northrop
2003/0088294 A1 5/2003 Gesotti
2003/0093098 A1 5/2003 Heitzmann et al.
2003/0100932 A1 5/2003 Ciaff
2003/0149457 A1 8/2003 Tcheng et al.
2003/0181959 A1 9/2003 Dobak, III
2003/0187483 A1 10/2003 Grey et al.
2003/0191506 A1 10/2003 Shloznikov
2003/0195583 A1 10/2003 Gruzdowich et al.
2004/0015094 A1 1/2004 Manabe et al.
2004/0088025 A1 5/2004 Gessotti
2004/0093093 A1 5/2004 Andrews
2004/0102819 A1 5/2004 Zou et al.
2004/0111129 A1 6/2004 Gliner et al.
2004/0127939 A1 7/2004 Grey et al.
2004/0133249 A1 7/2004 Gesotti
2004/0167588 A1 8/2004 Bertolucci
2004/0249416 A1 12/2004 Yun et al.
2004/0267153 A1 12/2004 Bergethon
2004/0267331 A1 12/2004 Koeneman et al.
2005/0015042 A1 1/2005 Sun et al.
2005/0021103 A1 1/2005 DiLorenzo
2005/0055063 A1 3/2005 Loeb et al.
2005/0060009 A1 3/2005 Geotz
2005/0065553 A1 3/2005 Ben Ezra et al.
2005/0075502 A1 4/2005 Shafer
2005/0076909 A1 4/2005 Stahmann et al.
2005/0171576 A1 8/2005 Williams et al.
2005/0171577 A1 8/2005 Cohen et al.
2005/0182454 A1 8/2005 Gharib et al.
2005/0222626 A1 10/2005 DiLorenzo
2005/0234309 A1 10/2005 Klapper
2005/0240241 A1 10/2005 Yun et al.
2005/0257349 A1 11/2005 Bauer
2005/0261559 A1 11/2005 Mumford et al.
2006/0015153 A1 1/2006 Gliner et al.
2006/0047326 A1 3/2006 Wheeler
2006/0052726 A1 3/2006 Weisz et al.
2006/0074450 A1 4/2006 Boveja et al.
2006/0095088 A1 5/2006 De Ridder
2006/0161218 A1 7/2006 Danilov
2006/0173509 A1 8/2006 Lee et al.
2006/0184059 A1 8/2006 Jadidi
2006/0217781 A1 9/2006 John
2006/0224191 A1 10/2006 DiLorenzo
2006/0229678 A1 10/2006 Lee
2006/0253167 A1 11/2006 Kurtz et al.
2006/0276853 A1 12/2006 Tass
2006/0293723 A1 12/2006 Whitehurst et al.
2007/0027486 A1 2/2007 Armstrong
2007/0073361 A1 3/2007 Goren et al.
2007/0123951 A1 5/2007 Boston
2007/0123952 A1 5/2007 Strother et al.
2007/0142862 A1 6/2007 DiLorenzo
2007/0142874 A1 6/2007 John
2007/0156179 A1 7/2007 Karashurov
2007/0156182 A1 7/2007 Castel et al.
2007/0156183 A1 7/2007 Rhodes
2007/0156200 A1 7/2007 Kornet et al.
2007/0173899 A1 7/2007 Levin et al.
2007/0173903 A1 7/2007 Goren et al.
2007/0185409 A1 8/2007 Wu et al.
2007/0203533 A1 8/2007 Goren et al.
2007/0203534 A1 8/2007 Tapper
2007/0207193 A1 9/2007 Zasler et al.
2007/0249952 A1 10/2007 Rubin et al.
2007/0255319 A1 11/2007 Greenberg et al.
2007/0255323 A1 11/2007 Werder et al.
2007/0256284 A1 11/2007 Bauer
2007/0276217 A1 11/2007 Brown et al.
2007/0282228 A1 12/2007 Einav et al.
2007/0293917 A1 12/2007 Thompson et al.
2007/0294746 A1 12/2007 Sasakura et al.
2008/0004672 A1 1/2008 Dalal et al.
2008/0009772 A1 1/2008 Tyler et al.
2008/0021505 A1 1/2008 Hastings et al.
2008/0027507 A1 1/2008 Bijelic et al.
2008/0030170 A1* 2/2008 Dacquay ................. H02J 50/80
235/375
2008/0033259 A1 2/2008 Manto et al.
2008/0033504 A1 2/2008 Bertolucci
2008/0033510 A1 2/2008 Herregraven et al.
2008/0033511 A1 2/2008 Dobak
2008/0045775 A1 2/2008 Lozano
2008/0051839 A1 2/2008 Libbus et al.

(56) References Cited

U.S. PATENT DOCUMENTS

2008/0051845 A1 2/2008 Mentelos
2008/0058773 A1 3/2008 John
2008/0058871 A1 3/2008 Libbus et al.
2008/0058893 A1 3/2008 Noujokat
2008/0061961 A1 3/2008 John
2008/0091256 A1 4/2008 Libbus et al.
2008/0097564 A1 4/2008 Lathrop
2008/0147146 A1 6/2008 Wahlgren et al.
2008/0177398 A1 7/2008 Gross et al.
2008/0195007 A1 8/2008 Podrazhansky et al.
2008/0208282 A1 8/2008 Gelfand et al.
2008/0208288 A1 8/2008 Podrazhansky et al.
2008/0216593 A1 9/2008 Jacobsen et al.
2008/0243204 A1 10/2008 Uthman et al.
2008/0269593 A1 10/2008 Weinstock
2008/0288016 A1 11/2008 Amurthur et al.
2008/0300449 A1 12/2008 Gerber et al.
2008/0306325 A1 12/2008 Burnett et al.
2008/0312520 A1 12/2008 Rowlandson et al.
2009/0005713 A1 1/2009 Podrazhansky et al.
2009/0018609 A1 1/2009 DiLorenzo
2009/0049722 A1 2/2009 Chan
2009/0076565 A1 3/2009 Surwit
2009/0082831 A1 3/2009 Paul et al.
2009/0099623 A1 4/2009 Bentwich
2009/0105785 A1 4/2009 Wei et al.
2009/0112133 A1 4/2009 Deisseroth et al.
2009/0132018 A1 5/2009 DiUbaldi et al.
2009/0157138 A1 6/2009 Errico et al.
2009/0187121 A1 7/2009 Evans
2009/0216294 A1 8/2009 Ewing et al.
2009/0222053 A1 9/2009 Gaunt et al.
2009/0247910 A1 10/2009 Klapper
2009/0249617 A1 10/2009 Karicherla et al.
2009/0270952 A1 10/2009 Weinstock
2009/0299435 A1 12/2009 Gliner et al.
2009/0312690 A1 12/2009 Kim et al.
2009/0318986 A1 12/2009 Alo et al.
2009/0326595 A1 12/2009 Brockway et al.
2009/0326607 A1 12/2009 Castel et al.
2010/0004715 A1 1/2010 Fahey
2010/0010381 A1 1/2010 Skelton et al.
2010/0010383 A1 1/2010 Skelton et al.
2010/0010572 A1 1/2010 Skelton et al.
2010/0016929 A1 1/2010 Prochazka
2010/0030119 A1 2/2010 McNames et al.
2010/0036464 A1 2/2010 Picciano
2010/0057154 A1 3/2010 Dietrich et al.
2010/0059722 A1 3/2010 Copp-Howland et al.
2010/0072046 A1 3/2010 Maeda et al.
2010/0076533 A1 3/2010 Dar et al.
2010/0099963 A1 4/2010 Kilger
2010/0107657 A1 5/2010 Vistakula
2010/0125220 A1 5/2010 Seong
2010/0152623 A1 6/2010 Williams
2010/0152817 A1 6/2010 Gillbe
2010/0168501 A1 7/2010 Burnett et al.
2010/0168604 A1 7/2010 Echauz
2010/0174342 A1 7/2010 Boston et al.
2010/0202172 A1 8/2010 Skirda et al.
2010/0222629 A1 9/2010 Burnett et al.
2010/0222630 A1 9/2010 Mangrum et al.
2010/0227330 A1 9/2010 Fink et al.
2010/0228180 A1 9/2010 Jayes et al.
2010/0249637 A1 9/2010 Walter et al.
2010/0292527 A1 11/2010 Schneider et al.
2010/0298655 A1 11/2010 McCombie
2010/0298905 A1 11/2010 Simon
2010/0324611 A1 12/2010 Deming et al.
2011/0004268 A1 1/2011 Tcheng et al.
2011/0009920 A1 1/2011 Whitehurst et al.
2011/0021899 A1 1/2011 Arps et al.
2011/0040204 A1 2/2011 Ivorra et al.
2011/0040288 A1 2/2011 Eckstein et al.
2011/0054358 A1 3/2011 Kim et al.
2011/0071590 A1 3/2011 Mounaim et al.
2011/0082524 A1 4/2011 Thomas et al.
2011/0098780 A1 4/2011 Graupe et al.
2011/0112605 A1 5/2011 Fahey
2011/0118805 A1 5/2011 Wei et al.
2011/0125212 A1 5/2011 Tyler
2011/0137375 A1 6/2011 McBride
2011/0152968 A1 6/2011 Nathan et al.
2011/0184489 A1 7/2011 Nicolelis et al.
2011/0196446 A1 8/2011 Wu
2011/0202107 A1 8/2011 Sunagawa et al.
2011/0208444 A1 8/2011 Solinky
2011/0213278 A1 9/2011 Horak et al.
2011/0224571 A1 9/2011 Pascual-Leone et al.
2011/0230701 A1 9/2011 Simon et al.
2011/0245734 A1 10/2011 Wagner et al.
2011/0250297 A1 10/2011 Oronsky et al.
2011/0282412 A1 11/2011 Glukhovsky et al.
2011/0288615 A1 11/2011 Armstrong et al.
2011/0301663 A1 12/2011 Wang et al.
2011/0313327 A1 12/2011 Van Acht et al.
2012/0010492 A1 1/2012 Thramann et al.
2012/0035674 A1 2/2012 Weinstock
2012/0035680 A1 2/2012 Napadow
2012/0046535 A1 2/2012 Lin et al.
2012/0050298 A1 3/2012 Hoffman
2012/0053491 A1 3/2012 Nathan et al.
2012/0059298 A1 3/2012 Hoffman et al.
2012/0078319 A1 3/2012 De Ridder
2012/0088986 A1 4/2012 David et al.
2012/0092178 A1 4/2012 Callsen et al.
2012/0098493 A1 4/2012 Budike
2012/0101326 A1 4/2012 Simon et al.
2012/0101396 A1* 4/2012 Solosko ............... A61B 5/0006 600/509
2012/0109013 A1 5/2012 Everett et al.
2012/0136410 A1 5/2012 Rezai et al.
2012/0158094 A1 6/2012 Kramer et al.
2012/0184801 A1 7/2012 Simon et al.
2012/0185020 A1 7/2012 Simon et al.
2012/0186121 A1 7/2012 Hanssen et al.
2012/0203079 A1 8/2012 Mclaughlin
2012/0203245 A1 8/2012 Imabayashi et al.
2012/0211013 A1 8/2012 Otis
2012/0220812 A1 8/2012 Mishelevich
2012/0239112 A1 9/2012 Muraoka
2012/0245483 A1 9/2012 Lundqvist
2012/0259255 A1 10/2012 Tomlinson et al.
2012/0277621 A1 11/2012 Gerber et al.
2012/0289869 A1 11/2012 Tyler
2012/0290036 A1 11/2012 Karamanoglu et al.
2012/0302821 A1 11/2012 Burnett
2012/0303080 A1 11/2012 Ben-David et al.
2012/0310298 A1 12/2012 Besio et al.
2012/0310299 A1 12/2012 Norbert et al.
2012/0310303 A1 12/2012 Popovic et al.
2012/0330182 A1 12/2012 Alberts et al.
2013/0006322 A1 1/2013 Tai
2013/0035745 A1 2/2013 Ahmed et al.
2013/0046276 A1 2/2013 Mernoe et al.
2013/0053817 A1 2/2013 Yun et al.
2013/0060124 A1 3/2013 Zietsma
2013/0066388 A1 3/2013 Bernhard et al.
2013/0066393 A1 3/2013 Gross et al.
2013/0066395 A1 3/2013 Simon et al.
2013/0085317 A1 4/2013 Feinstein
2013/0090519 A1 4/2013 Tass
2013/0106684 A1* 5/2013 Weast ................ A63B 71/0622 345/156
2013/0116606 A1 5/2013 Cordo
2013/0123568 A1 5/2013 Hamilton et al.
2013/0123666 A1 5/2013 Giuffrida et al.
2013/0123684 A1 5/2013 Giuffrida et al.
2013/0131484 A1 5/2013 Pernu
2013/0131770 A1 5/2013 Rezai
2013/0150918 A1 6/2013 Peterson et al.
2013/0158624 A1 6/2013 Bain et al.
2013/0158627 A1 6/2013 Gozani et al.
2013/0178765 A1 7/2013 Mishelevich

(56) References Cited

U.S. PATENT DOCUMENTS

2013/0211471 A1 8/2013 Libbus et al.
2013/0231713 A1 9/2013 De Ridder et al.
2013/0236867 A1 9/2013 Avni et al.
2013/0238049 A1 9/2013 Simon et al.
2013/0245486 A1 9/2013 Simon et al.
2013/0245713 A1 9/2013 Tass
2013/0253299 A1 9/2013 Weber et al.
2013/0262298 A1 10/2013 Morley
2013/0267759 A1 10/2013 Jin
2013/0281890 A1 10/2013 Mishelevich
2013/0289647 A1 10/2013 Bhadra et al.
2013/0296967 A1 11/2013 Skaribas et al.
2013/0297022 A1 11/2013 Pathak
2013/0317565 A1 11/2013 Weinstock
2013/0331907 A1 12/2013 Sumners et al.
2013/0333094 A1 12/2013 Rogers et al.
2013/0338726 A1 12/2013 Machado
2014/0005743 A1 1/2014 Giuffrida et al.
2014/0025059 A1 1/2014 Kerr
2014/0031605 A1 1/2014 Schneider
2014/0039573 A1 2/2014 Jindra
2014/0039575 A1 2/2014 Bradley
2014/0046406 A1 2/2014 Ellrich et al.
2014/0046407 A1 2/2014 Ben-Ezra et al.
2014/0046423 A1 2/2014 Rajguru et al.
2014/0058189 A1 2/2014 Stubbeman
2014/0067003 A1 3/2014 Vase et al.
2014/0074179 A1 3/2014 Heldman et al.
2014/0074180 A1 3/2014 Giuffrida et al.
2014/0078694 A1 3/2014 Wissmar
2014/0081345 A1 3/2014 Hershey
2014/0081353 A1 3/2014 Cook et al.
2014/0094675 A1 4/2014 Luna et al.
2014/0094873 A1 4/2014 Emborg et al.
2014/0107542 A1 4/2014 Schubert et al.
2014/0114117 A1 4/2014 Naghavi et al.
2014/0128939 A1 5/2014 Embrey et al.
2014/0132410 A1 5/2014 Chang
2014/0142654 A1 5/2014 Simon et al.
2014/0148872 A1 5/2014 Goldwasser et al.
2014/0148873 A1 5/2014 Kirn
2014/0155799 A1* 6/2014 Skahan .............. A61N 1/37247
607/59
2014/0163444 A1 6/2014 Ingvarsson
2014/0171834 A1 6/2014 DeGoede et al.
2014/0180361 A1 6/2014 Burdick et al.
2014/0200573 A1 7/2014 Deem et al.
2014/0214119 A1 7/2014 Greiner et al.
2014/0228927 A1 8/2014 Ahmad et al.
2014/0236258 A1 8/2014 Carroll et al.
2014/0246628 A1 9/2014 Anhalt et al.
2014/0249452 A1 9/2014 Marsh et al.
2014/0257047 A1 9/2014 Sillay et al.
2014/0257129 A1 9/2014 Choi et al.
2014/0257141 A1 9/2014 Giuffrida et al.
2014/0276194 A1 9/2014 Osorio
2014/0277220 A1 9/2014 Brennan et al.
2014/0296752 A1 10/2014 Edgerton et al.
2014/0296934 A1 10/2014 Gozani et al.
2014/0296935 A1 10/2014 Ferree et al.
2014/0300490 A1 10/2014 Kotz et al.
2014/0309709 A1 10/2014 Gozanl et al.
2014/0316484 A1 10/2014 Edgerton et al.
2014/0324118 A1 10/2014 Simon et al.
2014/0330068 A1 11/2014 Partsch et al.
2014/0330335 A1 11/2014 Errico et al.
2014/0336003 A1 11/2014 Franz et al.
2014/0336722 A1 11/2014 Rocon De Lima et al.
2014/0336731 A1 11/2014 Weinstock
2014/0343462 A1 11/2014 Burnet
2014/0350436 A1 11/2014 Nathan et al.
2014/0358040 A1 12/2014 Kim et al.
2014/0364678 A1 12/2014 Harry et al.
2015/0004656 A1 1/2015 Tang et al.
2015/0005852 A1 1/2015 Hershey et al.
2015/0012067 A1 1/2015 Bradley et al.
2015/0018926 A1 1/2015 Frenkel et al.
2015/0026783 A1 1/2015 Tseng et al.
2015/0038886 A1 2/2015 Snow
2015/0042315 A1 2/2015 Cen et al.
2015/0044656 A1 2/2015 Eichhorn et al.
2015/0057506 A1 2/2015 Luna et al.
2015/0073310 A1 3/2015 Pracar et al.
2015/0080979 A1 3/2015 Lasko et al.
2015/0097617 A1 4/2015 Chak
2015/0100004 A1 4/2015 Goldman et al.
2015/0100104 A1 4/2015 Kiani et al.
2015/0100105 A1 4/2015 Kiani et al.
2015/0112404 A1 4/2015 Holding et al.
2015/0148865 A1* 5/2015 Gozani .............. A61N 1/36014
607/46
2015/0148866 A1 5/2015 Bulsen et al.
2015/0148878 A1 5/2015 Yoo et al.
2015/0157274 A1 6/2015 Ghassemzadeh et al.
2015/0163873 A1 6/2015 Kawai et al.
2015/0164377 A1 6/2015 Nathan et al.
2015/0164401 A1 6/2015 Toth et al.
2015/0190085 A1 7/2015 Nathan et al.
2015/0190634 A1 7/2015 Rezai et al.
2015/0196767 A1 7/2015 Zaghloul
2015/0202444 A1 7/2015 Franke et al.
2015/0208955 A1 7/2015 Smith
2015/0216475 A1 8/2015 Luna et al.
2015/0230733 A1 8/2015 Heo et al.
2015/0230756 A1 8/2015 Luna et al.
2015/0273234 A1 10/2015 Weinstock
2015/0277559 A1* 10/2015 Vescovi .................. G06F 3/017
345/173
2015/0290463 A1 10/2015 Yonce
2015/0297901 A1 10/2015 Kockx
2015/0321000 A1 11/2015 Rosenbluth et al.
2015/0335882 A1 11/2015 Gross
2015/0360030 A1 12/2015 Cartledge et al.
2016/0001096 A1 1/2016 Mishelevich
2016/0008620 A1 1/2016 Stubbeman
2016/0016014 A1 1/2016 Wagner et al.
2016/0022987 A1 1/2016 Zschaeck et al.
2016/0022989 A1 1/2016 Pfeifer
2016/0038059 A1 2/2016 Asada et al.
2016/0039239 A1 2/2016 Ward et al.
2016/0045140 A1 2/2016 Kitamura et al.
2016/0082253 A1 3/2016 Moffitt et al.
2016/0089045 A1 3/2016 Sadeghian-Motahar et al.
2016/0106344 A1 4/2016 Nazari
2016/0120432 A1 5/2016 Sridhar et al.
2016/0121110 A1 5/2016 Kent et al.
2016/0128621 A1 5/2016 Machado et al.
2016/0129248 A1 5/2016 Creasey et al.
2016/0144186 A1 5/2016 Kaemmerer et al.
2016/0156261 A1 6/2016 Kaneda
2016/0157735 A1 6/2016 Zhang
2016/0158542 A1 6/2016 Ahmed
2016/0158565 A1 6/2016 Lee
2016/0198998 A1 7/2016 Rahimi et al.
2016/0213924 A1 7/2016 Coleman et al.
2016/0220836 A1 8/2016 Parks
2016/0233034 A1 8/2016 Sheng
2016/0242656 A1 8/2016 Jackson et al.
2016/0256689 A1 9/2016 Vallejo et al.
2016/0262685 A1 9/2016 Wagner et al.
2016/0263376 A1 9/2016 Yoo et al.
2016/0279435 A1 9/2016 Hyde et al.
2016/0287879 A1 10/2016 Denison et al.
2016/0336722 A1 11/2016 Taxter
2016/0339239 A1 11/2016 Yoo et al.
2016/0361540 A9 12/2016 Simon et al.
2016/0375249 A1 12/2016 Bonnet et al.
2017/0014625 A1 1/2017 Rosenbluth et al.
2017/0027812 A1 2/2017 Hyde et al.
2017/0036025 A1 2/2017 Sachs et al.
2017/0042467 A1 2/2017 Herr et al.
2017/0055880 A1 3/2017 Agrawal et al.
2017/0056238 A1 3/2017 Yi et al.
2017/0056643 A1 3/2017 Herb et al.

(56) References Cited

U.S. PATENT DOCUMENTS

| | | | |
|---|---|---|---|
| 2017/0079597 | A1 | 3/2017 | Horne |
| 2017/0080207 | A1 | 3/2017 | Perez et al. |
| 2017/0087364 | A1 | 3/2017 | Cartledge et al. |
| 2017/0095667 | A1 | 4/2017 | Yakovlev et al. |
| 2017/0113045 | A1 | 4/2017 | Baldassano et al. |
| 2017/0132067 | A1 | 5/2017 | Singaravelu Vanaja et al. |
| 2017/0157398 | A1 | 6/2017 | Wong et al. |
| 2017/0165485 | A1 | 6/2017 | Sullivan et al. |
| 2017/0224991 | A1 | 8/2017 | Wingeier et al. |
| 2017/0239415 | A1 | 8/2017 | Hwang et al. |
| 2017/0246481 | A1 | 8/2017 | Mishelevich |
| 2017/0259061 | A1 | 9/2017 | Simon et al. |
| 2017/0266443 | A1 | 9/2017 | Rajguru et al. |
| 2017/0274208 | A1 | 9/2017 | Nagel et al. |
| 2017/0287146 | A1 | 10/2017 | Pathak et al. |
| 2017/0312505 | A1 | 11/2017 | Ahmed |
| 2017/0312512 | A1 | 11/2017 | Creasey et al. |
| 2017/0312513 | A1 | 11/2017 | Hershey et al. |
| 2017/0361093 | A1 | 12/2017 | Yoo et al. |
| 2017/0368329 | A1 | 12/2017 | Tyler et al. |
| 2018/0001086 | A1 | 1/2018 | Bartholomew et al. |
| 2018/0001088 | A1 | 1/2018 | Tass |
| 2018/0021576 | A1 | 1/2018 | Wong et al. |
| 2018/0028809 | A1 | 2/2018 | Ziv |
| 2018/0028841 | A1 | 2/2018 | Konofagou et al. |
| 2018/0036535 | A1 | 2/2018 | Wong et al. |
| 2018/0042654 | A1 | 2/2018 | Ingvarsson et al. |
| 2018/0049676 | A1 | 2/2018 | Griffiths et al. |
| 2018/0064344 | A1 | 3/2018 | Nguyen |
| 2018/0064362 | A1 | 3/2018 | Hennings et al. |
| 2018/0064944 | A1 | 3/2018 | Grill et al. |
| 2018/0116546 | A1 | 5/2018 | Pastoor et al. |
| 2018/0132757 | A1 | 5/2018 | Kong et al. |
| 2018/0140842 | A1 | 5/2018 | Olaighin et al. |
| 2018/0168905 | A1 | 6/2018 | Goodall et al. |
| 2018/0169400 | A1 | 6/2018 | Wong et al. |
| 2018/0199841 | A1 | 7/2018 | Yang et al. |
| 2018/0214694 | A1 | 8/2018 | Parramon |
| 2018/0221620 | A1 | 8/2018 | Metzger |
| 2018/0235500 | A1 | 8/2018 | Lee et al. |
| 2018/0236217 | A1 | 8/2018 | Hamner et al. |
| 2018/0264263 | A1 | 9/2018 | Rosenbluth et al. |
| 2018/0289965 | A1 | 10/2018 | Nelson et al. |
| 2018/0345020 | A1 | 12/2018 | Ironi et al. |
| 2018/0361153 | A1 | 12/2018 | Giuffrida et al. |
| 2019/0001117 | A1 | 1/2019 | Ben-David et al. |
| 2019/0001129 | A1 | 1/2019 | Rosenbluth et al. |
| 2019/0001139 | A1 | 1/2019 | Mishra et al. |
| 2019/0126047 | A1 | 5/2019 | Kassiri Bidhendi et al. |
| 2019/0134393 | A1 | 5/2019 | Wong et al. |
| 2019/0143098 | A1 | 5/2019 | Kaplan et al. |
| 2019/0143111 | A1 | 5/2019 | Hamner et al. |
| 2019/0143113 | A1 | 5/2019 | Wong et al. |
| 2019/0167976 | A1 | 6/2019 | Byers et al. |
| 2019/0229727 | A1 | 7/2019 | Krishna |
| 2019/0269914 | A1 | 9/2019 | Moaddeb et al. |
| 2019/0298998 | A1 | 10/2019 | Coleman et al. |
| 2019/0299008 | A1 | 10/2019 | Rao |
| 2019/0321636 | A1 | 10/2019 | Law |
| 2019/0343462 | A1 | 11/2019 | Grant et al. |
| 2019/0374771 | A1 | 12/2019 | Simon et al. |
| 2020/0023183 | A1 | 1/2020 | Ollerenshaw et al. |
| 2020/0038654 | A1 | 2/2020 | Doskocil et al. |
| 2020/0046968 | A1 | 2/2020 | Herr et al. |
| 2020/0061378 | A1 | 2/2020 | Ganguly et al. |
| 2020/0069947 | A1 | 3/2020 | Kent |
| 2020/0077943 | A1 | 3/2020 | Weinstock |
| 2020/0093400 | A1 | 3/2020 | Hamner et al. |
| 2020/0139118 | A1 | 5/2020 | John et al. |
| 2020/0147373 | A1 | 5/2020 | Tamaki et al. |
| 2020/0155847 | A1 | 5/2020 | Perez |
| 2020/0171269 | A1 | 6/2020 | Hooper et al. |
| 2020/0171304 | A1 | 6/2020 | Simon et al. |
| 2020/0179687 | A1 | 6/2020 | Wong et al. |
| 2020/0197707 | A1 | 6/2020 | Covalin |
| 2020/0204164 | A1 | 6/2020 | Nishiyama |
| 2020/0215324 | A1 | 7/2020 | Mantovani et al. |
| 2020/0221975 | A1 | 7/2020 | Basta et al. |
| 2020/0246617 | A1 | 8/2020 | Errico et al. |
| 2020/0254247 | A1 | 8/2020 | Brezel et al. |
| 2020/0254251 | A1 | 8/2020 | Wong et al. |
| 2020/0269046 | A1 | 8/2020 | Page et al. |
| 2020/0276442 | A1 | 9/2020 | Owen |
| 2020/0282201 | A1 | 9/2020 | Doskocil |
| 2020/0289813 | A1 | 9/2020 | Ito et al. |
| 2020/0289814 | A1 | 9/2020 | Hamner et al. |
| 2020/0297999 | A1 | 9/2020 | Pal |
| 2020/0316379 | A1 | 10/2020 | Yoo et al. |
| 2020/0324104 | A1 | 10/2020 | Labuschagne et al. |
| 2020/0338348 | A1 | 10/2020 | Honeycutt et al. |
| 2020/0346008 | A1 | 11/2020 | Song |
| 2020/0367775 | A1 | 11/2020 | Buckley et al. |
| 2020/0405188 | A1 | 12/2020 | Sharma et al. |
| 2020/0406022 | A1 | 12/2020 | Sharma et al. |
| 2021/0008369 | A1 | 1/2021 | Crosson |
| 2021/0016079 | A1 | 1/2021 | Ekelem et al. |
| 2021/0016089 | A1 | 1/2021 | Crosson |
| 2021/0023376 | A1 | 1/2021 | Hareland et al. |
| 2021/0031026 | A1 | 2/2021 | Simon et al. |
| 2021/0031036 | A1 | 2/2021 | Sharma et al. |
| 2021/0052883 | A1 | 2/2021 | Wong et al. |
| 2021/0052897 | A1 | 2/2021 | Bhadra et al. |
| 2021/0052900 | A1 | 2/2021 | Pepin et al. |
| 2021/0060337 | A1 | 3/2021 | Wybo et al. |
| 2021/0069507 | A1 | 3/2021 | Gozani et al. |
| 2021/0085974 | A1 | 3/2021 | Bouton et al. |
| 2021/0085976 | A1 | 3/2021 | Heldman et al. |
| 2021/0099867 | A1 | 4/2021 | Brown et al. |
| 2021/0100999 | A1 | 4/2021 | Rosenbluth et al. |
| 2021/0101007 | A1 | 4/2021 | Hamner et al. |
| 2021/0113834 | A1 | 4/2021 | Wong et al. |
| 2021/0128906 | A1 | 5/2021 | Perez et al. |
| 2021/0162212 | A1 | 6/2021 | Kern et al. |
| 2021/0169684 | A1 | 6/2021 | Black et al. |
| 2021/0187279 | A1 | 6/2021 | Bouton et al. |
| 2021/0205619 | A1 | 7/2021 | Wong et al. |
| 2021/0212230 | A1 | 7/2021 | Hsu et al. |
| 2021/0213283 | A1 | 7/2021 | Yoo et al. |
| 2021/0220650 | A1 | 7/2021 | Kassiri Bidhendi et al. |
| 2021/0244940 | A1 | 8/2021 | Liberatore et al. |
| 2021/0244950 | A1 | 8/2021 | Ironi et al. |
| 2021/0248893 | A1 | 8/2021 | Van Dinther |
| 2021/0252278 | A1 | 8/2021 | Hamner et al. |
| 2021/0252279 | A1 | 8/2021 | Kong et al. |
| 2021/0260379 | A1 | 8/2021 | Charlesworth et al. |
| 2021/0266011 | A1 | 8/2021 | Chen et al. |
| 2021/0283400 | A1 | 9/2021 | Hamner et al. |
| 2021/0289814 | A1 | 9/2021 | Roubos-van den Hil et al. |
| 2021/0299445 | A1 | 9/2021 | Rajguru et al. |
| 2021/0308460 | A1 | 10/2021 | Wong et al. |
| 2021/0330547 | A1 | 10/2021 | Moaddeb et al. |
| 2021/0330974 | A1 | 10/2021 | Wong et al. |
| 2021/0353181 | A1 | 11/2021 | Roh |
| 2021/0379374 | A1 | 12/2021 | Hamner et al. |
| 2021/0379379 | A1 | 12/2021 | Campean et al. |
| 2021/0402172 | A1 | 12/2021 | Ross et al. |
| 2022/0001164 | A1 | 1/2022 | Sharma et al. |
| 2022/0016413 | A1 | 1/2022 | John et al. |
| 2022/0031245 | A1 | 2/2022 | Bresler |
| 2022/0054820 | A1 | 2/2022 | Turner |
| 2022/0054831 | A1 | 2/2022 | McBride |
| 2022/0080196 | A1 | 3/2022 | Crosson |
| 2022/0088373 | A1 | 3/2022 | Burnett |
| 2022/0126095 | A1 | 4/2022 | Rajguru et al. |
| 2022/0134104 | A1 | 5/2022 | Elyahoodayan et al. |
| 2022/0143391 | A1 | 5/2022 | Vaishya et al. |
| 2022/0143392 | A1 | 5/2022 | Labuschagne et al. |
| 2022/0143393 | A1 | 5/2022 | Charlesworth et al. |
| 2022/0143402 | A1 | 5/2022 | Oppenheim et al. |
| 2022/0203091 | A1 | 6/2022 | Vysokov |
| 2022/0212007 | A1 | 7/2022 | Rajguru et al. |
| 2022/0218991 | A1 | 7/2022 | Moaddeb et al. |
| 2022/0220276 | A1 | 7/2022 | Ziebell et al. |
| 2022/0233860 | A1 | 7/2022 | Hamner et al. |

(56) References Cited

U.S. PATENT DOCUMENTS

2022/0266011 A1 8/2022 Hamner et al.
2022/0266012 A1 8/2022 Hamner et al.
2022/0273938 A1 9/2022 Chen
2022/0287616 A1 9/2022 Dundovic et al.
2022/0323745 A1 10/2022 Staats et al.
2022/0347461 A1 11/2022 Campean et al.
2022/0370786 A1 11/2022 Atkin et al.
2022/0370802 A1 11/2022 Tracey et al.
2022/0387793 A1 12/2022 Song et al.
2022/0401721 A1 12/2022 Jackson et al.
2022/0409404 A1 12/2022 Yang et al.
2023/0001205 A1 1/2023 Aprasoff
2023/0009158 A1 1/2023 Liberatore
2023/0010696 A1 1/2023 Pradeep
2023/0026037 A1 1/2023 Larraya et al.
2023/0062326 A1 3/2023 Colachis et al.
2023/0074017 A1 3/2023 Pan
2023/0075750 A1 3/2023 Pan
2023/0080790 A1 3/2023 Crosson et al.
2023/0086004 A1 3/2023 Yang et al.
2023/0110185 A1 4/2023 Mantovani et al.
2023/0146449 A1 5/2023 Muse et al.
2023/0148956 A1 5/2023 Narayanan et al.
2023/0172542 A1 6/2023 Baker et al.
2023/0191115 A1 6/2023 Blum et al.
2023/0191126 A1 6/2023 Kent et al.
2023/0200732 A1 6/2023 Ye et al.
2023/0201584 A1 6/2023 Rajguru et al.
2023/0207232 A1 6/2023 Ye et al.
2023/0218897 A1 7/2023 Wang et al.
2023/0230669 A1 7/2023 Jung
2023/0233855 A1 7/2023 Sunkeri et al.
2023/0241393 A1 8/2023 Suri et al.
2023/0248962 A1 8/2023 Zhang et al.
2023/0256245 A1 8/2023 Crosson
2023/0277091 A1 9/2023 Blanco
2023/0277109 A1 9/2023 Blum et al.
2023/0277838 A1 9/2023 Errico et al.
2023/0277841 A1 9/2023 Wang et al.
2023/0285743 A1 9/2023 Muccio
2023/0293882 A1 9/2023 Howe
2023/0321430 A1 10/2023 Ye et al.
2023/0321436 A1 10/2023 Tass
2023/0321437 A1 10/2023 Nemechek
2023/0337944 A1 10/2023 Szmulewicz et al.
2023/0338225 A1 10/2023 Carballo et al.
2023/0363711 A1 11/2023 Theodore et al.
2023/0371846 A1 11/2023 Sharma et al.
2023/0381505 A1 11/2023 Gozani et al.
2023/0381545 A1 11/2023 Carballo et al.
2023/0397833 A1 12/2023 Tognetti et al.
2024/0001120 A1 1/2024 Napadow et al.
2024/0032819 A1 2/2024 Zhao et al.
2024/0042203 A1 2/2024 Gill et al.
2024/0050308 A1 2/2024 Carballo et al.
2024/0058606 A1 2/2024 Law et al.
2024/0062890 A1 2/2024 Shin et al.
2024/0065617 A1 2/2024 Choi
2024/0066286 A1 2/2024 Yin et al.
2024/0066287 A1 2/2024 Siff
2024/0090600 A1 3/2024 Colachis et al.
2024/0091533 A1 3/2024 Ziv et al.
2024/0108239 A1 4/2024 Crosson et al.
2024/0122797 A1 4/2024 Moaddeb et al.
2024/0123223 A1 4/2024 Charlesworth et al.
2024/0123226 A1 4/2024 Raymondos
2024/0123227 A1 4/2024 Charlesworth et al.
2024/0123230 A1 4/2024 Raghunathan
2024/0149063 A1 5/2024 Leuthardt et al.
2024/0156674 A1 5/2024 Carballo et al.
2024/0156675 A1 5/2024 Carballo et al.
2024/0157142 A1 5/2024 Yeniel et al.
2024/0189538 A1 6/2024 Bamber
2024/0189594 A1 6/2024 Hamner et al.
2024/0189596 A1 6/2024 Mech et al.
2024/0197200 A1 6/2024 Thorp et al.
2024/0197204 A1 6/2024 Jung et al.
2024/0197237 A1 6/2024 Hamner et al.
2024/0207618 A1 6/2024 Baker et al.
2024/0226550 A1 7/2024 Moaddeb et al.
2024/0245388 A1 7/2024 Plunger
2024/0245905 A1 7/2024 Fitzgerald
2024/0252824 A1 8/2024 Verzal et al.
2024/0285941 A1 8/2024 Raymondos
2024/0285951 A1 8/2024 Huynh et al.
2024/0293669 A1 9/2024 Kostopoulos
2024/0293670 A1 9/2024 Kostopoulos
2024/0293674 A1 9/2024 Shelton et al.
2024/0299734 A1 9/2024 Wang et al.
2024/0299735 A1 9/2024 Wang et al.
2024/0316339 A1 9/2024 Keefer et al.
2024/0325727 A1 10/2024 Hamner et al.
2024/0325728 A1 10/2024 Schulte et al.
2024/0335654 A1 10/2024 Schulte et al.
2024/0350805 A1 10/2024 Kent
2024/0366935 A1 11/2024 Olofsson et al.
2024/0374208 A1 11/2024 Zaphrir et al.
2024/0386553 A1 11/2024 Akakin et al.
2024/0399148 A1 12/2024 Leuthardt et al.
2024/0406000 A1 12/2024 Nguyen et al.
2024/0408382 A1 12/2024 Shin et al.
2024/0416110 A1 12/2024 Kim
2024/0428429 A1 12/2024 Akakin et al.
2025/0001193 A1 1/2025 Müller-Bruhn
2025/0010061 A1 1/2025 John et al.
2025/0010068 A1 1/2025 Carballo et al.
2025/0010078 A1 1/2025 Netoff et al.
2025/0017518 A1 1/2025 Shah et al.
2025/0017815 A1 1/2025 Carballo et al.
2025/0018185 A1 1/2025 Ye et al.
2025/0032789 A1 1/2025 David
2025/0037595 A1 1/2025 Carballo et al.
2025/0037880 A1 1/2025 Pepin
2025/0041597 A1 2/2025 Tyler et al.
2025/0058101 A1 2/2025 Kong
2025/0058106 A1 2/2025 Simon et al.
2025/0065114 A1 2/2025 Crosson et al.
2025/0065117 A1 2/2025 Charlesworth et al.
2025/0068737 A1 2/2025 Keith et al.
2025/0082924 A1 3/2025 Simon et al.
2025/0099019 A1 3/2025 Muhammed et al.
2025/0114608 A1 4/2025 Haddock et al.
2025/0128058 A1 4/2025 Hamner et al.
2025/0128059 A1 4/2025 Rigot et al.
2025/0135189 A1 5/2025 Wong et al.
2025/0135199 A1 5/2025 Evans et al.
2025/0135200 A1 5/2025 Wong et al.
2025/0144405 A1 5/2025 Jackson et al.
2025/0144415 A1 5/2025 Vaishya et al.
2025/0161663 A1 5/2025 Rosenbluth et al.
2025/0161664 A1 5/2025 Wong et al.
2025/0161665 A1 5/2025 Liberatore et al.
2025/0161678 A1 5/2025 Rodriguez et al.
2025/0161684 A1 5/2025 Hamner et al.
2025/0161685 A1 5/2025 Hamner et al.
2025/0170399 A1 5/2025 Wong et al.
2025/0195877 A1 6/2025 Schulte et al.
2025/0205464 A1 6/2025 Bradley et al.
2025/0222256 A1 7/2025 Cardasis et al.
2025/0222261 A1 7/2025 Elyahoodayan et al.
2025/0235690 A1 7/2025 Jeffrey et al.
2025/0242150 A1 7/2025 Bouton et al.
2025/0248641 A1 8/2025 Mase
2025/0249244 A1 8/2025 Keenan
2025/0262430 A1 8/2025 Ross et al.
2025/0268783 A1 8/2025 Carballo et al.
2025/0269184 A1 8/2025 Shelton et al.
2025/0281309 A1 9/2025 Benigni et al.
2025/0281347 A1 9/2025 Francois et al.
2025/0281349 A1 9/2025 Carballo et al.
2025/0281735 A1 9/2025 Yang
2025/0295319 A1 9/2025 Tognetti et al.
2025/0319311 A1 10/2025 Sharma et al.
2025/0325815 A1 10/2025 Mazanec et al.

(56) References Cited

U.S. PATENT DOCUMENTS

| | | | |
|---|---|---|---|
| 2025/0332415 | A1 | 10/2025 | Kent et al. |
| 2025/0339671 | A1 | 11/2025 | Wong et al. |
| 2025/0339672 | A1 | 11/2025 | Wong et al. |
| 2025/0339685 | A1 | 11/2025 | Wong et al. |
| 2025/0345593 | A1 | 11/2025 | Rosenbluth et al. |
| 2025/0345594 | A1 | 11/2025 | Rosenbluth et al. |
| 2025/0352799 | A1 | 11/2025 | Soykan et al. |
| 2025/0352800 | A1 | 11/2025 | Soykan et al. |
| 2025/0352801 | A1 | 11/2025 | Soykan et al. |
| 2025/0352815 | A1 | 11/2025 | Martinez et al. |
| 2025/0352855 | A1 | 11/2025 | Dirkes et al. |
| 2025/0359806 | A1 | 11/2025 | Dundovic |
| 2025/0367457 | A1 | 12/2025 | Moore et al. |
| 2025/0375134 | A1 | 12/2025 | Chen |
| 2025/0375612 | A1 | 12/2025 | Wong et al. |
| 2025/0380891 | A1 | 12/2025 | Buckley et al. |
| 2025/0381397 | A1 | 12/2025 | Gill et al. |
| 2025/0381398 | A1 | 12/2025 | McNutt |
| 2026/0000891 | A1 | 1/2026 | Yang |
| 2026/0007354 | A1 | 1/2026 | Yang |
| 2026/0007357 | A1 | 1/2026 | Sobel et al. |
| 2026/0021301 | A1 | 1/2026 | Rosenbluth et al. |
| 2026/0027364 | A1 | 1/2026 | Tucker |
| 2026/0041910 | A1 | 2/2026 | Ollis |
| 2026/0048263 | A1 | 2/2026 | Covalin et al. |
| 2026/0076608 | A1 | 3/2026 | Dundovic et al. |
| 2026/0077180 | A1 | 3/2026 | Rosenbluth et al. |
| 2026/0077181 | A1 | 3/2026 | Rosenbluth et al. |
| 2026/0115455 | A1 | 4/2026 | Rosenbluth et al. |
| 2026/0115461 | A1 | 4/2026 | Balbaky et al. |
| 2026/0115466 | A1 | 4/2026 | Wong et al. |

FOREIGN PATENT DOCUMENTS

| | | |
|---|---|---|
| CN | 1826154 | 8/2006 |
| CN | 101022849 | 8/2007 |
| CN | 101115524 | 1/2008 |
| CN | 101365373 | 2/2009 |
| CN | 101612043 | 12/2009 |
| CN | 101687093 | 3/2010 |
| CN | 101801453 | 8/2010 |
| CN | 102089031 | 6/2011 |
| CN | 102481394 | 5/2012 |
| CN | 102905757 | 1/2013 |
| CN | 202724457 | 2/2013 |
| CN | 103517732 | 1/2014 |
| CN | 103608069 | 2/2014 |
| CN | 103889503 | 6/2014 |
| CN | 104144729 | 11/2014 |
| CN | 104168951 | 11/2014 |
| CN | 104436431 | 3/2015 |
| CN | 104519960 | 4/2015 |
| CN | 104939815 | 9/2015 |
| CN | 105457158 | 4/2016 |
| CN | 105848710 | 8/2016 |
| CN | 106413805 | 2/2017 |
| CN | 106687161 | 5/2017 |
| CN | 106794347 | 5/2017 |
| CN | 206434707 U | 8/2017 |
| CN | 107949421 | 4/2018 |
| CN | 108697890 | 10/2018 |
| CN | 108778411 | 11/2018 |
| CN | 109689151 | 4/2019 |
| CN | 111358461 | 7/2020 |
| CN | 118022172 | 2/2024 |
| CN | 117679641 | 3/2024 |
| CN | 118320302 | 7/2024 |
| CN | 222488608 U | 2/2025 |
| CN | 120114759 | 6/2025 |
| DE | 10 2008042373 | 4/2010 |
| DE | 10 2009004011 | 7/2010 |
| EP | 0000759 | 2/1979 |
| EP | 0801957 | 10/1997 |
| EP | 0725665 | 1/1998 |
| EP | 1062988 | 12/2000 |
| EP | 1558333 | 5/2007 |
| EP | 1727591 | 4/2009 |
| EP | 2383014 | 11/2011 |
| EP | 2291115 | 9/2013 |
| EP | 2801389 | 11/2014 |
| EP | 2892418 | 7/2015 |
| EP | 2892419 | 7/2015 |
| EP | 2892613 | 7/2015 |
| EP | 3020448 | 5/2016 |
| EP | 2948043 | 12/2016 |
| EP | 2029222 | 3/2017 |
| EP | 2780073 | 9/2017 |
| EP | 1951365 | 10/2017 |
| EP | 3154627 | 4/2018 |
| EP | 2827771 | 5/2018 |
| EP | 3184143 | 7/2018 |
| EP | 3075412 | 12/2018 |
| EP | 2691149 | 2/2019 |
| EP | 3349712 | 7/2019 |
| EP | 2790777 | 9/2019 |
| EP | 2734110 | 3/2020 |
| EP | 3503960 | 3/2020 |
| EP | 2667934 | 5/2020 |
| EP | 3650077 | 5/2020 |
| EP | 3113684 | 7/2020 |
| EP | 3352846 | 7/2020 |
| EP | 3337557 | 8/2020 |
| EP | 3493874 | 8/2020 |
| EP | 3409200 | 9/2020 |
| EP | 3701865 | 9/2020 |
| EP | 3427793 | 11/2020 |
| EP | 3212277 | 12/2020 |
| EP | 3436140 | 1/2021 |
| EP | 3758595 | 1/2021 |
| EP | 3261710 | 3/2021 |
| EP | 3641876 | 4/2021 |
| EP | 3679979 | 6/2021 |
| EP | 3841967 | 6/2021 |
| EP | 3402404 | 7/2021 |
| EP | 3562541 | 7/2021 |
| EP | 3453423 | 8/2021 |
| EP | 3675795 | 8/2021 |
| EP | 3648832 | 11/2021 |
| EP | 3100765 | 1/2022 |
| EP | 3693053 | 1/2022 |
| EP | 2741813 | 3/2022 |
| EP | 3399912 | 4/2022 |
| EP | 3558446 | 8/2022 |
| EP | 2714188 | 12/2022 |
| EP | 3487578 | 12/2022 |
| EP | 4108292 | 12/2022 |
| EP | 4119038 | 1/2023 |
| EP | 2967415 | 5/2023 |
| EP | 3326688 | 6/2023 |
| EP | 3378462 | 6/2023 |
| EP | 3784337 | 6/2023 |
| EP | 3870270 | 8/2023 |
| EP | 4233990 | 8/2023 |
| EP | 3541279 | 9/2023 |
| EP | 3989907 | 10/2023 |
| EP | 3990105 | 10/2023 |
| EP | 4171469 | 10/2023 |
| EP | 3600011 | 11/2023 |
| EP | 3996807 | 11/2023 |
| EP | 4010063 | 11/2023 |
| EP | 3461530 | 1/2024 |
| EP | 3463550 | 3/2024 |
| EP | 3565631 | 4/2024 |
| EP | 4115942 | 4/2024 |
| EP | 4356952 | 4/2024 |
| EP | 3842094 | 5/2024 |
| EP | 4061472 | 7/2024 |
| EP | 3990098 | 8/2024 |
| EP | 3784336 | 11/2024 |
| EP | 4556056 | 5/2025 |
| EP | 4433151 | 6/2025 |
| EP | 4578487 | 7/2025 |
| EP | 4241675 | 11/2025 |
| EP | 4659795 | 12/2025 |

(56) References Cited

FOREIGN PATENT DOCUMENTS

| | | |
|---|---|---|
| ES | 2222819 | 3/2006 |
| ES | 2272137 | 6/2008 |
| GB | 2496449 | 5/2013 |
| JP | 2010-527256 | 1/1900 |
| JP | 2002-200178 | 7/2002 |
| JP | 2003-501207 | 1/2003 |
| JP | 2003-533299 | 11/2003 |
| JP | 2004-512104 | 4/2004 |
| JP | 2006-503658 | 2/2006 |
| JP | 2008-018235 | 1/2008 |
| JP | 2009-034328 | 2/2009 |
| JP | 2009-512516 | 3/2009 |
| JP | 2009-529352 | 8/2009 |
| JP | 2010-506618 | 3/2010 |
| JP | 2010-512926 | 4/2010 |
| JP | 2010-246745 | 11/2010 |
| JP | 2012-005596 | 1/2012 |
| JP | 2012-055650 | 3/2012 |
| JP | 2012-217565 | 11/2012 |
| JP | 2013-017609 | 1/2013 |
| JP | 2013-094305 | 5/2013 |
| JP | 5439921 | 3/2014 |
| JP | 2015-514460 | 5/2015 |
| JP | 2016-511651 | 4/2016 |
| JP | 2018-038597 | 3/2018 |
| JP | 2018-516702 | 6/2018 |
| KR | 20130104446 | 9/2013 |
| WO | WO 1987/01024 | 2/1987 |
| WO | WO 1994/000187 | 1/1994 |
| WO | WO 1994/017855 | 8/1994 |
| WO | WO 95/19804 | 7/1995 |
| WO | WO 1996/032909 | 10/1996 |
| WO | WO 98/23326 | 6/1998 |
| WO | WO 98/40121 | 9/1998 |
| WO | WO 1998/043700 | 10/1998 |
| WO | WO 1999/019019 | 4/1999 |
| WO | WO 2000/015293 | 3/2000 |
| WO | WO 2000/076436 | 12/2000 |
| WO | WO 01/03768 | 1/2001 |
| WO | WO 2001/087411 | 11/2001 |
| WO | WO 2002/017987 | 3/2002 |
| WO | WO 2002/034327 | 5/2002 |
| WO | WO 03/015866 | 2/2003 |
| WO | WO 2004/037344 | 5/2004 |
| WO | WO 2004/067087 | 8/2004 |
| WO | WO 2004/108209 | 12/2004 |
| WO | WO 2005/007029 | 5/2005 |
| WO | WO 2005/105201 | 11/2005 |
| WO | WO 2005/0122894 | 12/2005 |
| WO | WO 2006/021820 | 3/2006 |
| WO | WO 2006/044793 | 4/2006 |
| WO | WO 2006/054118 | 5/2006 |
| WO | WO 2006/092007 | 9/2006 |
| WO | WO 2006/102724 | 10/2006 |
| WO | WO 2007/056493 | 5/2007 |
| WO | WO 2007/092290 | 8/2007 |
| WO | WO 2007/112092 | 10/2007 |
| WO | WO 2008/005478 | 1/2008 |
| WO | WO 2008/045598 | 4/2008 |
| WO | WO 2008/062395 | 5/2008 |
| WO | WO 2008/106174 | 9/2008 |
| WO | WO 2008/150591 | 12/2008 |
| WO | WO 2009/005797 | 1/2009 |
| WO | WO 2009/153730 | 12/2009 |
| WO | WO 2010/014260 | 2/2010 |
| WO | WO 2010/031055 | 3/2010 |
| WO | WO 2010/111321 | 9/2010 |
| WO | WO 2010/141155 | 12/2010 |
| WO | WO 2011/106225 | 9/2011 |
| WO | WO 2011/119224 | 9/2011 |
| WO | WO 2011/144883 | 11/2011 |
| WO | WO 2011/149656 | 12/2011 |
| WO | WO 2012/040243 | 3/2012 |
| WO | WO 2012/074794 | 6/2012 |
| WO | WO 2012166860 | 12/2012 |
| WO | WO 2013012625 | 1/2013 |
| WO | WO 2013/071307 | 5/2013 |
| WO | WO 2013/074809 | 5/2013 |
| WO | WO 2013/173727 | 11/2013 |
| WO | WO 2014/043757 | 3/2014 |
| WO | WO 2014040007 | 3/2014 |
| WO | WO 2014040018 | 3/2014 |
| WO | WO 2014040023 | 3/2014 |
| WO | WO 2014/053041 | 4/2014 |
| WO | WO 2014055507 | 4/2014 |
| WO | WO 2014/070999 | 5/2014 |
| WO | WO 2014/089549 | 6/2014 |
| WO | WO 2014/093964 | 6/2014 |
| WO | WO 2014/113813 | 7/2014 |
| WO | WO 2014/146082 | 9/2014 |
| WO | WO 2014/151431 | 9/2014 |
| WO | WO 2014/153201 | 9/2014 |
| WO | WO 2014138022 | 9/2014 |
| WO | WO 2014/207512 | 12/2014 |
| WO | WO 2015/033152 | 3/2015 |
| WO | WO 2015/039206 | 3/2015 |
| WO | WO 2015/039244 | 3/2015 |
| WO | WO 2015/042365 | 3/2015 |
| WO | WO 2015/079319 | 6/2015 |
| WO | WO 2015/085880 | 6/2015 |
| WO | WO 2015/095880 | 6/2015 |
| WO | WO 2015/128090 | 9/2015 |
| WO | WO 2015/138981 | 9/2015 |
| WO | WO 2015/148184 | 10/2015 |
| WO | WO 2015/164706 | 10/2015 |
| WO | WO 2015/187712 | 12/2015 |
| WO | WO 2016/007093 | 1/2016 |
| WO | WO 2016/019250 | 2/2016 |
| WO | WO 2016/032929 | 3/2016 |
| WO | WO 2016/094728 | 6/2016 |
| WO | WO 2016/102958 | 6/2016 |
| WO | WO 2016/110804 | 7/2016 |
| WO | WO 2016/128985 | 8/2016 |
| WO | WO 2016/149751 | 9/2016 |
| WO | WO 2016/166281 | 10/2016 |
| WO | WO 2016/176668 | 11/2016 |
| WO | WO 2016/179407 | 11/2016 |
| WO | WO 2016/189422 | 12/2016 |
| WO | WO 2016/195587 | 12/2016 |
| WO | WO 2016/201366 | 12/2016 |
| WO | WO 2017/004021 | 1/2017 |
| WO | WO 2017/010930 | 1/2017 |
| WO | WO 2017/023864 | 2/2017 |
| WO | WO 2017/044904 | 3/2017 |
| WO | WO 2017/053847 | 3/2017 |
| WO | WO 2017/062994 | 4/2017 |
| WO | WO 2017/086798 | 5/2017 |
| WO | WO 2017/088573 | 6/2017 |
| WO | WO 2017/105930 | 6/2017 |
| WO | WO 2017/132067 | 8/2017 |
| WO | WO 2017/199026 | 11/2017 |
| WO | WO 2017/208167 | 12/2017 |
| WO | WO 2017/209673 | 12/2017 |
| WO | WO 2017/210729 | 12/2017 |
| WO | WO 2017/221037 | 12/2017 |
| WO | WO 2018/009680 | 1/2018 |
| WO | WO 2018/028170 | 2/2018 |
| WO | WO 2018/028220 | 2/2018 |
| WO | WO 2018/028221 | 2/2018 |
| WO | WO 2018/039458 | 3/2018 |
| WO | WO 2018/093765 | 5/2018 |
| WO | WO 2018/106839 | 6/2018 |
| WO | WO 2018/112164 | 6/2018 |
| WO | WO 2018119220 | 6/2018 |
| WO | WO 2018/187241 | 10/2018 |
| WO | WO 2019/005774 | 1/2019 |
| WO | WO 2019/014250 | 1/2019 |
| WO | WO 2019/028000 | 2/2019 |
| WO | WO 2019/046180 | 3/2019 |
| WO | WO 2019/082180 | 6/2019 |
| WO | WO 2019/143790 | 7/2019 |
| WO | WO 2019/169240 | 9/2019 |
| WO | WO 2019/202489 | 10/2019 |
| WO | WO 2019/213433 | 11/2019 |

(56) References Cited

FOREIGN PATENT DOCUMENTS

| | | |
|---|---|---|
| WO | WO 2020/006048 | 1/2020 |
| WO | WO 2020/068830 | 4/2020 |
| WO | WO 2020/069219 | 4/2020 |
| WO | WO 2020/086726 | 4/2020 |
| WO | WO 2020/131857 | 6/2020 |
| WO | WO 2020/185601 | 9/2020 |
| WO | WO 2020/252406 | 12/2020 |
| WO | WO 2021/005584 | 1/2021 |
| WO | WO 2021/055716 | 3/2021 |
| WO | WO 2021/062345 | 4/2021 |
| WO | WO 2021/092533 | 5/2021 |
| WO | WO 2021/127422 | 6/2021 |
| WO | WO 2021/228128 | 11/2021 |
| WO | WO 2021/236815 | 11/2021 |
| WO | WO 2021/252292 | 12/2021 |
| WO | WO 2022/090834 | 5/2022 |
| WO | WO 2022/146295 | 7/2022 |
| WO | WO 2022/187318 | 9/2022 |
| WO | WO 2022/187486 | 9/2022 |
| WO | WO 2022/221858 | 10/2022 |
| WO | WO 2022/235607 | 11/2022 |
| WO | WO 2023/283568 | 1/2023 |
| WO | WO 2023/014499 | 2/2023 |
| WO | WO 2023/015158 | 2/2023 |
| WO | WO 2023/015159 | 3/2023 |
| WO | WO 2023/129722 | 7/2023 |
| WO | WO 2023/156391 | 8/2023 |
| WO | WO 2023/163300 | 8/2023 |
| WO | WO 2023/168016 | 9/2023 |
| WO | WO 2023/191236 | 10/2023 |
| WO | WO 2023/192519 | 10/2023 |
| WO | WO 2023/196578 | 10/2023 |
| WO | WO 2023/215558 | 11/2023 |
| WO | WO 2023/222911 | 11/2023 |
| WO | WO 2023/224636 | 11/2023 |
| WO | WO 2024/059136 | 3/2024 |
| WO | WO 2024/059140 | 3/2024 |
| WO | WO 2024/059141 | 3/2024 |
| WO | WO 2024/059643 | 3/2024 |
| WO | WO 2024/059651 | 3/2024 |
| WO | WO 2024/059663 | 3/2024 |
| WO | WO 2024/083685 | 4/2024 |
| WO | WO 2024/086209 | 4/2024 |
| WO | WO 2024/119042 | 6/2024 |
| WO | WO 2024/155527 | 7/2024 |
| WO | WO 2024/182256 | 9/2024 |
| WO | WO 2024/206883 | 10/2024 |
| WO | WO 2024/215916 | 10/2024 |
| WO | WO 2024/218174 | 10/2024 |
| WO | WO 2024/228655 | 11/2024 |
| WO | WO 2024/233290 | 11/2024 |
| WO | WO 2024/234051 | 11/2024 |
| WO | WO 2024/238988 | 11/2024 |
| WO | WO 2024/241067 | 11/2024 |
| WO | WO2024/243537 | 11/2024 |
| WO | WO 2024/258592 | 12/2024 |
| WO | WO 2025/000028 | 1/2025 |
| WO | WO 2025/010365 | 1/2025 |
| WO | WO 2025/015047 | 1/2025 |
| WO | WO 2025/024798 | 1/2025 |
| WO | WO 2025/029578 | 2/2025 |
| WO | WO 2025/029692 | 2/2025 |
| WO | WO 2025/029698 | 2/2025 |
| WO | WO 2025/038457 | 2/2025 |
| WO | WO 2025/038622 | 2/2025 |
| WO | WO 2025/046593 | 3/2025 |
| WO | WO 2025/049694 | 3/2025 |
| WO | WO 2025/069021 | 4/2025 |
| WO | WO 2025/080428 | 4/2025 |
| WO | WO 2025/081022 | 4/2025 |
| WO | WO 2025/219728 | 4/2025 |
| WO | WO 2025068762 | 4/2025 |
| WO | WO 2025/087735 | 5/2025 |
| WO | WO 2025/099587 | 5/2025 |
| WO | WO 2025/104232 | 5/2025 |
| WO | WO 2025/106892 | 5/2025 |
| WO | WO 2025/117608 | 6/2025 |
| WO | WO 2025/117609 | 6/2025 |
| WO | WO 2025/127179 | 6/2025 |
| WO | WO 2025/128510 | 6/2025 |
| WO | WO 2025/128825 | 6/2025 |
| WO | WO 2025/133597 | 6/2025 |
| WO | WO 2025/136631 | 6/2025 |
| WO | WO 2025/151398 | 7/2025 |
| WO | WO 2025/151439 | 7/2025 |
| WO | WO 2025/155529 | 7/2025 |
| WO | WO 2025/175157 | 8/2025 |
| WO | WO 2025/177139 | 8/2025 |
| WO | WO 2025/193607 | 9/2025 |
| WO | WO 2025/219826 | 10/2025 |
| WO | WO 2025/220500 | 10/2025 |
| WO | WO 2025/226257 | 10/2025 |
| WO | WO 2025/231998 | 11/2025 |
| WO | WO 2025/240843 | 11/2025 |
| WO | WO 2025/243290 | 11/2025 |
| WO | WO 2025/245482 | 11/2025 |
| WO | WO 2025/247161 | 12/2025 |
| WO | WO 2025/250395 | 12/2025 |
| WO | WO 2025/264783 | 12/2025 |
| WO | WO 2026/003575 | 1/2026 |
| WO | WO 2026/003759 | 1/2026 |
| WO | WO 2026/005669 | 1/2026 |
| WO | WO 2026/010730 | 1/2026 |
| WO | WO 2026/011148 | 1/2026 |
| WO | WO 2026/020207 | 1/2026 |
| WO | WO 2026/060203 | 3/2026 |

OTHER PUBLICATIONS

U.S. Appl. No. 15/277,946, filed Sep. 27, 2016, Rosenbluth et al..
U.S. Appl. No. 15/354,943, filed Nov. 17, 2016, Wong et al..
U.S. Appl. No. 15/580,631, filed Dec. 7, 2017, Wong et al..
U.S. Appl. No. 15/721,475, filed Sep. 29, 2017, Wong et al..
U.S. Appl. No. 15/721,480, filed Sep. 29, 2017, Wong et al..
U.S. Appl. No. 15/748,616, filed Jan. 29, 2018, Hamner et al.
U.S. Appl. No. 15/762,043, filed Mar. 21, 2018, Hamner et al.
U.S. Appl. No. 16/071,056, filed Jul. 18, 2018, Wong et al.
U.S. Appl. No. 16/241,846, filed Jan. 7, 2019, Wong et al.
U.S. Appl. No. 16/242,983, filed Jan. 8, 2019, Wong et al.
U.S. Appl. No. 16/247,310, filed Feb. 22, 2019, Wong et al.
U.S. Appl. No. 16/327,780, filed Feb. 22, 2019, Hamner et al.
U.S. Appl. No. 16/780,758, filed Feb. 3, 2020, Hamner et al.
U.S. Appl. No. 16/792,100, filed Feb. 14, 2020, Hamner et al.
U.S. Appl. No. 16/833,388, filed Mar. 27, 2020, Hamner et al.
U.S. Appl. No. 16/962,810, filed Jul. 16, 2002, Hamner et al.
U.S. Appl. No. 16/993,085, filed Aug. 13, 2020, Balbaky et al.
U.S. Appl. No. 17/013,396 filed 09-04-1001, Wong et al.
U.S. Appl. No. 17/052,483, filed Nov. 2, 2020, Liberatore et al.
U.S. Appl. No. 17/061,231, filed Oct. 1, 2020, Yu.
U.S. Appl. No. 17/080,544, filed Oct. 26, 2020, Wong et al.
U.S. Appl. No. 17/633,004, filed May 11, 2020, Wong et al.
U.S. Appl. No. 17/633,010, filed May 11, 2022, Wong et al.
Amarenco et al. "Urondynamic Effect of Acute Transducteaneous Posterior Tibial Nerve Stimulation in Overactive Bladder" Journal of Urology vol. 169, 2210-2215 (Jun. 2003).
APARTIS; Clinical neurophysiology in movement disorders. Handb Clin Neurol; 111; Pediatric Neurology Pt. 1; pp. 87-92;Apr. 2013.
Barath et al., 2020, Brain metabolic changes with longitudinal transcutaneous afferent patterned stimulation in essential tremor subjects, Tremor and Other Hyperkinetic Movements, 10(1):52, pp. 1-10.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.

(56) References Cited

OTHER PUBLICATIONS

Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.
Birdno et al.; Response of human thalamic neurons to high-frequency stimulation.; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. “Vagus nerve stimulation: a new promising therapeutic tool in inflammatory bowel disease.” Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: No. neural connection from the vagus to splenic sympathetic neurons; Exp Physiol 97.11 (2012); pp. 1180-1185.
Brillman et al., 2022, Real-world evidence of transcutaneous afferent patterned stimulation for essential tremor, Tremor and Other Hyperkinetic Movements, 12(1):27, pp. 1-11.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006.
Buschbacher et al.; Manual of nerve conduction series; 2nd edition; Demos Medical Publishing, LLC; 2006 (part 2, pg. #143 to #299).
Cagnan et al.; Phase dependent modulation of tremor amplitude in essential tremor through thalamic stimulation; Brain; 136(10); pp. 3062-3075; Oct. 2013.
Campero et al.; Peripheral projections of sensory fascicles in the human superficial radial nerve; Brain; 128(Pt 4); pp. 892-895; Apr. 2005.
Chen et al.; A web-based system for home monitoring of patients with Parkinson’s disease using wearable sensors; IEEE Trans on Bio-Medical Engineering; 58(3); pp. 831-836; Mar. 2011.
Choi, Jong Bo, et al. “Analysis of heart rate variability in female patients with overactive bladder.” Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975;presented at IFSCC Vilith Int’l Congress on Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs .; Jan. 2012.
Deuschl et at; Consensus statement of the Movement Disorder Society on Tremor. Ad Hoc Scientific Committee., Movement Disorders, vol. 13 Suppl 3, pp. 2-23; 1998.
Di Giovangiulio et al.; The Neuromodulation of the intestinal immune system and its relevance in inflammatory bowel disease; Frontier’s in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation;Converging Clinical and Engineering Research on Neurorehabilitation; vol. 1 (Biosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Ferreira et al., 2019, MDS evidence-based review of treatments for essential tremor, Movement Disorders, 34(7):950-958.
Fiorentino et al., 2011, Self calibrating wearable active running asymmetry measurement and correction, Journal of Control Engineering and Applied Informatics, 13(2):3-8.
Fred E. Govier, et al., “Percutaneous Afferent Neuromodulation for the Refractory Overactive Bladder: Results of a Multicenter Study,” 165 J. Urology 1193-1198 (Apr. 2001).
Fuentes et al.; Restoration of locomotive function in Parkinson’s disease by spinal cord stimulation:mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson’s disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al.; Real-time estimation of pathological tremor parameters from gyroscope data.; Sensors; 10(3); pp. 2129-2149; Mar. 2010.
Gallego et al.; A soft wearable robot for tremor assessment and suppression; 2011 IEEE InternationalConference on Robotics and Automation; Shanghai International Conference Center; pp. 2249-2254; May 9-13, 2011.
Gao; Analysis of amplitude and frequency variations of essential and Parkinsonian tremors; Medical & Biological Engineering & Computing; 42(3); pp. 345-349; May 2004.
Garcia et al.; Modulation of brainstem activity and connectivity by respiratory-gated auricular vagalafferent nerve stimulation in migraine patients; PAIN; International Association for the Study of Pain; 2017.
Garcia-Rill, E., et al. “Arousal, motor control, and Parkinson’s disease.”pp. 198-207 (2015).
Giuffridda et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulation of innervated muscle; Archives of Physical Medicine and Rehabilitation; 56(6); pp. 243-249; Jun. 1975.
Gupta et al., 2021, Exploring essential tremor: results from a large online survey, Clinical Parkinsonism & Related Disorders, 5:100101, 4 pp.
H.C. Klingler, et al., “Use of Peripheral Neuromodulation of the S3 Region for Treatment of Detrusor Overactivity: A Urodynamicbased Study,” Urology 56:766-771, 2000.
Haeri et al.; Modeling the Parkinson’s tremor and its treatments; Journal of Theoretical Biology; 236(3); pp. 311-322; Oct. 2005.

(56) References Cited

OTHER PUBLICATIONS

Halonen et al.; Contribution of cutaneous and muscle afferent fibres to cortical SEPs followingmedian and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission oftremor signals in patients with Parkinson's disease; 6th International Conference on Neural Engineering; San Diego, CA; pp. 355-358; Nov. 2013.
Haubenberger et al., 2018, Essential Tremor, The New England Journal of Medicine, 378:1802-1810 and Supplementary Appendix.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation forchannel prototype stimulator and electrode array: Results from a gait-labEngineering & Physic; 35(1); pp. 74-81; Jan. 2013.
Hellwig et al., Feb. 17, 2001, Tremor-correlated cortical activity in essential tremor, The Lancet, 357:519-523.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp. 170-175.
Hernandez-Martin et al., 2021, High-fidelity transmission of high-frequency burst stimuli from peripheral nerve to thalamic nuclei in children with dystonia, Scientific Reports, 11:8498, 9 pp.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heartrate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurology and urodynamics 30.8 (2011): 1467-1472.
Inoue et al. "Stretchable human interface using a conductive silicone elastomer containing silver fillers." Consumer Electronics, 2009. ISCE'09. IEEE 13th International Symposium on. IEEE, 2009.
Isaacson et al., 2020, Prospective home-use study on non-invasive neuromodulation therapy for essential tremor, Tremor and Other Hyperkinetic Movements, 10(1):29, pp. 1-16.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,; 56(2); pp. 452-461; Feb. 2009.
Krauss et al.; Chronic spinal cord stimulation in medically intractable orthostatic tremor; J Neurol Neurosurg Psychiatry; 77(9); pp. 1013-1016; Sep. 2006.
Krishnamoorthy et al., 2008, Gait Training After Stroke: A Pilot Study Combining a Gravity-BalancedOrthosis, Functional Electrical Stimulation, and Visual Feedback, Journal of Neurologic Physical Therapy, 32(4):192-202.
Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous ElectricalStimulation of the Forearm; Neural Systems and Rehabilitation Engineering, IEEE Transactions on; 18(3); pp. 255-262; Jun. 2010.
Kunz, Patrik, et al. "5 kHz transcranial alternating current stimulation: lack of cortical excitability changes when grouped in a theta burst pattern." Frontiers in Human Neuroscience 10 (2016): 683.
Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.
Laroy et al.; The sensory innervation pattern of the fingers; J. Neurol.; 245 (5); pp. 294-298; May 1998.
Lee et al.; Resetting of tremor by mechanical perturbations: A comparison of essential tremor and parkinsonian tremor; Annals of Neurology; 10(6); pp. 523-531; Dec. 1981.
Legon et al.; Pulsed ultrasound differentially stimulates somatosensory circuits in humans as indicated by EEG and fMRI; PLoS ONE; 7(12); e51177; 14 pgs.; Dec. 2012.
Liao, Wen-Chien, et al. "A noninvasive evaluation of autonomic nervous system dysfunction in women with an overactive bladder." International Journal of Gynecology & Obstetrics 110.1 (2010): 12-17.
Lin et al., 2018, Noninvasive neuromodulation inessential tremor demonstrates relief in a sham- controlled pilot trial, Movement Disorders, 33(7):1182-1183.
Llinas et al., Dec. 21, 1999, Thalamocortical dysrhythmia: a neurological and neuropsychiatric syndrome characterized by magnetoencephalography, PNAS, 96(26):15222-15227.
Lourenco et al.; Effects produced in human arm and forearm motoneurons after electrical stimulation of ulnar and median nerves at wrist level; Experimental Brain Research; 178(2); pp. 267-284; Apr. 2007.
Lyons et al., 2021, Essential tremor in adult patients, International Essential Tremor Foundation, 16 pp.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
McAuley et al.; Physiological and pathological tremors and rhythmic central motor control; Brain; 123(Pt 8); pp. 1545-1567; Aug. 2000.
McIntyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.
Mehnert, Ulrich, et al. "Heart rate variability: an objective measure of autonomic activity and bladder sensations during urodynamics." Neurology and urodynamics 28.4 (2009): 313-319.
Michael R. Van Balken, et al., "Posterior Tibial Nerve Stimulation as Neuromodulative Treatment of Lower Urinary Track Dysfunction," 166 J. Urology 914-918 (Sep. 2001).
Miguel et al.; Alcohol consumption and the incidence of Parkinson's disease; Ann. Neurol.; 54(2); pp. 170-175; May 15, 2003.
Miller et al.; Multiplexed microneedle-based biosensor array for characterization of metabolic acidosis; Talanta; 88; pp. 739-742; Jan. 2012 (author manuscript; 13 pgs.).
Miller et al.; Neurostimulation in the treatment of primary headaches; Pract Neurol; Apr. 11, 2016;16:pp. 362-375.

(56) References Cited

OTHER PUBLICATIONS

Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulationof subthalamic nucleus?; Results of a Questionnaire, Parkinsonism Relat Disord; 13; pp. 528-531; Dec. 2007.
Munhoz et al.; Acute effect of transcutaneous electrical nerve stimulation on tremor; Movement Disorders; 18(2); pp. 191-194; Feb. 2003.
Nardone et al.; Influences of transcutaneous electrical stimulation of cutaneous and mixed nerves onsubcortical somatosensory evoked potentials; Electroenceph. Clin. Neurophysiol.; 74(1); pp. 24-35; Jan.-Feb. 1989.
Nonis et al.; Evidence of activation of vagal afferents by non-invasive vagus nerve stimulation: Anelectrophysiological study in healthy volunteers; Cephalalgia; pp. 1285-1293; vol. 37(13); Mar. 28, 2017.
Pahwa et al., 2018, An acute randomized controlled trial of noninvasive peripheral nerve stimulation in essential tremor, Neuromodulation, 22:537-545.
Peng et al., 2015, Flexible dry electrode based on carbon nanotube/polymer hybrid micropillars for biopotential recording, Sensor and Actuatora A: Physical, 235:48-65.
Perez et al.; Patterned Sensory Stimulation Induces Plasticity in Reciprocal la Inhibition in Humans; The Journal of Neuroscience; 23(6); pp. 2014-2018; Mar. 2003.
Perez-Reyes, Jan. 2003, Molecular physiology of low-voltage-activated T-type calcium channels, Physiol. Rev. 83:117-161.
Perlmutter et al.; Deep brain stimulation; Ann Rev Neurosci; 29; pp. 229-257; Jul. 2006.
Popovi Maneski et al.; Electrical stimulation for the suppression of pathological tremor; Medical & Biological Engineering & Computing; 49(10); pp. 1187-1193; Oct. 2011.
Popovic-Bijelic et al. “Multi-field surface electrode for selective electrical stimulation.” Artificial organs 29.6 (2005): 448-452.
Prochazka et al.; Attenuation of pathological tremors by functional electrical stimulation I: Method; Annals of Biomedical Engineering; 20(2); pp. 205-224; Mar. 1992.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-8; Jan.-Feb. 2003.
Rocon et al.; Design and validation of a rehabilitation robotic exoskeleton for tremor assessment and suppression; IEEE Trans Neural Sys and Rehab Eng.; 15(3); pp. 367-378; Sep. 2007.
Sigrist et al., 2012. Augmented visual, auditory, haptic, and multimodal feedback in motor learning: A review. Psychonomic Bulletin & Review, 20(1):21-53.
Silverstone et al.; Non-Invasive Neurostimulation In The Control of Familial Essential Tremor UsingThe Synaptic Neuromodulator; Conference Proceedings, International Functional Electrical Stimulation Society (IFES); Ed. Paul Meadows; 3 pgs.; May 1999.
Singer et al.; The effect of EMG triggered electrical stimulation plus task practice on arm function inchronic stroke patients with moderate-severe arm deficits; Restor Neurol Neurosci; 31(6); pp. 681-691; Oct. 2013.
Solomonow et al., 1998, Studies toward spasticity suppression with high frequency electrical stimulation, Orthopedics, 7(8):1284-1288.
Straube et al.; Treatment of chronic migraine with transcutaneous stimulation of the auricular branchof the vagal nerve (auricular t-VNS): a randomized, monocentric clinical trial; The Journal of Headache and Pain (2015) 16:63.
Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Biol Cybern; 89(2); pp. 81-88; Aug. 2003.
Thomas et al.; A review of posterior tibial nerve stimulation for faecal incontinence; ColorectalDisease; 2012 The Association of Coloproctology of Great Britain and Ireland. 15, pp. 519-526; Jun. 25, 2012.
Tolosa et al.; Essential tremor: treatment with propranolol; Neurology; 25(11); pp. 1041; Nov. 1975.
Tracey; The inflammatory reflex; Nature; vol. 420; pp. 853-859; Dec. 19-26, 2002.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs.; 2011.
Vitton et al.; Transcutaneous posterior tibial nerve stimulation for fecal Incontinence in inflammatorybowel disease patients: a therapeutic option?; Inflamm Bowel Dis; vol. 15, No. 3, Mar. 2009; pp. 402-405.
Von Lewinski et al.; Efficacy of EMG-triggered electrical arm stimulation in chronic hemiparetic stroke patients; Restor Neurol Neurosci; 27(3); pp. 189-197; Jun. 2009.
Wallerberger, Apr. 4, 2019, Efficient Estimation of Autocorrelation Spectra, ArXiv.org, https://arxiv.org/abs/1810.05079.
Wardman et al.; Subcortical, and cerebellar activation evoked by selective stimulation of muscle and cutaneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.
Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.
Yarnitsky et al.; Nonpainful remote electrical stimulation alleviates episodic migraine pain; Neurology 88; pp. 1250-1255; Mar. 28, 2017.
Yeh et al., “Intensity sensitive modulation effect of theta burst form of median nerve stimulation on the monosynaptic spinal reflex.” Neural plasticity 2015 (2015) in 8 pages.
Yilmaz, Ozlem O., et al. “Efficacy of EMG-biofeedback in knee osteoarthritis.” Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Undated.
Zwarts et al.; Multichannel surface EMG: basic aspects and clinical utility; Muscle Nerve; 28(1); pp. 1-17; Jul. 2003.
International Search Report and Written Opinion in application No. PCT/US2019/030458 dated Aug. 22, 2019.
Cala Trio Health Care Professional Guide (Jul. 2020).
Cala Trio Health Care Professional Guide (Nov. 2019).
Chang, M.D., Qwang-Yuen et al., Effect of Electroacupuncture and Transcutaneous Electrical Nerve Stimulation at Hegu (LI.4) Acupuncture Point on the Cutaneous Reflect, 27 Acupuncture & Electro-Therapeutics Res., Int. J. 191-202 (2002).
Javidan, et al., Attenuation of Pathological Tremors by Functional Electrical Stimulation II: Clinical Evaluation, 20 Annals of Biomedical Engineering 225 (1992).

(56) References Cited

OTHER PUBLICATIONS

Knutson et al., Neuromuscular Electrical Stimulation for Motor Restoration in Hemiplegia. Phys Med Rehabil Clin N A,. Nov. 2015; 26(4): 729-745. Published online Aug. 14, 2015. Doi: 10.1016/j.pmr.2015.06.002.

PTAB-IPR2024-00732—Exhibit 1002—Declaration of John Laughlin, M. Eng., P.E., in 109 pages.

PTAB-IPR2024-00732—Petition for Inter Partes Review of U.S. Pat. No. 10,786,669, filed Mar. 29, 2024, in 101 pages.

|PTAB-IPR2024-00743—Exhibit 1002—Declaration of John Laughlin, M. Eng., P.E., in 102 pages.

PTAB-IPR2024-00743—Petition for Inter Partes Review of U.S. Pat. No. 11,628,300, filed Mar. 29, 2024, in 113 pages.

Antal et al., Anodal Transcranial Direct Current Stimulation of the Motor Cortex Ameliorates Chronic Pain and Reduces Short Intracortical Inhibition, Journal of Pain and Symptom Management, vol. 39, No. 5, pp. 890-903, May 2010.

Falco et al., Cross Talk: A New Method for Peripheral Nerve Stimulation. An Observational Report with Cadaveric Verification, Pain Physician, 12:965-983, 2009.

Lowry et al., Spinal Cord Stimulation for the Treatment of Chronic Knee Pain Following Total Knee Replacement, Pain Physician, 13:251-256, 2010.

AEMED, Inc., 510(k) Summary, StimPad™ TENS System, Dec. 6, 2007.

Encore Medical, L.P., Intelect Transport 2 Channel Electrotherapy User Manual, 2005.

Fowler et al., The conduction velocities of peripheral nerve fibres conveying sensations of warming and cooling, Journal of Neurology, Neurosurgery and Psychiatry Sep. 1988;51(9):1164-70.

Griffin et al., Efficacy of High Voltage Pulsed Current for Healing of Pressure Ulcers in Patents with Spinal Cord Injury, Physical Therapy, vol. 71, No. 6, Jun. 1991, pp. 433-442.

Johnson, Factors Influencing The Analgesic Effects and Clinical Efficacy of Transcutaneous Electrical Nerve Stimulation (TENS), Newcastle University, Jul. 1991.

Jones et al., Trancutaneous electronical nerve stimulation, Continuing Education in Anaethesia, Critical Care & Pain, vol. 9, No. 4, pp. 130-135, 2009.

Korkmaz et al., Pulsed radiofrequency versus conventional transcutaneous electrical nerve stimulation in painful shoulder: a prospective, randomized study, Clin Rehabil. Nov. 2010;24(11):1000-8, Aug. 4, 2010.

Miller et al., Superimposed single impulse and pulse train electrical stimulation: A quantitative assessment during submaximal isometric knee extension in young, healthy men, Superimposed Electrical Stimulation Techniques, Muscle & Nerve, Aug. 1999, pp. 1038-1046.

De Santana, et al., Effectiveness of Transcutaneous Electrical Nerve Stimulation for Treatment of Hyperalgesia and Pain, Curr Rheumatol Rep.; 10(6): 492-499, Dec. 2008.

Cala klQ, calahealth.com, [online], [site visited Mar. 7, 2025], Available from internet URL: https://calahealth.com/ (Year: 2025).

Dewey, et al., A Pilot Study of Ai-Controled Transcutaneous Peripheral Nerve Stimulation for Essential Tremor, Tremor and Other Hyperkinetic Movements, 2025; 15(1):10, pp. 1-9.

Feinstein Institutes for Medical Research, Northwell Health; High-frequency electrical stimulation helps reduce inflammation pain in new Feinstein Institute study; Press Release Oct. 5, 2022.

Trends in the Health Wearable Technology, first available Oct. 26, 2021, mokosmart.com, [online], [site visited Mar. 7, 2025], Available from internet URL: https://www.mokosmart.com/health-wearable-technology-trends/ (Year: 2021).

Yang et al.; High-frequency electrical stimulation attenuates neuronal release of inflammatory mediators and ameliorates neuropathic pain, Bioelectronic Medicine, 8(1); pp. 1-13; Oct. 5, 2022.

Hu et al., Pain modulation effect of breathing-controlled electrical stimulation (BreEStim) is not likely to be mediated by deep and fast voluntary breathing. Sci Rep 5, 14228 (2015). (Year: 2015).

Lauk et al., "A software for recording and analysis of human tremor," Computer Methods and Programs in Biomedicine 60 (1999) 65-77, https://www.sciencedirect.com/science/article/pii/S0169260799000127?via%3Dihub.

Nouman et al.; Additive blooming in polymer materials: Consequences in the pharmaceutical and medical field, Polymer Degradation and Stability, vol. 143, Sep. 2017, pp. 239-252 (Year: 2017).

Rajaraman et al., "A novel quantitative method for 3D measurement of Parkinsonian tremor," Clin Neurophysiol, Feb. 2000; 111(2):338-43, https://pubmed.ncbi.nlm.nih.gov/10680570/.

Technical Presentation: Third-Stream Additives that Modify LSR and HCR, Nov. 13, 2020 [online]; RDAbbott webpage; hyperlink titled "presentation"; [https://rdabbott.com/wp-content/uploads/2020/11/ISC2020-Third-Stream-Additives-for-LSR-and-HCR_20201113.pdf], p. 20, p. 23 (Year: 2020).

Wang et al.; Mechanically Flexible Conductors for Stretchable and Wearable E-Skin and E-Textile Devices, May 2019; [https:// doi.org/10.1002/adma.201901408] (Year: 2019).

* cited by examiner

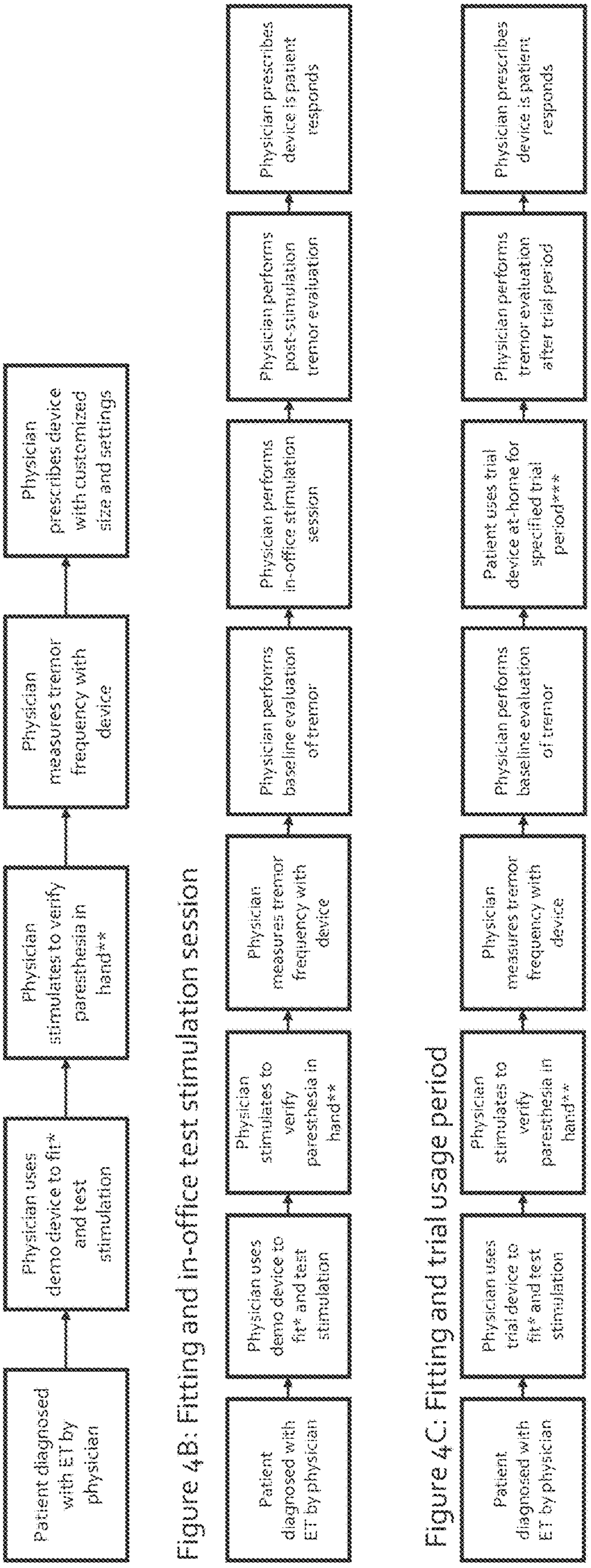

Figure 4A: Fitting and testing proper nerve stimulation

Figure 4B: Fitting and in-office test stimulation session

Figure 4C: Fitting and trial usage period

* Multiple, e.g., three or other sizes are available to accommodate various wrist sizes

** Paresthesia confirmed in hand regions associated with, e.g., median and radial nerves

*** Trial period could be 3, 4, 5, 6, 7, 14, 21, 30, or 90 days, as non-limiting examples

WEARABLE, ERGONOMIC NEUROSTIMULATION SYSTEM

PRIORITY CLAIM

This application is a U.S. National Phase of PCT Patent Application No. PCT/US2019/030458, filed May 2, 2019 which claims the benefit under 35 U.S.C. § 119(e) as a nonprovisional application of U.S. App. No. 62/666,647 filed on May 3, 2018, both of which are hereby incorporated by reference in their entireties.

FIELD OF THE INVENTION

Some embodiments of the invention relate generally to systems, devices, and methods for stimulating nerves, and more specifically relate to system, devices, and methods for electrically stimulating peripheral nerve(s) to treat various disorders. Systems and methods as described herein can also include one, two, or more features as described, for example in U.S. Pat. No. 9,452,287 to Rosenbluth et al., U.S. Pat. No. 9,802,041 to Wong et al., PCT Pub. No. WO 2016/201366 to Wong et al., PCT Pub. No. WO 2017/132067 to Wong et al., PCT Pub. No. WO 2017/023864 to Hamner et al., PCT Pub. No. WO 2017/053847 to Hamner et al., PCT Pub. No. WO 2018/009680 to Wong et al., and PCT Pub. No. WO 2018/039458 to Rosenbluth et al., each of the foregoing of which are hereby incorporated by reference in their entireties.

DESCRIPTION OF THE RELATED ART

Electrical energy can be delivered transcutaneously via electrodes on the skin surface with neurostimulation systems to stimulate peripheral nerves, such as the median, radial, and/or ulnar nerves in the upper extremities, or the tibial, saphenous, and/or peroneal nerve in the lower extremities as non-limiting examples. Electrical stimulation of these nerves has been shown to provide therapeutic benefit across a variety of diseases, including but not limited to movement disorders (including but not limited to essential tremor, Parkinson's tremor, orthostatic tremor, and multiple sclerosis), urological disorders, gastrointestinal disorders, cardiac diseases, and inflammatory diseases, among others. A number of conditions, such as tremors, can be treated through some form of transcutaneous peripheral nerve stimulation.

Other disorders can also be treated through peripheral nerve neurostimulation. For example, modulation of the sacral, saphenous, and/or tibial nerve could potentially improve symptoms of overactive bladder and urinary incontinence, and modulation of autonomic nerves, such as the vagus or tibial nerve relating to the parasympathetic nervous system, and/or any number of nerves associated with the sympathetic nervous system, could potentially improve symptoms of hypertension and cardiac dysrhythmias. Wearable systems with compact, ergonomic form factors are needed to enhance efficacy, compliance, and comfort with using the devices.

SUMMARY

In some embodiments, disclosed herein is a wearable neurostimulation device for transcutaneously stimulating one or more peripheral nerves of a user. The device can include any number of: an enclosure housing circuitry configured to generate electric stimulation signals, the enclosure having a top surface, a bottom surface, and a sidewall joining the top surface and the bottom surface; and an adjustable band configured to be worn by the user, the band having an inner side and an outer side, the inner side comprising at least one electrode for each nerve to be stimulated. In some embodiments, the enclosure can take an oval shape and includes curved top and bottom surfaces directly connected to each other, and does not comprise a separate sidewall therebetween. In some cases, an additional electrode can be present to serve as a return or counter electrode. In some cases, the enclosure can be removably attachable to the outer side of the band. The band can include an electrical interface member configured to both electrically and mechanically couple to the enclosure. In some embodiments, the electrical interface member allows for a direct connection between the enclosure and the band, and the electrical interface member does not comprise an external connection cable between the enclosure and the band. The bottom surface of the enclosure can include one or more electrical stimulation contacts. Each electrical stimulation contact can correspond to a different electrode of the band. The electrical stimulation contacts can be configured to be electrically connected to the electrical interface member. The enclosure can include one, two, or more stimulation buttons configured to start and stop delivery of the neurostimulation signals. In some embodiments, the stimulation button is positioned on the top surface of the enclosure. The stimulation button can be biased upward by a bracket spring feature. The bracket spring feature can include a generally flat surface and a plurality of spring fingers cut from the flat surface. The spring fingers can be configured to press upward on the stimulation button. The bracket spring can also be a cylindrical or annular spring element constructed from, for example, a compliant foam or polymer material. The enclosure can include one or more auxiliary interface features configured to allow the user to modulate one or more stimulation parameters. The one or more auxiliary interface features can be positioned on the sidewall of the enclosure. In some cases, the auxiliary interface features can be positioned on the top surface and/or bottom surface of the enclosure. The bottom surface of the enclosure can include one lifted edge on the longer side of the enclosure or two lifted edges positioned opposite one another. The lifted edge(s) can be configured to allow a user to insert his or her fingers between the bottom surface and the band in order for the user to grip the enclosure. The enclosure can include one or more charging ports configured to receive power from an external source to charge a rechargeable battery contained within the enclosure and an electrical connector configured to electrically connect the charging ports to the rechargeable battery. The same electrical connector can electrically connect the stimulation button to the circuitry configured to generate the stimulation signals. One or more charging ports can be positioned on a sidewall substantially opposite one or more auxiliary interface features. In some cases, one or more charging ports can be positioned on the bottom surface of the enclosure. The band can include at least a first electrode and a second electrode. The first electrode can be configured to stimulate the median nerve of the user and the second electrode being configured to stimulate the radial nerve of the user. The enclosure and the electrical interface member each can include ground or return electrode contacts configured to be electrically coupled to each other. The bottom surface of the enclosure can include a recess encompassing the one or more electrical stimulation contacts. The electrical interface member can be configured to be received within the recess to mechanically couple the enclosure to the band in a detachable manner. The electrical interface member and the enclosure can include corresponding keying features configured to ensure proper orientation of the enclosure when coupled to the band for left handed or right handed wear. One advantage of such an embodiment is that a single hardware stimulation unit can be manufactured, and the screen flipped or otherwise adjusted in software to configure for right-handed or left-handed uses. The electrical stimulation contacts can project from the bottom surface of the enclosure and can be configured to be received within recesses of the electrical interface member via a snap fit. The enclosure can have a length, a width, and a height, and the length of the enclosure can be longer, shorter, or substantially the same as the width of the enclosure. The band can include a length and a width. The length of the band can be longer than the width of the band. The enclosure can be configured to be coupled to the band so that the length of the band is oriented substantially transverse to a length of the band. The length of the enclosure can be longer than the width of the band. The enclosure can be configured to be coupled to the band such that the length of the enclosure extends substantially further beyond a first side of the band than beyond a second side of the band opposite the first side. The band can also include an aperture on a first end of the band through which a second end of the band is inserted to form a closed loop. The second end of the band can include a fastener for securing the band to itself in an adjustable length manner. In some cases, the fastener is a hook and loop type fastener, magnetic fastener, or a clasp. In some cases, a locking flap can extend from the fastener to prevent the second end of the band from retreating through the aperture to open the closed loop. In some embodiments, the electrical stimulation contacts project from the bottom surface of the enclosure and are configured to be received within recesses of the electrical interface member via a rotatable connection. In some embodiments, the sidewall comprises a first surface and a second surface opposing the first surface, and the second surface is configured to be a bracing surface.

In some embodiments, disclosed herein is a wearable neurostimulation system. The neurostimulation system can include the neurostimulator and a charger configured to electrically charge the rechargeable battery of the enclosure. The charger can include a top surface, a bottom surface, and a sidewall extending between the top surface and the bottom surface. The charger can also include a charging pocket formed in the top surface. The pocket can be configured to receive at least a portion of the enclosure. The charging pocket can include one or more charging contacts at the bottom of the charging pocket configured to electrically couple to and transfer power to the enclosure, and a charging cable configured to be coupled to an external power source for drawing power through the charger. The charging pocket can also include an opening in the top surface forming a top face of the charging pocket. A cross-sectional area of the charging pocket can taper inward as the charging pocket extends downward from the opening, the taper being configured to help guide the enclosure into the charging pocket. The charging pocket can also be configured to receive the enclosure such that the longest dimension of the enclosure extends upward from the top surface of the charger and the smallest dimension of the enclosure faces outward from a center of the charger. The charging pocket can also be positioned off the center of the charger, and/or dimensioned so that the band rests upon the top surface of the charger when the enclosure is being charged. The system can also include one or more charger magnets, and the enclosure can include one or more corresponding magnets configured to be attracted to one or more charger magnets. The charger magnets and the corresponding magnets can be configured to properly align the enclosure with the charging contacts at the bottom of the charging pocket. The charger can also include two charging magnets positioned symmetrically around the charging contacts of the charging pocket, and the enclosure can include two corresponding magnets positioned symmetrically around one or more charging ports configured to receive charge from the charger. The bottom surface of the charger can include a cable pocket for storing the charging cable. The cable pocket can include a holding magnet for holding a free end of the charging cable within the cable pocket when in a stored position. The bottom surface can also include a rim extending around the perimeter of the cable pocket. The rim can include an opening forming an exit which allows the cable to extend from the cable pocket when charging such that the bottom surface of the charger may remain flat on a supporting surface. The band can include a RFID tag, and the charger can include an RFID antenna. The RFID tag can be configured to communicate an age of the band to the charger. The charger can be configured not to charge the enclosure if the age of the band exceeds a threshold age, does not match a pre-determined identification, or other parameters. In some cases, the charger can include a first wireless communications antenna configured to receive and transmit data to and from a wireless communications antenna in the enclosure. In some cases, the RFID tag can be configured with a unique identifier associated with the patient or end user and the charger is configured to transmit or receive wireless data when the enclosure is in electrical connection with the charger and the appropriate RFID tag is in detected by an RFID antenna. In some cases, data transmitted between the enclosure and charger include but is not limited to device usage data, error data, motion or activity data, tremor motion data, and/or physiological data. In some cases, the charger can include a second wireless communications antenna configured to receive and transmit data from a system of remote servers, e.g., the cloud. In some cases, the charger is configured to transmit or receive wireless data only when the enclosure is in electrical connection with the charger and the appropriate RFID tag is detected by an RFID antenna. In some embodiments, the RFID tag is configured to communicate a unique personal identifier to the charger and the charger is configured not to charge the enclosure if the unique personal identifier is not recognized as valid by the charger. In some embodiments, the charger is configured to receive data from the enclosure when the enclosure is positioned in the charger, and wirelessly transmit the data to an external device.

Also disclosed herein is a wearable neurostimulation device for transcutaneously stimulating one or more peripheral nerves of a user. The device can include an enclosure housing circuitry configured to generate electric stimulation signals, the enclosure having a top surface and a bottom surface; and an adjustable band configured to be worn by the user, the band having an inner side and an outer side, the inner side comprising at least one electrode corresponding to each nerve to be stimulated. The band can comprise an electrical interface member configured to electrically and mechanically couple to the enclosure. The bottom surface of the enclosure comprises one or more electrical stimulation contacts, each electrical stimulation contact corresponding to a different electrode of the band, the electrical stimulation contacts configured to be electrically connected to the electrical interface.

In some embodiments, the enclosure is removably and directly attachable to the outer side of the band without a cable connector therebetween. In some embodiments, the electrical stimulation contacts project from the bottom surface of the enclosure and are configured to be received within recesses of the electrical interface member via a snap fit. In some embodiments, the electrical stimulation contacts project from the bottom surface of the enclosure and are configured to be received within recesses of the electrical interface member via a rotatable connection.

In some embodiments, the band comprises at least a first electrode and a second electrode, the first electrode being configured to stimulate the median nerve of the user and the second electrode being configured to stimulate the radial or ulnar nerve of the user. The enclosure and the electrical interface member can each comprise return electrode contacts configured to be electrically coupled to each other, and the bottom surface of the enclosure comprises a recess encompassing the one or more electrical stimulation contacts, wherein the electrical interface member is configured to be received within the recess to mechanically couple the enclosure to the band in a detachable manner.

In some embodiments, the band comprises an aperture on a first end of the band through which a second end of the band is inserted to form a closed loop, wherein the second end of the band comprises a hook and loop fastener for securing the band to itself in an adjustable length manner, and wherein a locking flap extends from the hook and loop fastener to prevent the second end of the band from retreating through the aperture to open the closed loop.

Also disclosed herein is a method of charging a wearable neurostimulation device for transcutaneously stimulating one or more peripheral nerves of a user. The method can include any number of providing the wearable stimulation device, comprising an enclosure and an adjustable band comprising an electrical interface member, the adjustable band configured to be electrically and mechanically coupled to the enclosure; detaching the adjustable band from the enclosure; connecting the enclosure to a charging station; verifying a unique identifier on the enclosure via the charging station; and wirelessly transmitting data received from the wearable stimulation device to an external device only while the enclosure is connected to the charging station. In some embodiments, the data is transmitted directly from the enclosure. In some embodiments, the data is transmitted from the enclosure to the charging station when the enclosure is connected to the charging station, and then wirelessly transmitted from the charging station to the external device. In some embodiments, wirelessly transmitting data does not occur when the enclosure is not connected to the charging station.

BRIEF DESCRIPTION OF THE DRAWINGS

FIGS. 4A-4C are flow charts of methods for fitting and/or testing of a device, according to some embodiments of the invention.

DETAILED DESCRIPTION

Disclosed herein are devices configured for providing neurostimulation. The neurostimulation devices provided herein may be configured to stimulate peripheral nerves of a user. The neurostimulation devices may be configured to transcutaneously transmit one or more neurostimulation signals across the skin of the user. In some embodiments, the neurostimulation devices are wearable devices configured to be worn by a user, such as only unilaterally, or bilaterally utilizing a plurality of devices in some cases. In some embodiments, the devices are configured to be worn on an upper or lower extremity, such as the arm, wrist, leg, or proximate to the knee or ankle. In some embodiments, the neurostimulation devices do not include any implantable components (e.g., implantable under the skin, or elsewhere within a body). The user may be a human, another mammal, or other animal user.

Figure 1B:
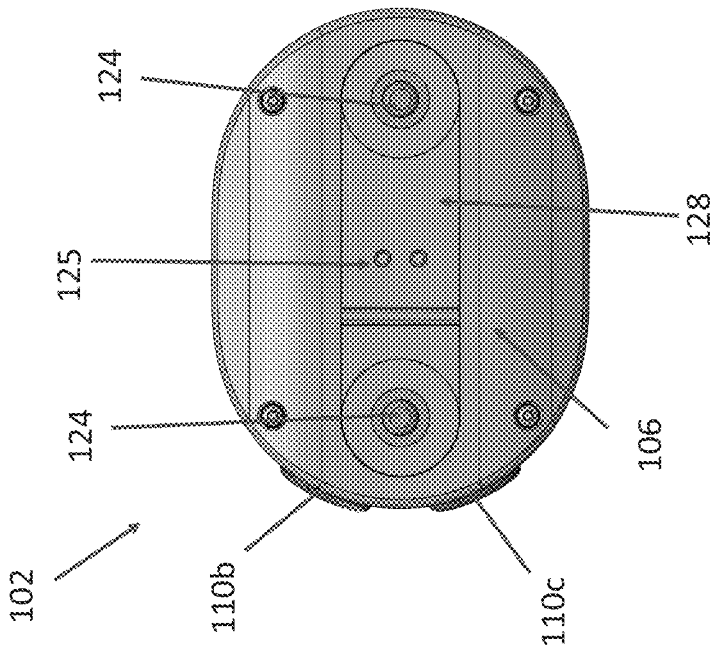
FIGS. 1A-1G schematically illustrate various views of an example of an enclosure configured for providing transcutaneous peripheral nerve stimulation.
Figure 1A:
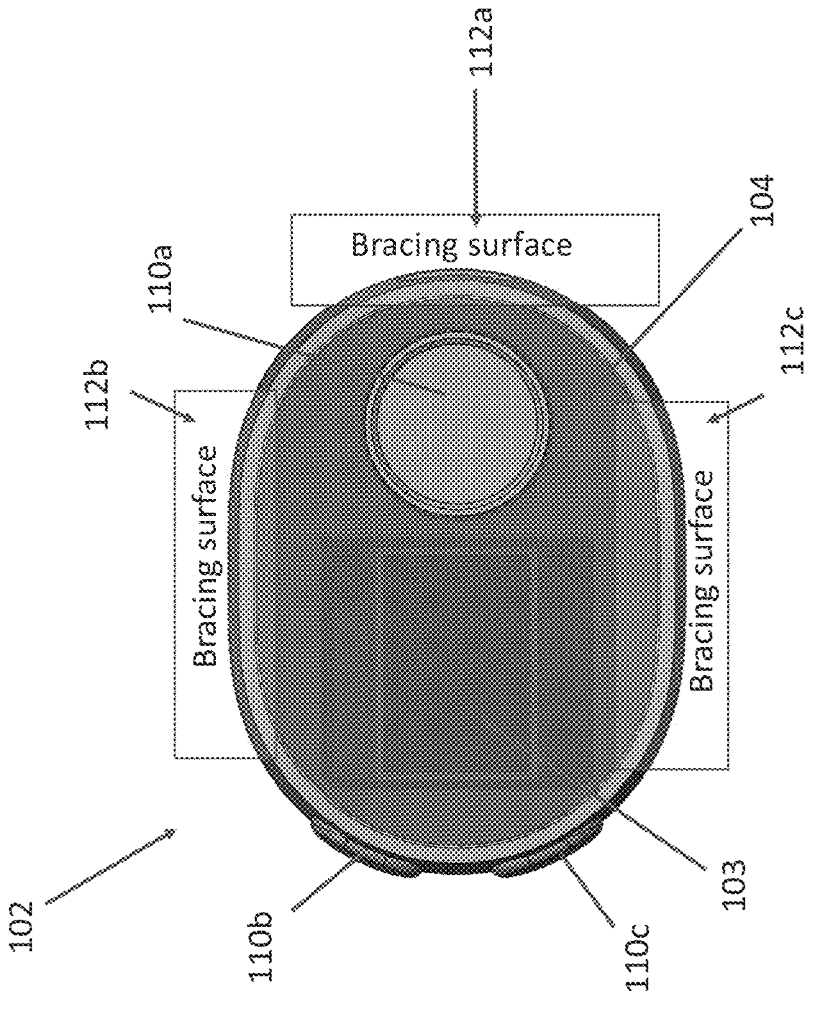
Figure 1C:
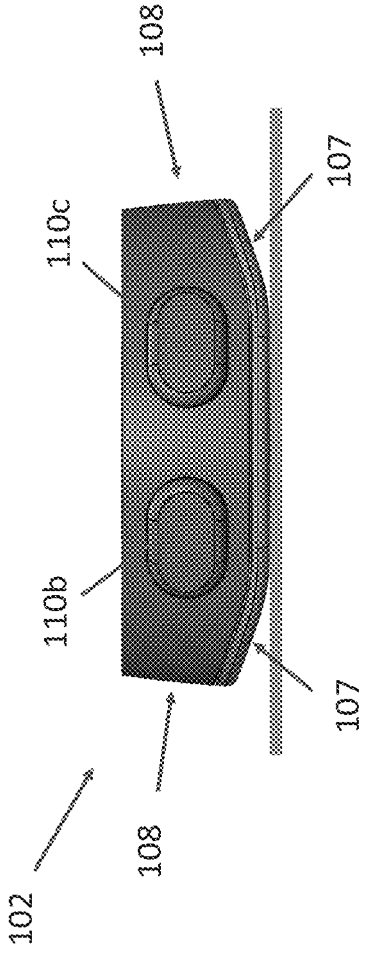
Figure 1D:
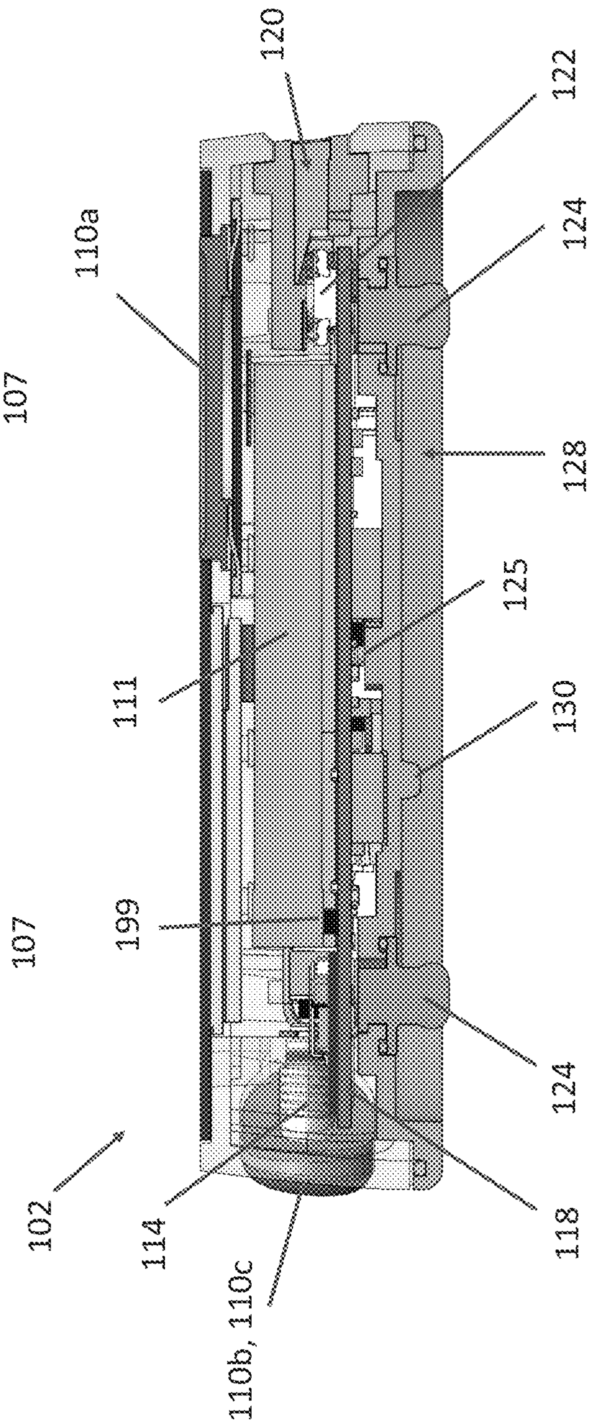
Figure 1E:
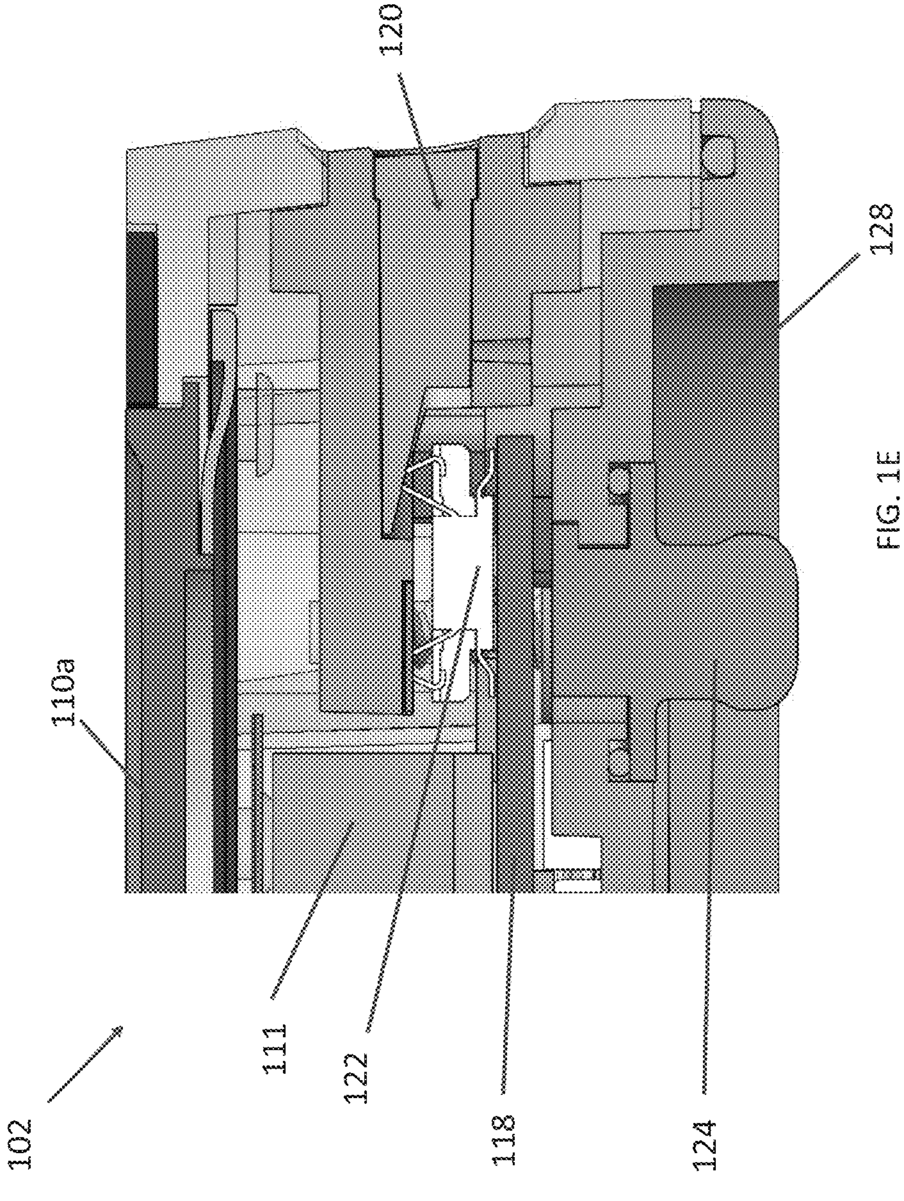
Figure 1G:
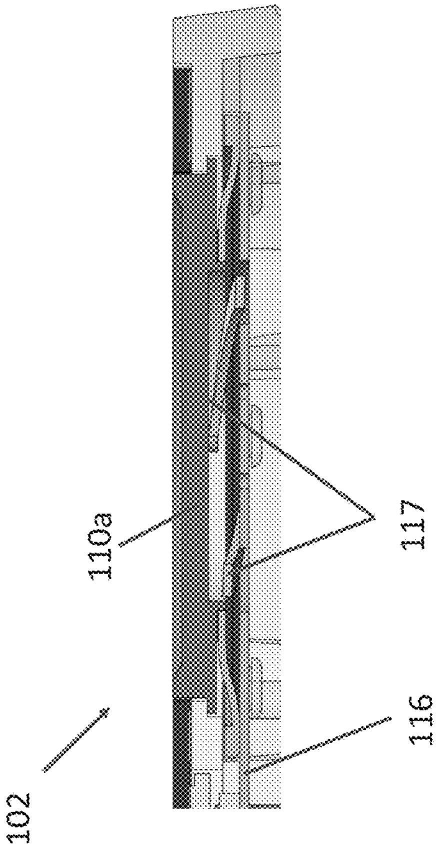
Figure 1F:
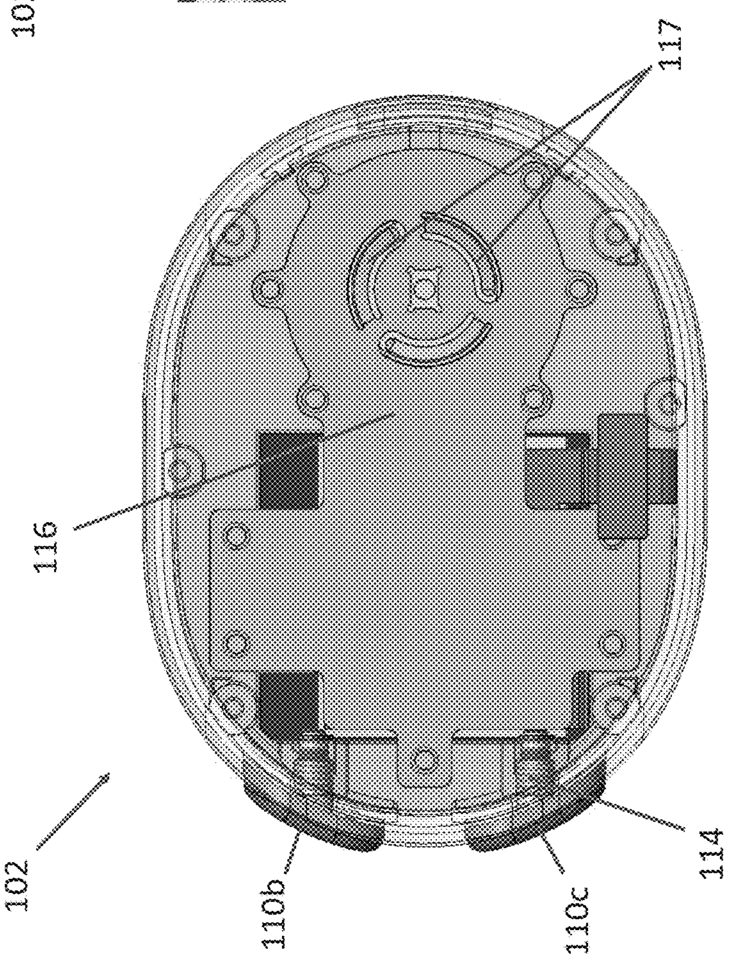

FIGS. 1A-1G depicts various views of an example of a body, housing, or enclosure 102 of a neurostimulation device 100. FIG. 1A depicts a top view of the enclosure 102. FIG. 1B depicts a bottom view of the enclosure 102 configured to face toward a skin surface of the user during neurostimulation. FIG. 1C depicts a side view of the enclosure 102. FIG. 1D depicts a cross-section of a side of the enclosure 102, which is substantially orthogonal to the side view depicted in FIG. 1B. FIG. 1E depicts a close-up view of the cross-section depicted in FIG. 1D. FIG. 1F depicts a top cross-section of the enclosure 102 including a spring feature. FIG. 1G shows a close-up view of the cross-section depicted in FIG. 1D including the spring feature shown in FIG. 1G. The enclosure 102 may have a top surface 104, as shown in FIG. 1A, and an opposing bottom surface 106, as shown in FIG. 1B. The enclosure 102 may have a sidewall 108 extending from the top surface 104 to the bottom surface 106 and defining a height of the enclosure 102. The top surface 104 and the bottom surface 106 may have substantially the same shape. For example, the top surface 104 and bottom surface 106 may be substantially rectangular, substantially oval, or an intermediate shape between a rectangle and an oval. For example, the surfaces 104, 106 may comprise a substantially round, oval, or elliptical/stadium-like shape, as shown in FIGS. 1A and 1B, or a rounded-corner rectangular or square shape. In other embodiments, the shape may be circular, triangular, polygonal, etc. The top surface 104 and the bottom surface 106 may have a length and a width, substantially transverse to the length. The length may be the same as the width or the length may be longer than the width. The top surface 104 and the bottom surface 106 may have substantially the same size. In some embodiments, the top surface 104 is slightly smaller than the bottom surface 106. For example, as shown in FIG. 1C, the profile of the top surface 104 may be slightly reduced in size relative to the bottom surface 106 and positioned over the bottom surface 106 such that the sidewall 108 or a portion of the sidewall 108 forms an angled or contoured surface extending between the top surface 104 and the bottom surface 106. In some embodiments, the top surface has a dimension (e.g., length, width, and/or thickness) is larger or smaller by about or less than about 20%, 15%, 10%, 9%, 8%, 7%, 6%, 5%, 4%, 3%, 2%, 1%, or less of a dimension (e.g., length or width) of the bottom surface, or ranges including any two of the foregoing values.

The sidewall 108 may extend slightly inward as it extends upward from the bottom surface 106 to the top surface, by a distance of about or less than about 20%, 15%, 10%, 9%, 8%, 7%, 6%, 5%, 4%, 3%, 2%, 1%, or less of a dimension (e.g., length or width) of the sidewall 108, or ranges including any two of the foregoing values. The top surface 104 may be positioned centrally over top of the bottom surface 106 such that the entire sidewall 108 is angled or contoured along all edges of the enclosure 102. The contoured sidewall 108 may cause the size of the enclosure to appear smaller than it actually is.

The top surface 104 may be flat or substantially flat. In some embodiments, the top surface 104 may be somewhat convex or concave. The bottom surface 106 may be substantially flat. In some embodiments, the bottom surface 106 may be somewhat convex or concave. For example, in some embodiments, as shown in FIG. 1C, the bottom surface 106 may have elevated or lifted edges 107 that are configured to extend above a central portion of the bottom surface 10 when the bottom surface 106 is resting on a flat surface. The lifted edges 107 may extend continuously (e.g., gradually) from a flat central portion of the bottom surface 106 to the edges of the bottom surface 106, In embodiments where the bottom surface comprises generally four edges, the bottom surface 106 may comprise 0, 1, 2, 3, or 4 lifted edges 107. In embodiments comprising two lifted edges 107, such as the embodiment shown in FIGS. 1A-1G, the two lifted edges 107 may be positioned substantially opposite each other. The lifted edges 107 may create lateral gaps between the bottom surface 106 and the surface the enclosure is resting on, such as a band and/or a body surface or body part of the user. The lateral gaps may create a grip space (e.g., finger space) and a portion of the bottom surface 106 by which a user can grip the enclosure 102. The grip space may facilitate the user detaching/removing the enclosure 102 from a band the enclosure is coupled to for allowing the user to wear the neurostimulation device 100. The lifted edges 107 may advantageously make the enclosure 102 appear visually smaller than it actually is. In other embodiments, the bottom surface 106 may be somewhat concave with edges that extend downward, such as to conform to the shape of a body part (e.g., a wrist) and aid in correctly positioning the device when worn. In some embodiments, the enclosure can take an oval shape and includes curved top and bottom surfaces, but does not include a separate sidewall.

The enclosure 102 may comprise a top member comprising the top surface 104 (or a majority thereof) and a bottom member comprising the bottom surface 106 (or a majority thereof). In some embodiments, the sidewall 108 may be formed as part of the top member and/or the bottom member. In some embodiments, the sidewall 108 may be formed from a separate shell component than the top member and the bottom member.

The enclosure 102 may be configured to enclose or contain the electronic circuitry for generating and providing a neurostimulation signal to be applied to the user. The circuitry may be self-contained in the enclosure 102 such that the neurostimulation device 100 is portable. The circuitry may include a pulse generator for generating an electrical stimulation pulse and a controller for controlling the delivery of the electrical pulses. The enclosure 102 may also comprise a power source, such as a battery. The battery may be rechargeable and/or replaceable. In some embodiments, the battery may be a standard form battery. In some embodiments, the battery may be a proprietary battery. The enclosure 102 may also contain one or more processors. The enclosure 102 may also contain memory. The enclosure 102 may be comprise one or more displays (e.g., digital displays, LEDs, etc.) to display information to the user, such as on a top surface of the enclosure 102. Displays may also be touch-sensitive to receive inputs from the user. The enclosure 102 may comprise one or more audio signal generators. The enclosure may comprise antennas for wireless communication, such as Bluetooth, WiFi or Zigbee. The enclosure may also comprise a haptic motor to provide feedback or notification to the wearer by vibration. The enclosure 102 may comprise one or more interface features 110, such as depressable or solid state buttons for example, by which a user may interface with the neurostimulation device 100. For example, the user may use the interface features 110, to input parameters into the neurostimulation device 100, select a neurostimulation program stored on the neurostimulation device 100, to power off/on the neurostimulation device 100, and/or to begin, stop, or pause a neurostimulation treatment. The neurostimulation device 100 may comprise one, two, three, four, five, or more than five interface features.

As shown in FIG. 1A, the enclosure 102 of the neurostimulation device 100 may comprise interface features or controls 110*a*, 110*b*, and 110*c*, which may be buttons, or touch-sensitive controls, dials, switches, or the like. The neurostimulation device 100 may comprise a first interface feature 110*a* on the top surface of the enclosure 102. The first interface feature 110*a* may be configured to start and stop neurostimulation. For instance, when pressed a first time, the first interface feature 110*a* may cause the neurostimulation device 100 to begin delivering a stimulation signal. When pressed a second time and held, the first interface feature 110*a* may cause the neurostimulation device 100 to cease delivering the neurostimulation signal. In some embodiments, the device could provide feedback such as visual, audible, or tactile (e.g., haptic feedback) upon activating a control, initiating or completing therapy, as an alarm when certain pre-determined criteria have been met, a vibration after a specific task is completed with the device, and the like. In some embodiments, the neurostimulation device 100 may deliver the neurostimulation signal indefinitely after the first interface feature 110*a* is activated. In some embodiments, the neurostimulation device 100 may be programmed to begin delivering a neurostimulation program (e.g., of a set duration of time or set number of pulses) after the first interface feature 110*a* is activated. In some embodiments, the duration of time could be about, at least about, or no more than about 5, 10, 15, 30, 40, 45, 60, 90, or 120 minutes, or ranges including any two of the foregoing values. In such embodiments, actuating (e.g., pressing) the first interface feature 110*a* again during the neurostimulation program may either pause or cancel the program. Actuating the first interface feature 110*a* a third time may resume or begin the neurostimulation program anew. Actuating the first interface feature 110*a* subsequently to completing the neurostimulation program may initiate another treatment session of the neurostimulation program. The first interface feature 110*a* may be a large button such that it is easy for the user to find and actuate. For instance, the first interface feature 110*a* may consume about, at least about, or no more than about 5%, 10%, 15%, 20%, 25%, 30%, 40%, 50%, or ranges including any two of the aforementioned values, or less than 5% or more than 50% the surface area of the top surface of the enclosure. The first interface feature 110*a* may be circular in shape, as shown in FIG. 1A, or any other suitable shape (e.g., oval, rectangular, square, etc.).

As shown in FIGS. 1A-1C, the enclosure 102 of the neurostimulation device 100 may comprise one, two, or more auxiliary interface features 110*b*, 110*c*. The auxiliary interface features 110*b*, 110*c* may be the same or different type of interface feature 110 as the first interface feature 110*a*. For example, the auxiliary interface features 110*b*, 110*c* may be buttons. The auxiliary interface features 110*b*, 110*c* may be positioned on a sidewall of the enclosure 102 or on the top surface of the enclosure. The auxiliary interface features 110*b*, 110*c* may be positioned substantially adjacent to one another on a same side of the enclosure 102. The auxiliary features 110*b*, 110*c* may be configured to enter additional input, to modulate one or more stimulation parameters, sense a parameter relating to the patient, and/or to cause a display on the enclosure 102 to display selected information, and/or control another function. For example, the auxiliary interface features 110*b*, 110*c* may be used to increment and/or decrement a stimulation session duration, a stimulation voltage and/or current (intensity), and/or to select a stimulation program, or other customized functionality.

The size and/or shape of the enclosure 102 may be configured to provide one or more suitable bracing surfaces 112 for the user to actuate the interface features 110*a*, 110*b*, 110*c*, as shown in FIG. 1A. For example, the various lateral surfaces of the sidewall 208 or lateral sides of the enclosure 102 may form bracing surfaces such as bracing surface 112*a*, 112*b*, 112*c*. The bracing surface 112*a* may be positioned substantially opposite the auxiliary interface features 110*a*, 110*b*. A user may brace his or her hand or one or more of his or her fingers against bracing surface 110*a* in order to advantageously provide a counter force that allows him or her to apply force in the direction of bracing surface 110*a* in order to actuate interface feature 110*b* and/or interface feature 110*c*. The bracing surfaces 110*b* and 110*c* may allow a user to apply slight compressive pressure to the enclosure 102 creating a frictional force which resists downward depression of the enclosure 102 and provides a counter force for the user actuating interface feature 110*a* by pressing it downward. The lifted edges 107 may be positioned under bracing surfaces 110*a*, 110*b* as shown in FIG. 1C, which may allow a user to exert an upward force on the enclosure and similarly provide a counter force which allows actuation of interface feature 110*a*. The user may similarly use any suitable outer portion of the enclosure, including top surface 104, as a bracing feature 112 to actuate the one or more interface features 104. In some cases, a bracing surface can have a dimension, such as a length or arc length of, for example, between about 20 mm and about 80 mm, between about 30 mm and about 70 mm, or between about 40 mm and about 60 mm. In some embodiments, a bracing surface can have a length or arc length of about, at least about, or no more than about 20 mm, 25 mm, 30 mm, 35 mm, 40 mm, 45 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 70 mm, 75 mm, or 80 mm, or ranges incorporating any two of the aforementioned values. In some embodiments, the length of a bracing surface can be about or at least about the length of a 95th percentile male thumb (e.g., about 58 mm), to provide stability for a majority of users of the device.

As shown in FIGS. 1D and 1F, the enclosure 102 may comprise springs 114 (e.g., coil springs) which bias the auxiliary interface features 114*b*, 114*c* laterally outward such that the buttons may be pressed inward against the force of the springs 114 and return to their pre-activated configuration when the pressure exerted by the user is released. In some embodiments, the first interface feature 114*a* may similarly be biased by a spring 114 biasing the first interface feature 114 upward. In some embodiments, the spring may be a cylindrical or annular foam or polymer element. In some embodiments, a different type of spring may be used. FIG. 1F depicts an example of a spring feature 116 which may enable actuation of the first interface feature 110*a*. The spring feature 116 may comprise a thin bracket. The bracket spring feature 116 may be secured (e.g., bolted or screwed) to an internal component of the enclosure 102 around a periphery of the bracket. The bracket spring feature 116 may comprise a relatively expansive surface area to distribute the force from the actuation of the first interface feature 114*a* across a large area of the enclosure. The bracket spring feature 116 may be cut to form one or more finger springs 117 beneath the first interface feature 114*a*. The finger springs 117 may have elongate bodies that are cut or separated from the body of the bracket spring feature 116 along three sides, including two opposing elongate sides. The spring fingers 117 may be somewhat arcuate. A plurality of spring fingers 117 may be arranged substantially uniformly around a circumference of a circle to evenly support the weight of first interface feature 114*a*. The spring fingers 117 may be configured to extend upward away from the otherwise flat body of the bracket spring feature 116. Downward pressure exerted by the user on the first interface feature 114*a* may compress the spring fingers 110 downward until the spring fingers 117 are aligned flat with the body of the bracket spring feature 117, which prevents further downward movement of the first interface feature 114*a*. The spring fingers 117 may return the first interface feature 114*a* to an upward position after pressure exerted by the user is released from the first interface feature 114*a*. The use of a relatively flat bracket spring feature 116 may minimize the height of the enclosure 102 and allow the neurostimulation device 100 to conveniently maintain a low-profile with respect to the surface of the user's body. In other embodiments, one or more of the controls need not be physically movable and instead respond to touch feedback (e.g., capacitive or resistive feedback). In some embodiments, the controls can respond to voice commands, gestures using motion sensors or cameras, and the like.

FIG. 1D schematically depicts at least some of the internal components housed within the enclosure 102. FIG. 1E illustrates a close-up view of the right side of FIG. 1D. The enclosure 102 may house a printed circuit board (PCB) 118 or equivalent circuitry. The enclosure 102 may include one or more charging ports 120 each configured to receive a charging pin, for example from a charger as described elsewhere herein, or an electrical stimulation contact from a charging cable. The enclosure 102 may comprise two charging ports 120 forming positive and negative terminals. FIGS. 1D and 1E illustrate an example of an enclosure comprising two charging ports 120 (one charging port 120 being hidden from view behind the other). In some embodiments, the enclosure may include a third charging port 120 (e.g., a ground port). In some embodiments, the enclosure can include one, two, or more ports to facilitate communications, such as a 1-wire interface for example. In some embodiments, the enclosure 102 may comprise an inductive coil for wirelessly powering a rechargeable battery 111. The charging ports 120 may be electrically connected to a rechargeable battery 111 via an electrical connector 122. The electrical connector 122 may be coupled to the PCB 118. In some embodiments, the same electrical connector 122 may electrically connect the first interface feature 114*a* to the PCB 118. The dual purpose of the electrical connector 122 may significantly simplify the manufacturing (e.g., the labor and cost) of the neurostimulation device 100. Some configurations as illustrated and described advantageously do not require the size of the enclosure to be increased.

As depicted in FIGS. 1B, 1D, and 1E, the enclosure 102 may include two or more electrical stimulation contacts 124 for delivering or transferring the electrical stimulation signal to the user or a downstream interface member. The electrical stimulation contacts 124 may be positioned on the bottom surface 106 of the enclosure 102. The electrical stimulation contacts 124 may include one electrical stimulation contact 124 for each electrode to be applied to the user. The electrical stimulation contacts 124 may include at least one electrical stimulation contact 124 for each nerve that is to be stimulated. For example, the electrical stimulation contacts 124 may include an electrical stimulation contact 124 configured to deliver a signal to the median nerve, the radial nerve, the ulnar nerve or any combination thereof. In some embodiments, stimulation may alternate between each nerve such that the nerves are not stimulated simultaneously. In some embodiments, all nerves are stimulated simultaneously. In some embodiments, stimulation is delivered to the various nerves in one of many bursting patterns. The stimulation parameters may include on/off, time duration, intensity, pulse rate, pulse width, waveform shape, and the ramp of pulse on and off. In one preferred embodiment the pulse rate may be from about 1 to about 5000 Hz, about 1 Hz to about 500 Hz, about 5 Hz to about 50 Hz, about 50 Hz to about 300 Hz, or about 150 Hz. In some embodiments, the pulse rate may be from 1 kHz to 20 kHz. A preferred pulse width may range from, in some cases, 50 to 500 μs (microseconds), such as approximately 300 μs. The intensity of the electrical stimulation may vary from 0 mA to 500 mA, and a current may be approximately 1 to 11 mA in some cases. The electrical stimulation can be adjusted in different patients and with different methods of electrical stimulation. The increment of intensity adjustment may be, for example, 0.1 mA to 1.0 mA. In one preferred embodiment the stimulation may last for approximately 10 minutes to 1 hour, such as approximately 10, 20, 30, 40, 50, or 60 minutes, or ranges including any two of the foregoing values. In some embodiments, a plurality of electrical stimuli can be delivered offset in time from each other by a predetermined fraction of multiple of a period of a measured rhythmic biological signal such as hand tremor, such as about ¼, ½, or ¾ of the period of the measured signal for example. Further possible stimulation parameters are described, for example, in U.S. Pat. No. 9,452,287 to Rosenbluth et al., U.S. Pat. No. 9,802,041 to Wong et al., PCT Pub. No. WO 2016/201366 to Wong et al., PCT Pub. No. WO 2017/132067 to Wong et al., PCT Pub. No. WO 2017/023864 to Hamner et al., PCT Pub. No. WO 2017/053847 to Hamner et al., PCT Pub. No. WO 2018/009680 to Wong et al., and PCT Pub. No. WO 2018/039458 to Rosenbluth et al., each of the foregoing of which are hereby incorporated by reference in their entireties. In some embodiments, the device can also be configured to deliver magnetic, vibrational, mechanical, thermal, ultrasonic, or other forms of stimulation instead of, or in addition to electrical stimulation. However, in some embodiments, the device is configured to only deliver electrical stimulation, and is not configured to deliver one or more of magnetic, vibrational, mechanical, thermal, ultrasonic, or other forms of stimulation instead of, or in addition to electrical stimulation. The neurostimulation device 100, such as that depicted in FIGS. 1A-1G or others for example may include electrical stimulation contacts 124 configured to transcutaneously stimulate the median, ulnar, and/or radial nerves for example. As shown in FIG. 1B, the enclosure may also include an optional return contact 125 for dispersing stimulation current from the body by returning to the stimulation source. Each contact 124, 125 may comprise one or more conductive pins or projections extending from the insulated enclosure 102. The contacts 124, 125 may be in electrical communication with the PCB 118. The bottom surface 106 may include a recess 128 configured to receive and mechanically couple to an interface member as described elsewhere herein. The recess 128 may encompass all the electrical contacts 124, 125. The recess may be round, oval, elliptical/stadium shaped, as shown in FIG. 1B, or any other suitable shape. The electrical stimulation contacts 124 may be snap connections which form snap fits (e.g., annular snap fits) with corresponding contacts on an interface member comprising the electrodes to be applied to the user's skin. Other reversible connection mechanisms to connect the enclosure to the stimulation contacts can be utilized as well, including but not limited to magnets, screws, rotatable/rotational connection elements, an elastomer, and the like. The enclosure 102 and/or electrical connections may be configured such that the electrical stimulation contacts can be twisted into place within the enclosure 102. The electrical stimulation contacts 124 may be heat staked to the plastic enclosure 102, adhered to the enclosure 102 with a suitable adhesive, or otherwise firmly coupled or attached to the enclosure 102 by any suitable means known in the art. The electrical stimulation contacts 124 may be aligned with an axis extending the length of the enclosure 102. The axis may be centrally aligned along the enclosure 102. The ground contact 125 may be collinear with the electrical stimulation contacts 124. In some embodiments, the electrical stimulation contacts 124 may be spatially configured to stimulate the median, ulnar, and/or radial nerves, either in-line along the long axis of the patient's extremity, or circumferential around the band depending on the desired clinical result. In some embodiments, the electrodes corresponding to the electrical contacts 124 may be configured to be in electrical communication with the electrical contacts although arranged in a different spatial arrangement than the electrical contacts 124.

Figure 2A:
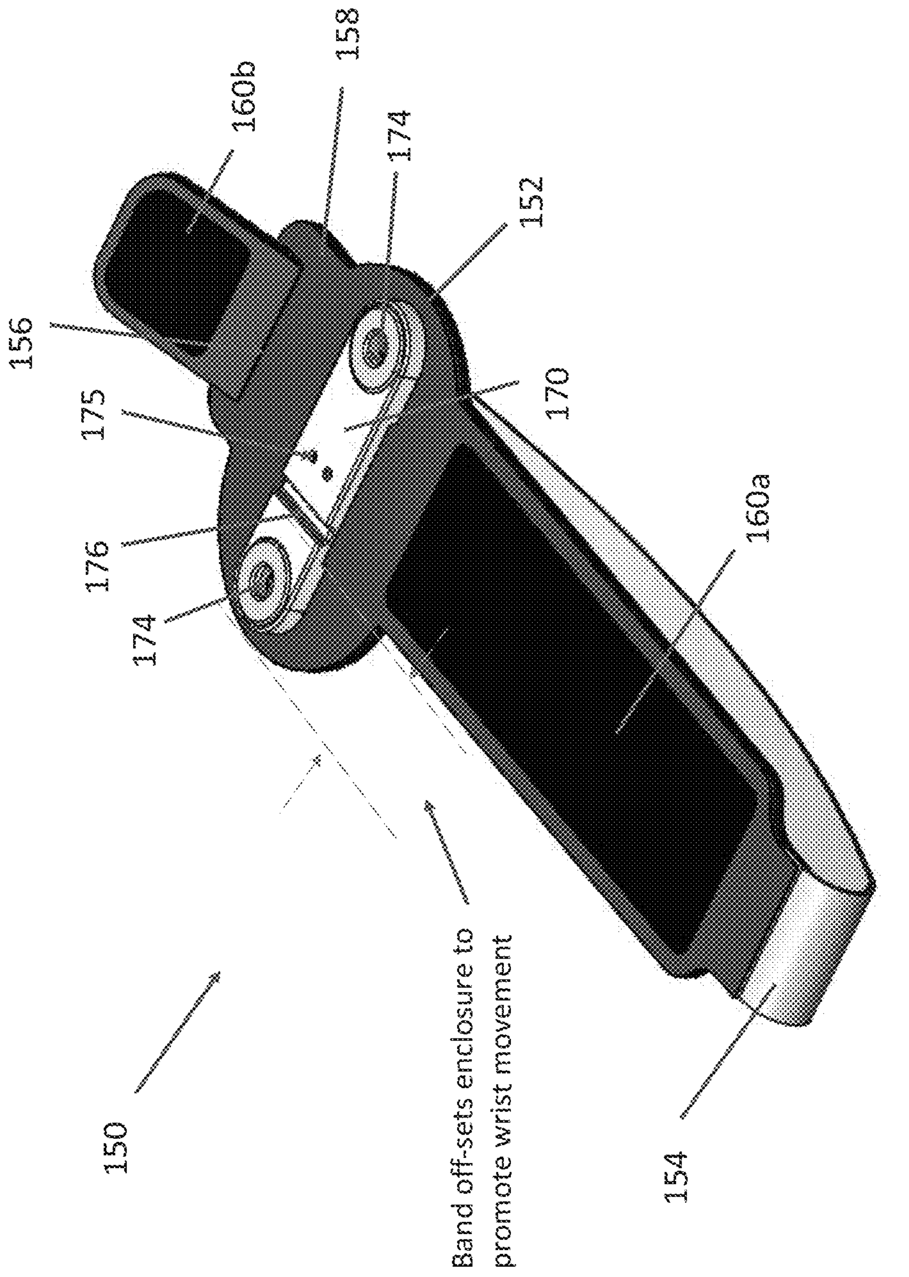
FIGS. 2A-2B schematically illustrate various views of an example of a band configured to be worn by a user and to detachably couple to the enclosure for providing transcutaneous peripheral nerve stimulation to the user.
Figure 2B:
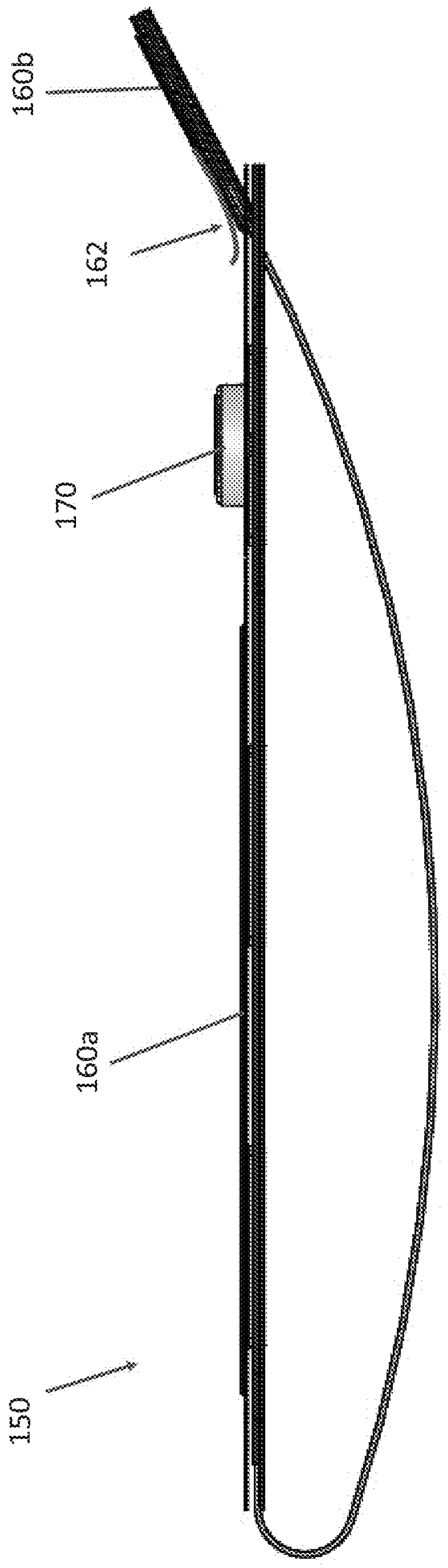

The enclosure 102 may be configured to be coupled to the surface of a user's skin for transcutaneous stimulation using a band 150. The electrodes could be percutaneous or microneedle electrodes in other embodiments, or only transcutaneous (e.g., not percutaneous, microneedles, or implanted electrodes in some embodiments). FIGS. 2A and 2B illustrate an example of a band 150 configured to be mechanically and electrically coupled to the enclosure 102 of FIGS. 1A-IG. The band 150 may be configured to be worn by a user around his or her arm, wrist finger, leg, ankle, knee, waist, etc. The band 150 may be configured to hold the enclosure 102 close to the user. In some embodiments, the band 150 may be configured as a D-shaped loop as shown in FIGS. 2A and 2B. The band 150 may comprise a base section 152 shaped and sized to sit underneath the enclosure 102. The band 150 may comprise a strap 154 extending from one side of the enclosure 102. In some embodiments, the strap 154 may have an adjustable length that is sufficient to accommodate any size user. In some embodiments, the strap 154 may be sized for various sizes of users (e.g., small, medium, large, child, adult, etc.). The strap 154 may have a width parallel to the length of the enclosure 102 and the base 12. The width of the strap 154 may be less than the length of the enclosure 102 and/or the corresponding length of the base 152. The length (the longer dimension) of the enclosure 102 may be oriented substantially perpendicular to the length of the strap 152 and may be configured to align the length of the enclosure 102 with the length of the user's arm, leg, or other body appendage. The alignment of the length of the enclosure 102 with the length of the body part may facilitate easier movement of the body part, such as the hand and wrist, while the neurostimulation device 100 is being worn and may be generally less protrusive and awkward and, therefore, less likely to snag or inadvertently contact something in the user's environment. In some embodiments, the strap 154 may be positioned substantially centrally along the length of the enclosure 102 and/or base 152. In some embodiments, as illustrated in FIG. 2A, the strap 154 may be offset toward or near one side of the length of the enclosure 102 and/or base 152, preferably offset in a proximal direction relative to the wearer's limb. Offsetting the strap 154, may allow the strap 154 to be worn around, for example, the wrist of the user and the enclosure 102 to extend upward or proximally from the wrist in the direction of the shoulder rather than distally, or in the direction of the hand, which may beneficially allow or promote wrist movement (e.g., a larger range of motion).

The side of the base 152 of the band 150 opposite the strap 154 may comprise an aperture 156 (e.g., a D-loop) configured to receive the strap 154. The aperture 156 may be formed on a tab 158 extending from the base 152. The effective length of the strap 154 may be adjusted by pulling the strap further through the aperture 156. In some implementations the base 152, strap 154, and tab 158 of the band 150 may be fabricated as a single flat piece of flexible material. Fabricating these portions as a single piece of material may simplify the manufacturing process. Complementary sections of hook and loop fasteners 160 (e.g., Velcro™) may be attached to the strap 154 for allowing the strap 154 to form a closed loop of an adjustable length for securing the band 150 to the user, for example around the user's arm, wrist, or leg. In some implementations, the band 150 may be fabricated by attaching the sections of hook and loop fasteners 160*a*, 160*b* to the strap after the strap has been received through the aperture 156. The strap 154 may comprise a large width portion and a small width portion. The small width portion may be configured to be received through the aperture 156. In some embodiments, one of the complementary sections of hook and loop fasteners 160*a* is attached to the large width portion (e.g., adjacent to the base 152) and the other section 160*b* is attached to the small width portion (e.g., at the free end of the strap 154). In some embodiments, the complementary hook and loop sections 160*a*, 160*b* may be affixed on the same side of the strap 154. For example, both sections 160*a*, 160*b* may be affixed to the outer surface of the strap 154, as shown in FIG. 2A. The free end of the strap 154 may be wrapped over the enclosure 102 to join the complementary hook and loop sections 160*a*, 160*b* together. In some embodiments, the section 160*a* adjacent the base 152 may be affixed to the outer surface of the strap 154 and the section 160*b* at the free end of the strap 154 may be affixed to the inner surface of the strap 154, such that after looping through the aperture 166, the free end may double back on the strap to join the complementary hook and loop sections 160*a*, 160*b* together. The relative positioning of the complementary hook and loop sections 160*a*, 160*b* may be used to tighten or adjust the loop on the user's body.

In some embodiments, the hook and loop section 160*b* may be configured to prevent or inhibit the free end of the band 154 from retreating through the aperture 156. For instance, as schematically depicted in FIG. 2B, the hook and loop section 160*b* may comprise a locking flap 162 extending from one side of the section configured to mechanically lock the free end on the outer surface of the band 150. An advantage of the locking flap on one side (e.g., only one side) is that the free end of the band can be easily inserted through the aperture, but cannot easily be removed or fall out when the user is donning the band. The flap requires a more intentional task of the user to remove, making the donning experience easier. The locking flap 162 may be a piece of the hook and loop section 160*b* material which is not adhered or affixed to the strap 154. The locking flap 162 may be an additional piece of material which is attached (e.g., sewn) onto the end of the hook and loop section 160*b* material. In some embodiments, the locking flap 162 may extend from a side of the hook and loop section 160*b* positioned opposite the free end of the strap 154, as shown in FIG. 2B. In some embodiments, the locking flap 162 may extend in a direction opposite the free end of the strap 154, as shown in FIG. 2B. In some embodiments, the locking flap 162 may extend from a side of the hook and loop section 160*b* positioned closest to the free end of the strap 154. In some embodiments, the locking flap 162 may extend in a direction toward the free end of the strap 154 (and possibly beyond the free end). In some embodiments, the hook and loop section 160*b* may comprise multiple locking flaps 162, such as a flap 162 extending from a side opposite the free end and extending away from the free end and a flap 162 extending from a side closest to the free end and extending toward the free end.

In some embodiments, the band 150 comprises an interface member 170 configured to mechanically and/or electronically interface with the electrical contacts 124, 125 protruding from the enclosure 102. FIGS. 2A and 2B depict an interface member 170 coupled to the base 152 of the band 150 and extending upward from an outer surface of the band 150. The interface member 170 may substantially mirror a portion of the bottom surface 106 comprising the electrical contacts 124, 125, as seen in FIG. 1B. For instance, the interface member 170 may comprise electrical contact ports 174*a*, 174*b* configured to receive and electrically connect to the electrical stimulation contacts 124*a*, 124*b* of the enclosure 102 and electrical contact port 175 configured to receive and electrically connect to the ground contact 125 of the enclosure 102. In some embodiments, the electrical contacts may also provide a mechanical connection between the band and the enclosure. In some embodiments, electrical contacts are metallic, electrically conductive snap fasteners to provide a mechanical connection. The snap fasteners are comprised of a pair of interlocking discs made of metal where a circular tip under a first disc on the bottom surface of the enclosure that fits into a groove on the top surface of the second disc on the interface member of the band. The tip of the first disc is inserted into the groove of the second disc, holding the discs together until a certain amount of force is applied for removal. In some embodiments, the interface member does include a discrete cable connector. In alternative embodiments, the interface member 170 may comprise protruding electrical contacts and the enclosure 102 may comprise recessed electrical contacts or some of the electrical contacts on each the interface member 170 and the enclosure 102 may be protruding and some may be recessed. The device can also include one, two, three, or more sensors 199, which can include any number of combination of inertial measurement units (IMUs) single or multi-axis accelerometers, gyroscopes, inclinometers (to measure and correct for changes in the gravity field resulting from slow changes in the device's orientation), magnetometers; fiber optic electrogoniometers, optical tracking or electromagnetic tracking; electromyography (EMG) to detect firing of tremoring muscle; electroneurogram (ENG) signals; cortical recordings by techniques such as electroencephalography (EEG) or direct nerve recordings on an implant in close proximity to the nerve; heart rate or HRV sensors, galvanic skin response sensors, thermocouples, and/or other physiologic sensors, for example. While sensors 199 are shown schematically proximate the PCB 118 and battery 199, one or more sensors may be placed in other desired areas and proximate any of the illustrated and disclosed elements in some cases.

The interface member 170 may be configured (e.g., shaped and sized) to be received in the recess 128 of the enclosure 102. For example, the interface member may have any appropriate shape including those described elsewhere herein and a height matched to the depth of the recess 129. The interface member 170 may form a reversibly detachable interference fit or snap fit with the recess 128. In some embodiments, the interface member 170 may comprise a recess and the enclosure may comprise a projection. Positioning the protruding electrical contacts 124, 125 within the recess 128 may advantageously protect the electrical contacts 124, 125 from damage. In some embodiments, the enclosure 102 and the interface member 170 may comprise corresponding keying features which ensure the enclosure 102 and the interface member 170 are coupled in an appropriate orientation. For example, the enclosure 102 may comprise a ridge 130 extending from the bottom surface 106. The ridge 130 may be positioned between the electrical stimulation contacts 124. The ridge 130 may be positioned asymmetrically relative to the electrical stimulation contacts 124. The interface member 170 may comprise a channel 176 configured (e.g., sized and shaped) to receive the ridge 130. The keying features may ensure, for example, that the electrical stimulation contacts 124 are connected to the proper electrical contact ports 174 and not reversed. The keying features may be particularly advantageous for embodiments where the electrical contacts 124, 125 form a symmetric arrangement, as shown in FIG. 1B. The keying features may ensure that the proper stimulation signal is electrically coupled to the proper electrode and, correspondingly, the proper nerve, and prevent the device from being worn on the wrong hand (e.g., right or left hand).

Any suitable mechanical coupling mechanism may be used to attach the enclosure to the band 150. The base 152 of the band 150 may comprise an aperture through which the interface member 170 extends upward from the outer surface of the band 150. The interface member 170 may be attached to the base 152 by any suitable means, such as an adhesive or permanent or removable mechanical fastener. The inner side of the interface member 170 may comprise electrodes or electrical contacts configured for transcutaneously stimulating the user. As described elsewhere herein, in some embodiments, there may be one electrode for each electrical stimulation contact 124. There may be one electrode for the ground contact 125. In some embodiments, the electrodes may be spatially arranged in the same manner as the electrical contacts 124, 125. In some embodiments, the electrodes may be arranged differently. For example, the electrodes may be arranged in a line substantially perpendicular to the line along which the electrical contacts 124, 125 are arranged, such that the electrodes are positioned, either axially and/or at least partially around a circumference of a body part (e.g., a wrist). In some embodiments, the electrodes may be configured to be generally in-line with the axon(s) of the target nerve being stimulated.

Figure 3B:
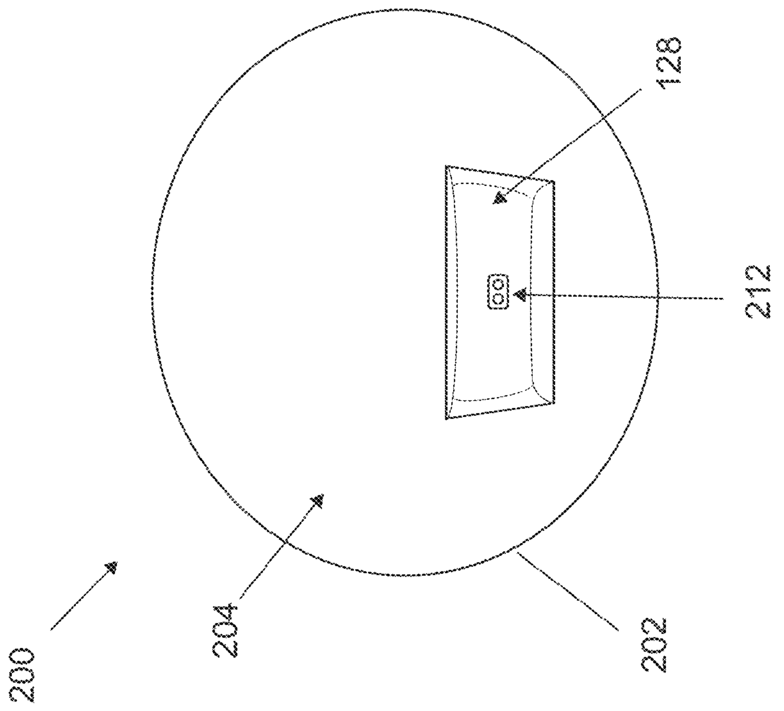
FIGS. 3A-3F schematically illustrate various views of an example of a charger configured to hold and receive a neurostimulation device for charging the neurostimulation device.
Figure 3A:
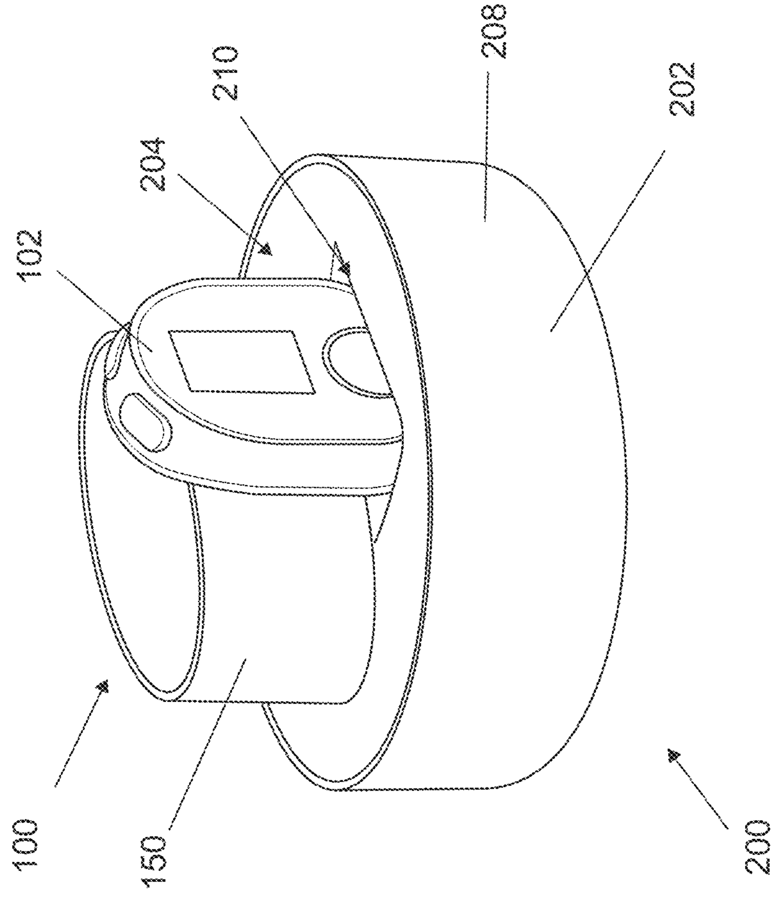
Figure 3C:
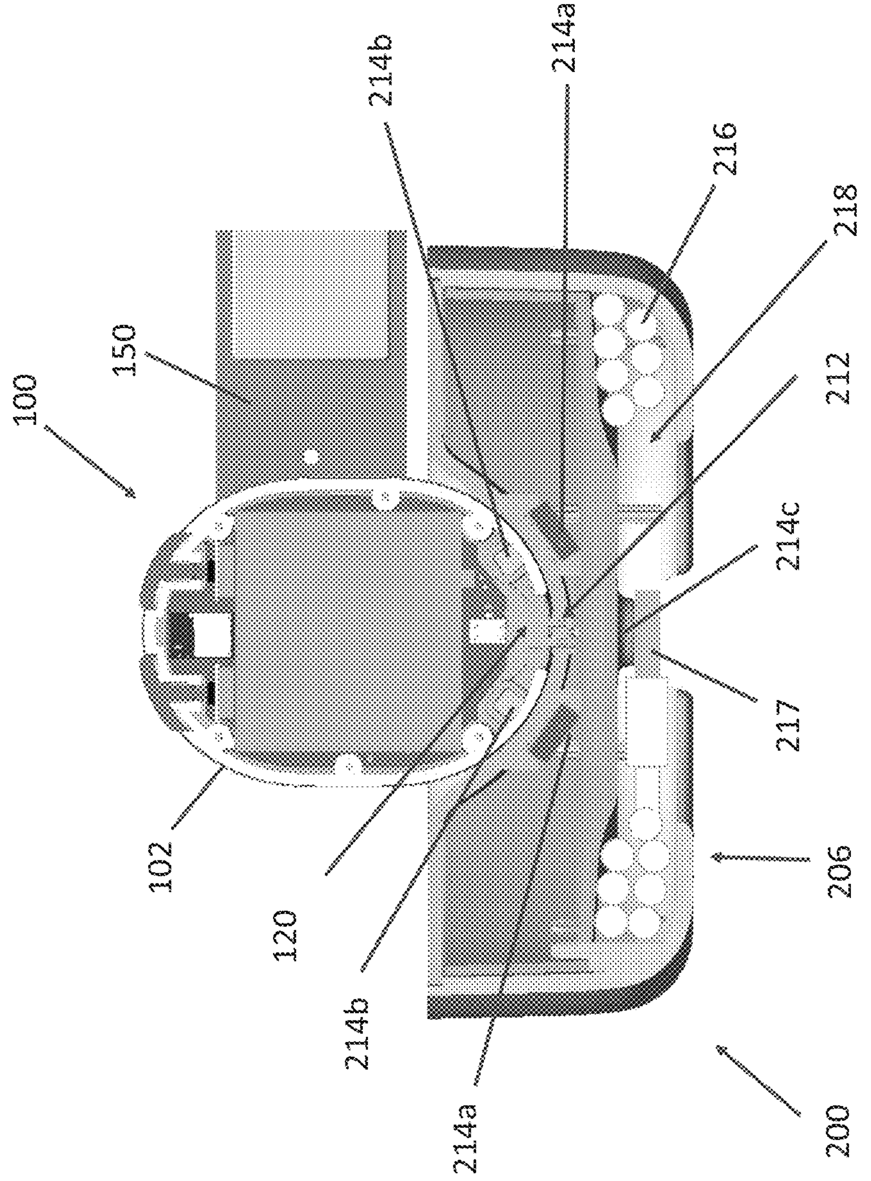
Figure 3E:
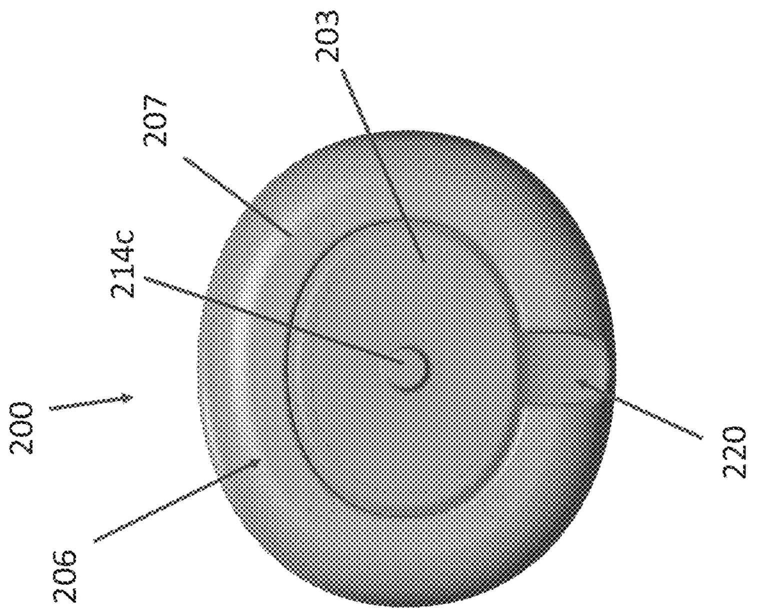
Figure 3D:
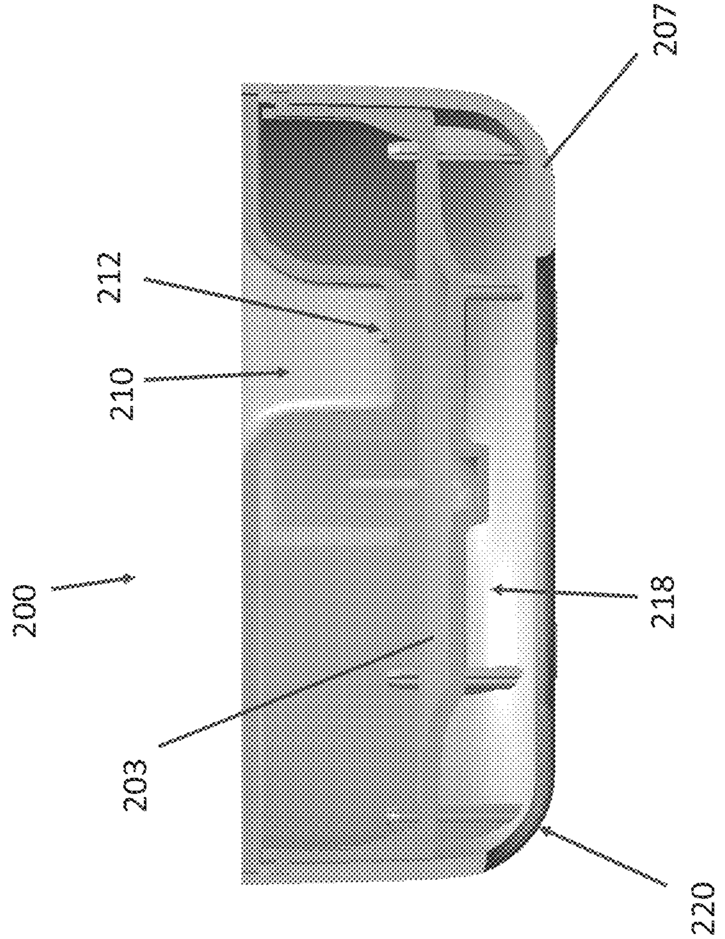
Figure 3F:
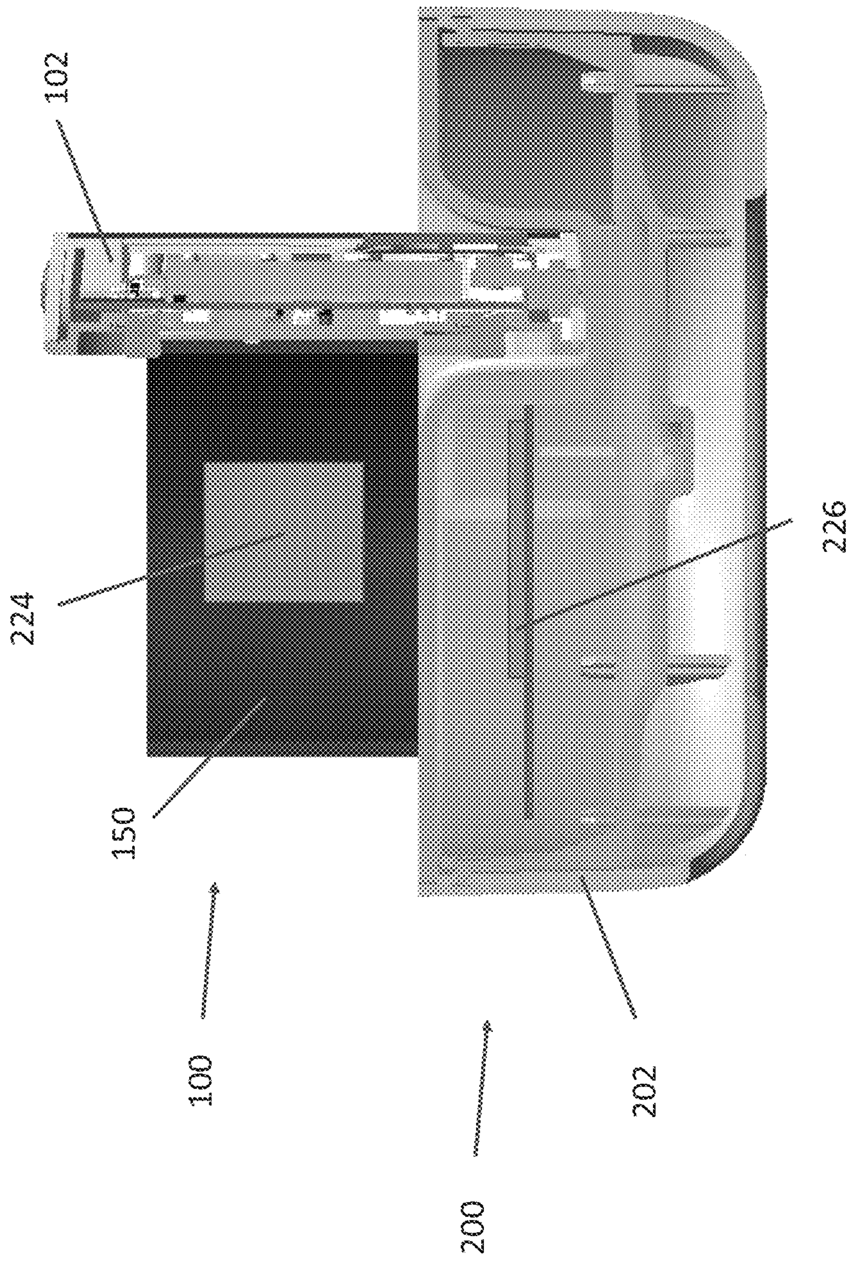

Disclosed herein is also a charger 200 configured for charging the neurostimulation device 100. FIGS. 3A-3F schematically depict an example of a charger 200. FIG. 3A illustrates a perspective view of the charger 200 holding/charging the neurostimulation device 100. FIG. 3B depicts a top view of the charger 200. FIG. 3C depicts a cross-section of a side of the charger 200 holding/charging the neurostimulation device 100. FIG. 3D depicts a cross-section of a side of the charger 200 which is substantially orthogonal to the side depicted in FIG. 3C. FIG. 3E illustrates a bottom view of the charger 200. FIG. 3F depicts a cross-section of the same side of the charger 200 as depicted in FIG. 3D but includes the neurostimulation device 100. The charger 200 may comprise a base receptacle 202 configured to receive and hold the neurostimulation device 200 while it recharges a rechargeable power source contained within the enclosure 102 of the neurostimulation device 100. The charger 200 may have a top surface 204, a bottom surface 206, and a sidewall 208. The top surface 204 and/or the bottom surface 206 may be substantially circular, round, or any other suitable shape. The charger 200 may generally be somewhat cylindrical. The charger 200 may comprise a rounded edge between the bottom surface 206 and the sidewall 208.

As seen in FIG. 3B, the top surface 204 of the charger 200 may comprise a pocket 210 configured to receive and hold the device 100 for charging. The pocket 210 of the charger 200 may be configured to hold the neurostimulation device 100 in a substantially upright position in which length of the enclosure 102 is substantially normal to a top surface 204 of the charger 200. The charger 200 may be configured to orient the top surface 104 of the enclosure 102 radially outward from the center of the charger 200 and the bottom surface 106 radially inward toward the center of the charger. The depth of the pocket 210 may be any sufficient depth for stably holding the enclosure 102 in place. In some embodiments, the depth of the pocket 210 may be configured such that when the enclosure 102 is fully inserted into the pocket 210, the band 150 may rest on the top surface 204 of the charger 200 when the band 150 is attached to the enclosure 102. The configuration also may allow the band 150 to support the enclosure 102 location. In some embodiments, the band 150 may facilitate holding the enclosure 102 in an upright position. An advantage of keeping the enclosure in an upright position is that the enclosure pins maintain good contact with the charging pins in the charger. The enclosure 102 may also be charged while the band 150 is not attached to the enclosure 102. The top surface 204 may be substantially flat for supporting the band 150. The pocket 210 may be positioned off the center of the top surface 204 of the charger 200 to leave space for the top surface 204 to accommodate the band 150. In some embodiments, the space for the band 150 may help the user properly orient the enclosure 102 when placing the enclosure 102 in the pocket 210. The pocket 210 may have a somewhat funneled or tapered opening such that the top face of the pocket 210 formed at the top of the pocket 210 on the top surface 204 is slightly larger than the bottom face of the pocket 210 formed at the bottom of the pocket 210. The sidewalls of the pocket may gradually taper inward from the top face of the pocket 210 to the bottom face of the pocket 210. In some embodiments, the taper is primarily or entirely concentrated at the top of the pocket 210. The taper may be advantageous for guiding the enclosure 102 into the pocket 210 such that the user does not need to as precisely target the pocket 210 as if the top face were sized to mirror the size of the enclosure 102. The bottom of the pocket 210 may more precisely match the size of the enclosure 102 to firmly hold the enclosure in place, which can advantageously provide a more reliable connection to the charging pins. In some embodiments, the band and/or enclosure does not include a discrete removable cable connector to connect to the charger.

As shown in FIG. 3B, the bottom face of the pocket 210 may comprise one or more charging pins 212. The charging pins 212 may be configured (e.g., sized and shaped) and spaced to be received in the charging ports 120 of the enclosure 102. The charger 200 may be configured such that the charger automatically begins charging the enclosure 102 when the charging pins 212 are electrically coupled to the charging ports 120. In some embodiments, there may be two charging pins 212, such as a charging pin 212 forming a positive terminal and a charging pin 212 forming a negative terminal. In some embodiments, there may be an optional ground pin. In some embodiments, the enclosure can include one, two, or more ports to facilitate communications, such as a 1-wire interface for example as previously described. As shown in FIG. 3C, the charger 200 may comprise one or more magnets 214*a* and the enclosure 102 may comprise one or more magnets 214*b*. The magnets 214*a* of the charger 200 may be paired with and complementary with (opposite polarity) the magnets 214*b* of the enclosure 102. In some embodiments, ferrous metal can be present in the enclosure 102 instead of magnets 214*a* to advantageously reduce weight in a wearable (e.g., wrist-worn device) and prevent attracting other ferrous metallic objects when worn. There may be 0, 1, 2, 3, 4, 5, or more than 5 pairs of magnets 214*a*, 214*b*. In some embodiments, as shown in FIG. 3C, there may be two pairs of magnets 214*a*, 214*b* positioned across the width of the enclosure 102 and corresponding width of the pocket 210. The two pairs of magnets 214*a*, 214*b* may surround the charging pins 212. The pairs of magnets 214*a*, 214*b* may be arranged symmetrically across the enclosure 102 and the pocket 210. The magnets 214*a* may be positioned on or just underneath the surface of the pocket 210, as shown in FIG. 3C. The magnets 214*b* may be positioned on or just underneath the surface of the enclosure 102, as shown in FIG. 3C. The magnets 214*a*, 214*b* may ensure proper alignment of the charging ports 120 with the charging pins 212. The force between the pairs of magnets 214*a*, 214*b*, may be configured to stably hold or facilitate holding the enclosure 102 in place while allowing for release/removal of the enclosure by reasonable force applied from the user. In some embodiments, the magnets 214*a*, 214*b* may be strong enough to hold the enclosure 102 within the pocket 210 even when turned upside down. The use of magnets 214*a*, 214*b* may reduce the depth of the pocket 210 which is sufficient to firmly hold the enclosure 102 and may thereby reduce an overall height and size of the charger 200. In some embodiments, the charger includes user interface elements that indicate to the user that the enclosure is in good connection with the charger to charge the battery. In some embodiments, the user interface elements are LED lights. In some embodiments, the enclosure screen displays an icon and/or text to communicate that the device is properly charging.

As shown in FIG. 3C, the charger 200 may comprise a charging cable 216 for drawing power from an external power source, such as, for example, an AC power outlet, or a computer or laptop device. The power cable 116 may be permanently attached to the base receptacle 202 at the point where it is electrically connected. In some embodiments, a strain relief feature is included on the permanently attached power cable at the point where it is electrically connected, having the advantage of preventing disconnection of the power cable when a force is applied to the cable. In some embodiments, the charger is connectable to the neurostimulation device (e.g., band and/or enclosure) via a connection element that does not comprise a cable. In some embodiments, the power cable 116 may be detachably connectable to the base receptacle 202 at the point where it electrically connects to the base receptacle 202. As shown in FIG. 3C, the charging cable 216 may be a USB cable configured to receive power from a device comprising a USB port. The charger 200 may comprise a magnet 214*c* configured to magnetically hold in place a charging port 217 of the charging cable 216, such as in a compact position, when the charger 200 is not being used. Magnet 214*c* could be a discrete magnet from magnets 214*a*, 214*b*, or combined as part of the same magnet of 214*a*, 214*b* in some embodiments to advantageously reduce weight. The magnet 214*c* may have both positive and negative poles (not shown). The charging port 217 or a portion thereof may be metallic (e.g., a ferrous metal) such that it can be attracted to the magnet 214*c*. The charging port 217 may be easily released from the hold of the magnet 214*c* using nominal force by the user.

As shown in FIGS. 3C and 3D, the base receptacle 202 may comprise a hollow charging cable pocket 218 configured to store the charging cable 216 when it is not in use. The charging cable pocket 218 may comprise a bottom portion of the base receptacle 202. For example, the bottom surface 206 may be substantially opened, at least along a central portion of the bottom surface 206 for receiving the charging cable 216. The bottom surface 206 may comprise a rim 207 that surrounds the entire perimeter or at least a portion of the perimeter of the bottom surface 206 for facilitating retention of the charging cable 216 in a stored position, as seen in FIG. 3E. The stored position may comprise the charging cable wrapped or coiled around a center of the base receptacle 202. In some embodiments, the height of the charging cable pocket 218 may be greater along an outside perimeter than along the center of the pocket 218 in order to promote storage of the charging cable 216 along the outside perimeter, as seen in FIG. 3C. The charging cable pocket 218 may be configured (e.g., sized) such that the entire charging cable 216 may fit within the pocket 218 without extending across or below the bottom surface 206 such that the base receptacle 202 may sit flat on a surface when the charging cable 216 is in a stored position. In some embodiments, the rim 207 may comprise an exit 220, as seen in FIG. 3E, or opening in the side of the rim 207. The exit 220 may be configured (e.g., sized) to allow a single width or diameter of the charging cable 216 to pass through the exit 220. The exit 220 may allow the charging cable 216 to be coupled to an external power source while the base receptacle 202 remains seated flat on a supporting surface. In some implementations, only the length of the charging cable 216 that is needed to reach the external power source may protrude from the exit 220. In some embodiments, the charging cable pocket 218 may be formed by inserting an insert 203 through the top of the base receptacle 202. The bottom of the insert 203 may form a ceiling of the charging cable pocket 218, as depicted in FIG. 3F.

In some embodiments, the neurostimulation device 100 may comprise an RFID tag 224 or another suitable wireless communication mechanism known in the art. The charger 200 may comprise an RFID antenna 226, corresponding to the RFID tag 224, or another suitable wireless communication mechanism known in the art. The RFID tag 224 may be contained within (e.g., embedded within) the band 150, as shown in FIG. 3F. The RFID antenna 226 may be contained internally within the base receptacle 202, as shown in FIG. 3F. The RFID tag 224 may be configured to communicate information to the RFID antenna 226. In some embodiments, the RFID tag 224 may communicate an age or lifetime of the band 150 to the RFID antenna 226. In some embodiments, the RFID tag can be configured with a unique patient identifier that is associated with the base station, to ensure the device is being used by the person/patient it was intended or prescribed for. The age or lifetime of the band 150 may correspond to the age or lifetime of the stimulation electrodes coupled to the band 150. In some embodiments, the charger 200 may comprise a processor or circuitry coupled to the RFID antenna 226. The charger 200 may be configured to prevent charging of the enclosure 102 if the age or lifetime of the band 150 exceeds a threshold limit. In some embodiments, an RFID tag or another digital identification mechanism of a device can prevent operation/charging if it is not operably coupled to its uniquely-identified charger, to prevent swapping of devices or bands (which may be custom configured to treat that specific patient) between patients. The threshold limit (which can be, for example, no more than about 1 week, 2 weeks, 3 weeks, 4 weeks, 2 months, 3 months, 4 months, 5 months, or 6 months in some cases) may prevent using a band 150 beyond the usable lifetime of the band (e.g., the useable lifetime of the electrodes), which may degrade in performance over time and reduce the therapeutic efficacy of stimulation. In some embodiments, the charger 200 may include one or more indicators (e.g., LEDs). The LEDs (not shown) may provide visual indicator signals to indicate the status of the charging to the user. For instance, the LED may shine yellow when charging. The LED may shine green when the enclosure 102 is fully charged. The LED may shine red when the enclosure 102 is coupled to the charger 200, but the charger 200 is not charging the enclosure 102. Non-charging indicators may apply, for example, when the detected age of the band 150 exceeds the threshold limit and/or when another fault condition is detected (e.g., an improper external power source, such as one that exceeds voltage or current limits). In some embodiments, multiple LEDs may be used. In some embodiments, audible or tactile (e.g., haptic) indicators may be used.

In some cases, the charger includes a base station, and can include a first wireless communications antenna configured to receive and transmit data to and from a wireless communications antenna in the enclosure. In some cases, the RFID tag can be configured with a unique identifier associated with the patient or end user and the charger is configured to transmit or receive wireless data when the enclosure is in electrical connection with the charger and the appropriate RFID tag is in detected by an RFID antenna. In some cases, data transmitted between the enclosure and charger include but is not limited to device usage data, error data, motion or activity data, tremor motion data, and/or physiological data. In some cases, the charger can include a second wireless communications antenna configured to receive and transmit data from a system of remote servers, e.g., the cloud. In some cases, the charger is configured to transmit or receive wireless data only when the enclosure is in electrical connection with the charger and the appropriate RFID tag is detected by an RFID antenna. In some embodiments, the enclosure and/or the band is configured to transmit data to the base station of the charger while directly connected to the charger, and lacks any wireless communication capability. The base station of the charger includes the wireless communication capability to transmit the data to an external device. In some embodiments, such features can be advantageous to control bandwidth of data transmitted to an external device, e.g., the cloud and only done when device is not worn (e.g., connected to the base station of the charger). This can improve safety and security. Additionally, requiring multiple physical checks for data transmission can add layers of security to prevent hacking of data or device via the wireless communication connection.

FIGS. 4A-4C are flow charts of methods for fitting and/or testing of a device, according to some embodiments of the invention. As shown in FIG. 4A, a method for fitting and testing proper nerve stimulation can include any number of the following. A patient can be diagnosed with a medical condition, such as essential tremor for example. The physician can use a demo device to fit and test stimulation. The demo device can come in multiple sizes/configurations to accommodate various wrist sizes. The physician can activate the device stimulation features to stimulate one, two, or more nerves of the patient, and adjust stimulation intensity (e.g., current amplitude) to verify that paresthesia is present in the anatomical location(s) of interest (e.g., the hand, such as the areas innervated by the median and radial nerves, for example). Paresthesia can be verified, for example, by asking the patient if they feel numbness and tingling in the locations of interest after activation of the device. The physician can measure the tremor frequency, period, and/or amplitude with the device. The physician can then prescribe a device with customized size and settings.

As shown in FIG. 4B, a method for fitting and in-office test stimulation can include any number of the following. A patient can be diagnosed with a medical condition, such as essential tremor for example. The physician can use a demo device to fit and test stimulation. The demo device can come in multiple sizes/configurations to accommodate various wrist sizes. The physician can activate the device stimulation features to stimulate one, two, or more nerves of the patient, and adjust stimulation intensity (e.g., current amplitude) to verify that paresthesia is present in the anatomical location (s) of interest (e.g., the hand, such as the areas innervated by the median and radial nerves, for example). The physician can measure the tremor motion to calculate tremor frequency, period, and/or amplitude with the device. The physician can then perform a baseline evaluation of tremor. The physician can perform an in-office stimulation session. The physician can then perform a post-stimulation tremor evaluation to determine the response to therapy. The physician can prescribe a device with customized size and settings depending on the degree of response to the in-office stimulation session and other factors.

As shown in FIG. 4C, a method with a fitting and trial usage period can include any number of the following. A patient can be diagnosed with a medical condition, such as essential tremor for example. In some cases, the physician can use a trial device to fit and test stimulation. The trial device can have multiple sizes/configurations to accommodate various wrist sizes. The physician can activate the device stimulation features to stimulate one, two, or more nerves of the patient, and adjust stimulation intensity (i.e., current amplitude) to verify that paresthesia is present in the anatomical location(s) of interest (e.g., the hand, such as the areas innervated by the median and radial nerves, for example). The physician can measure the tremor frequency, period, and/or amplitude with the device. The physician can then perform a baseline evaluation of tremor. The patient can then use the trial device at home for a specified trial period, such as, for example, about 1, 2, 3, 4, 5, 6, 7, 14, 21, 30, 60, 90, or more days, or ranges including any two of the aforementioned values. The physician can then perform a post-stimulation tremor evaluation to determine the response to therapy. In some cases, the device can measure tremor motion post-stimulation to quantify tremor amplitude and transmit that information to the patient or physician. The physician can prescribe a device with customized size and settings depending on the degree of response to the at-home trial stimulation session and other factors.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. For example, actions such as "percutaneously stimulating an afferent peripheral nerve" includes "instructing the stimulation of an afferent peripheral nerve."

What is claimed is:

1. A wearable neurostimulation device for transcutaneously stimulating one or more peripheral nerves of a user, the device comprising:

an enclosure housing circuitry configured to generate electric stimulation signals having a frequency from 1 to 500 Hz, a pulse width of 50 to 500 microseconds and sufficient to reduce tremor of the user, the enclosure having a top surface and a bottom surface; and an adjustable band configured to be worn on a wrist of the user, the band having an inner side and an outer side, the inner side comprising at least one electrode for each nerve to be stimulated, wherein the enclosure is removably attachable from the adjustable band;

wherein the band comprises an electrical interface member configured to electrically couple to the enclosure;

wherein the enclosure comprises one or more electrical stimulation contacts, each electrical stimulation contact corresponding to a different electrode of the band, the electrical stimulation contacts configured to be electrically connected to the electrical interface member;

wherein the band comprises at least a first electrode and a second electrode, the first electrode being configured to stimulate a median nerve of the user and the second electrode being configured to stimulate a radial nerve or an ulnar nerve of the user, wherein a top surface of the enclosure comprises one or more LEDs, wherein the enclosure comprises a stimulation button configured to start and stop delivery of the stimulation signals; and wherein the enclosure and the electrical interface member comprise corresponding keying features configured to ensure the one or more electrical stimulation contacts are electrically coupled to a proper electrode and thereby a proper nerve.

2. The neurostimulation device of claim 1, wherein the stimulation button is positioned on the top surface of the enclosure.

3. The neurostimulation device of claim 2, wherein the stimulation button is biased upward by a bracket spring feature, the bracket spring feature comprising a generally flat surface and a plurality of spring fingers cut from the flat surface, the spring fingers configured to press upward on the stimulation button.

4. The neurostimulation device of claim 1, wherein the enclosure comprises a rechargeable battery.

5. The neurostimulation device of claim 1, wherein the enclosure comprises a sidewall joining the top surface and the bottom surface, and wherein one or more charging ports are positioned on the sidewall.

6. The neurostimulation device of claim 1, wherein the band comprises an aperture on a first end of the band through which a second end of the band is inserted to form a closed loop, wherein the second end of the band comprises a hook and loop fastener for securing the band to itself in an adjustable length manner, and wherein a locking flap extends from the hook and loop fastener to prevent the second end of the band from retreating through the aperture to open the closed loop.

7. The neurostimulation device of claim 1, wherein the enclosure comprises a sidewall joining the top surface and the bottom surface, wherein the sidewall comprises a first surface and a second surface opposing the first surface, wherein the second surface is configured to be a bracing surface.

8. The neurostimulation device of claim 1, wherein the electrical stimulation contacts are configured to directly interface with the electrical interface member via a rotatable connection.

9. A wearable neurostimulation system, the neurostimulation system comprising the neurostimulation device of claim 1, the neurostimulation system further comprising a charger configured to electrically charge the rechargeable battery of the enclosure, the charger comprising:

a top surface, a bottom surface, and a sidewall extending between the top surface and the bottom surface;

a charging pocket formed in the top surface, the pocket configured to receive at least a portion of the enclosure, the charging pocket comprising one or more charging contacts at the bottom of the charging pocket configured to electrically couple to and transfer power to the enclosure;

and a charging cable configured to be coupled to an external power source for drawing power through the charger.

10. The neurostimulation system of claim 9, wherein the band comprises an RFID tag and the charger comprises an RFID antenna.

11. The neurostimulation system of claim 10, wherein the RFID tag is configured to communicate an age of the band to the charger and the charger is configured not to charge the enclosure if the age of the band exceeds a threshold age.

12. The neurostimulation system of claim 9, wherein the charger is configured to receive data from the enclosure when the enclosure is positioned in the charger, and wirelessly transmit the data to an external device.

13. A wearable neurostimulation device for transcutaneously stimulating one or more peripheral nerves of a user, the device comprising:

an enclosure housing circuitry configured to generate electric stimulation signals having a frequency from 1 to 500 Hz, a pulse width of 50 to 500 microseconds and sufficient to reduce tremor of the user; and an adjustable band configured to be worn on a wrist of the user, the band having an inner side and an outer side, the inner side comprising at least one electrode corresponding to each nerve to be stimulated;

wherein the band comprises an electrical interface member configured to electrically couple to the enclosure;

wherein a surface of the enclosure that is hidden from a user when assembled comprises one or more electrical stimulation contacts, each electrical stimulation contact corresponding to a different electrode of the band, the electrical stimulation contacts configured to be electrically connected to the electrical interface member;

wherein the enclosure comprises an inductive coil, wherein the enclosure and the electrical interface member comprise corresponding keying features configured to prevent the neurostimulation device from being worn on a wrong wrist; and wherein the enclosure comprises a rechargeable battery configured to be wirelessly powered by the inductive coil.

14. The neurostimulation device of claim 13, wherein the enclosure is removably and directly attachable to the band without a cable connector therebetween.

15. The neurostimulation device of claim 13, wherein the enclosure is secured to the band via a snap fit.

16. The neurostimulation device of claim 13, wherein the enclosure is secured to the band via a rotatable connection.

17. The neurostimulation device of claim 13, wherein the band comprises an aperture on a first end of the band through which a second end of the band is inserted to form a closed loop, wherein the second end of the band comprises a hook and loop fastener for securing the band to itself in an adjustable length manner, and wherein a locking flap extends from the hook and loop fastener to prevent the second end of the band from retreating through the aperture to open the closed loop.

18. The neurostimulation device of claim 13, wherein the neurostimulation device is configured for either left-handed or right-handed wear.

* * * * *